(12) United States Patent
Dimitrov et al.

(10) Patent No.: US 8,071,323 B2
(45) Date of Patent: Dec. 6, 2011

(54) HUMAN MONOCLONAL ANTIBODIES THAT BIND HUMAN INSULIN LIKE GROWTH FACTORS AND THEIR USE

(75) Inventors: Dimiter S. Dimitrov, Frederick, MD (US); Zhongyu Zhu, Frederick, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 253 days.

(21) Appl. No.: 12/296,328

(22) PCT Filed: Apr. 6, 2007

(86) PCT No.: PCT/US2007/066180
§ 371 (c)(1),
(2), (4) Date: Dec. 31, 2008

(87) PCT Pub. No.: WO2007/118214
PCT Pub. Date: Oct. 18, 2007

(65) Prior Publication Data
US 2010/0055033 A1  Mar. 4, 2010

Related U.S. Application Data

(60) Provisional application No. 60/790,512, filed on Apr. 7, 2006.

(51) Int. Cl.
| | |
|---|---|
| C07K 16/22 | (2006.01) |
| G01N 33/53 | (2006.01) |
| G01N 33/567 | (2006.01) |
| G01N 33/574 | (2006.01) |
| A61K 39/395 | (2006.01) |
| A61K 51/10 | (2006.01) |
| C12N 5/10 | (2006.01) |
| C12N 15/13 | (2006.01) |
| C12N 15/63 | (2006.01) |

(52) U.S. Cl. ........ 435/7.23; 435/7.1; 435/7.2; 435/7.21; 435/40.52; 435/69.6; 435/335; 435/320.1; 436/501; 436/503; 436/63; 436/64; 530/387.1; 530/387.3; 530/388.1; 530/388.15; 530/388.24; 530/388.8; 530/388.85; 530/391.1; 530/391.3; 536/23.5; 424/1.49; 424/9.34; 424/9.341; 424/130.1; 424/133.1; 424/134.1; 424/141.1; 424/142.1; 424/145.1; 424/156.1

(58) Field of Classification Search .......... 435/7.1, 435/7.2, 7.21, 7.23, 40.1, 40.52, 69.6, 320.1, 435/335; 436/501, 503, 63, 64; 530/387.1, 530/387.3, 388.1, 388.15, 388.24, 388.8, 530/388.85, 391.1, 391.3; 536/23.53; 424/1.49, 424/9.34, 9.341, 130.1, 133.1, 134.1, 141.1, 424/142.1, 145.1, 156.1
See application file for complete search history.

(56) References Cited

U.S. PATENT DOCUMENTS

| | | |
|---|---|---|
| 3,791,932 A | 2/1974 | Schuurs et al. |
| 3,817,837 A | 6/1974 | Rubenstein et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,939,350 A | 2/1976 | Kronick et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,275,149 A | 6/1981 | Litman et al. |
| 4,277,437 A | 7/1981 | Maggio |
| 4,366,241 A | 12/1982 | Tom et al. |
| 4,376,110 A | 3/1983 | David et al. |
| 4,391,904 A | 7/1983 | Litman et al. |
| 4,399,216 A | 8/1983 | Axel et al. |
| 4,486,530 A | 12/1984 | David et al. |
| 4,681,581 A | 7/1987 | Coates |
| 4,683,195 A | 7/1987 | Mullis et al. |
| 4,683,202 A | 7/1987 | Mullis |
| 4,735,210 A | 4/1988 | Goldenberg |
| 4,740,461 A | 4/1988 | Kaufman |
| 4,816,567 A | 3/1989 | Cabilly et al. |
| 4,912,040 A | 3/1990 | Kaufman et al. |
| 4,959,455 A | 9/1990 | Clark et al. |
| 5,101,827 A | 4/1992 | Goldenberg |
| 5,102,990 A | 4/1992 | Rhodes |
| 5,194,594 A | 3/1993 | Khawli et al. |

(Continued)

FOREIGN PATENT DOCUMENTS

EP  0 323 997 B1  7/1988

(Continued)

OTHER PUBLICATIONS

Paul, William E. Fundamental Immunology, 3rd Edition, Raven Press, New York, Chapt. 8, pp. 242, 292-295, 1993.* Rudikoff et al. Proc. Natl. Acad. Sci. USA, 79(6):1979-1983, Mar. 1982.*
Colman P. M. Research in Immunology, 145:33-36, 1994.*
Bendig M. M. Methods: A Companion to Methods in Enzymology, 8:83-93, 1995.*
MacCallum et al. J. Mol. Biol., 262, 732-745, 1996.*
Casset et al. Biochemical and Biophysical Research Communications, 307:198-205, 2003.*

(Continued)

*Primary Examiner* — Alana Harris Dent
*Assistant Examiner* — Anne Holleran
(74) *Attorney, Agent, or Firm* — Klarquist Sparkman, LLP

(57) ABSTRACT

Antibody compositions and methods for treatment of neoplastic disease in a mammalian subject are provided. Methods of diagnosing cancer in a mammalian subject are also provided.

52 Claims, 9 Drawing Sheets

U.S. PATENT DOCUMENTS

| | | | |
|---|---|---|---|
| 5,401,629 A | 3/1995 | Harpold et al. |
| 5,436,128 A | 7/1995 | Harpold et al. |
| 5,530,101 A | 6/1996 | Queen et al. |
| 5,545,806 A | 8/1996 | Lonberg et al. |
| 5,545,807 A | 8/1996 | Surani et al. |
| 5,569,825 A | 10/1996 | Lonberg et al. |
| 5,585,089 A | 12/1996 | Queen et al. |
| 5,591,669 A | 1/1997 | Krimpenfort et al. |
| 5,612,205 A | 3/1997 | Kay et al. |
| 5,625,126 A | 4/1997 | Lonberg et al. |
| 5,625,825 A | 4/1997 | Rostoker et al. |
| RE35,500 E | 5/1997 | Rhodes |
| 5,633,425 A | 5/1997 | Lonberg et al. |
| 5,643,763 A | 7/1997 | Dunn et al. |
| 5,648,471 A | 7/1997 | Buttram et al. |
| 5,661,016 A | 8/1997 | Lonberg et al. |
| 5,693,761 A | 12/1997 | Queen et al. |
| 5,693,792 A | 12/1997 | Torii et al. |
| 5,697,902 A | 12/1997 | Goldenberg |
| 5,703,057 A | 12/1997 | Johnston et al. |
| 5,714,350 A | 2/1998 | Co et al. |
| 5,721,367 A | 2/1998 | Kay et al. |
| 5,733,743 A | 3/1998 | Johnson et al. |
| 5,741,957 A | 4/1998 | Deboer et al. |
| 5,750,172 A | 5/1998 | Meade et al. |
| 5,756,687 A | 5/1998 | Denman et al. |
| 5,770,429 A | 6/1998 | Lonberg et al. |
| 5,777,085 A | 7/1998 | Co et al. |
| 5,789,215 A | 8/1998 | Berns et al. |
| 5,789,650 A | 8/1998 | Lonberg et al. |
| 5,814,318 A | 9/1998 | Lonberg et al. |
| 5,827,690 A | 10/1998 | Meade et al. |
| 5,914,241 A | 6/1999 | Valkirs |
| 5,939,598 A | 8/1999 | Kucherlapati et al. |
| 5,965,375 A | 10/1999 | Valkirs |
| 6,075,181 A | 6/2000 | Kucherlapati et al. |
| 6,114,598 A | 9/2000 | Kucherlapati et al. |
| 6,150,584 A | 11/2000 | Kucherlapati et al. |
| 6,162,963 A | 12/2000 | Kucherlapati et al. |
| 6,673,986 B1 | 1/2004 | Kucherlapati et al. |
| 7,064,244 B2 | 6/2006 | Kucherlapati et al. |

FOREIGN PATENT DOCUMENTS

| | | |
|---|---|---|
| EP | 0 256 055 B1 | 8/1991 |
| EP | 0 338 841 B1 | 3/1995 |
| EP | 0 216 846 B2 | 4/1995 |
| EP | 0 463 151 B1 | 6/1996 |
| EP | 0 546 073 B1 | 9/1997 |
| EP | 1 505 075 A1 | 2/2005 |
| WO | WO 91/17271 A1 | 11/1991 |
| WO | WO 92/01047 A1 | 1/1992 |
| WO | WO 92/03918 A1 | 3/1992 |
| WO | WO 92/22645 A1 | 12/1992 |
| WO | WO 92/22647 A1 | 12/1992 |
| WO | WO 92/22670 A1 | 12/1992 |
| WO | WO 93/06213 A1 | 4/1993 |
| WO | WO 93/12227 A1 | 6/1993 |
| WO | WO 94/00569 A1 | 1/1994 |
| WO | WO 94/02602 A1 | 2/1994 |
| WO | WO 94/25585 A1 | 11/1994 |
| WO | WO 94/29444 A1 | 12/1994 |
| WO | WO 96/14436 A1 | 5/1996 |
| WO | WO 96/34096 A1 | 10/1996 |
| WO | WO 97/08320 A1 | 3/1997 |
| WO | WO 97/13852 A1 | 4/1997 |
| WO | WO 97/38137 A1 | 10/1997 |
| WO | WO 98/24884 A1 | 6/1998 |
| WO | WO 98/24893 A2 | 6/1998 |
| WO | WO 00/37504 A2 | 6/2000 |
| WO | WO 01/14424 A2 | 3/2001 |
| WO | WO03093317 A1 * | 11/2003 |
| WO | WO 03/100008 A2 | 12/2003 |
| WO | WO 2004/092219 | 10/2004 |

OTHER PUBLICATIONS

Belagaje R, et al., Total synthesis of a tyrosine suppressor transfer RNA gene. XIV. Chemical synthesis of oligonucleotide segments corresponding to the terminal regions. J Biol Chem. Jul. 10, 1979;254(13):5765-80.

Bird RE, et al., Single-chain antigen-binding proteins. Science. Oct. 21, 1988;242(4877):423-6. Erratum in: Science Apr. 28, 1989;244(4903):409.

Blake J, Litzi-Davis L. Evaluation of peptide libraries: an iterative strategy to analyze the reactivity of peptide mixtures with antibodies. Bioconjug Chem. Nov.-Dec. 1992;3(6):510-3.

Bowie JU, et al., A method to identify protein sequences that fold into a known three-dimensional structure. Science. Jul. 12, 1991;253(5016):164-70.

Burtrum D et al. A fully human monoclonal antibody to the insulin-like growth factor I receptor blocks ligand-dependent signaling and inhibits human tumor growth in vivo. Cancer Res. Dec. 15, 2003;63(24):8912-21.

Cevc G, et al., Ultraflexible vesicles, Transfersomes, have an extremely low pore penetration resistance and transport therapeutic amounts of insulin across the intact mammalian skin. Biochim Biophys Acta. Jan. 19, 1998;1368(2):201-15.

Chaudhary VK, et al., A rapid method of cloning functional variable-region antibody genes in *Escherichia coli* as single-chain immunotoxins. Proc Natl Acad Sci U S A. Feb. 1990;87(3):1066-70. Erratum in: Proc Natl Acad Sci U S A Apr. 1990;87(8):3253.

Chen SY, et al., Intracellular antibodies as a new class of therapeutic molecules for gene therapy. Hum Gene Ther. May 1994;5(5):595-601.

Chiswell DJ, McCafferty J. Phage antibodies: will new 'coliclonal' antibodies replace monoclonal antibodies? Trends Biotechnol. Mar. 1992;10(3):80-4.

Chothia C, et al., Conformations of immunoglobulin hypervariable regions. Nature. Dec. 21-28, 1989;342(6252):877-83.

Chothia C, Lesk AM. Canonical structures for the hypervariable regions of immunoglobulins. J Mol Biol. Aug. 20, 1987;196(4):901-17.

Cwirla SE, et al., Peptides on phage: a vast library of peptides for identifying ligands. Proc Natl Acad Sci U S A. Aug. 1990;87(16):6378-82.

Dranoff G, et al., Vaccination with irradiated tumor cells engineered to secrete murine granulocyte-macrophage colony-stimulating factor stimulates potent, specific, and long-lasting anti-tumor immunity. Proc Natl Acad Sci U S A. Apr. 15, 1993;90(8):3539-43.

Evans BE, et al., Design of nonpeptidal ligands for a peptide receptor: cholecystokinin antagonists. J Med Chem. Jul. 1987;30(7):1229-39.

Fanger MW, et al., Production and use of anti-FcR bispecific antibodies. Immunomethods. Feb. 1994;4(1):72-81.

Fauchere, Elements for the Rational Design of Peptide Drugs. J. Adv. Drug Res., 1986, 15:29.

Felici F, et al., Selection of antibody ligands from a large library of oligopeptides expressed on a multivalent exposition vector. J Mol Biol. Nov. 20, 1991;222(2):301-10.

Fry DW, et al., Specific, irreversible inactivation of the epidermal growth factor receptor and erbB2, by a new class of tyrosine kinase inhibitor. Proc Natl Acad Sci U S A. Sep. 29, 1998;95(20):12022-7.

Fundamental Immunology, Ch. 7 (Paul, W., ed), 2nd ed. Raven Press, N.Y. (1989).

Furet P, et al., Modelling study of protein kinase inhibitors: binding mode of staurosporine and origin of the selectivity of CGP 52411. J Comput Aided Mol Des. Dec. 1995;9(6):465-72.

Gao C, et al., A method for the generation of combinatorial antibody libraries using pIX phage display. Proc Natl Acad Sci U S A. Oct. 1, 2002;99(20):12612-6.

Gilman, G proteins: Transducers of recep-tor-generated signals. Ann. Rev. Biochem., 1987, 56: 625-649.

Ginalski K, et al., Modelling of active forms of protein kinases: p38—a case study. Acta Biochim Pol. 1997;44(3):557-64.

Gorman CM, et al., The Rous sarcoma virus long terminal repeat is a strong promoter when introduced into a variety of eukaryotic cells by DNA-mediated transfection. Proc Natl Acad Sci U S A. Nov. 1982;79(22):6777-81.

Goya M, et al., Growth inhibition of human prostate cancer cells in human adult bone implanted into nonobese diabetic/severe combined immunodeficient mice by a ligand-specific antibody to human insulin-like growth factors. Cancer Res. Sep. 1, 2004;64(17):6252-8.

Green LL, et al., Antigen-specific human monoclonal antibodies from mice engineered with human Ig heavy and light chain YACs. Nat Genet. May 1994;7(1):13-21.

Green LL, Jakobovits A. Regulation of B cell development by variable gene complexity in mice reconstituted with human immunoglobulin yeast artificial chromosomes. J Exp Med. Aug. 3, 1998;188(3):483-95.

Grosschedl R, Baltimore D. Cell-type specificity of immunoglobulin gene expression is regulated by at least three DNA sequence elements. Cell. Jul. 1985;41(3):885-97.

Hailey J et al. Neutralizing anti-insulin-like growth factor receptor 1 antibodies inhibit receptor function and induce receptor degradation in tumor cells. Mol Cancer Ther. Dec. 2002;1(14):1349.

Hanes J, Plückthun A. In vitro selection and evolution of functional proteins by using ribosome display. Proc Natl Acad Sci U S A. May 13, 1997;94(10):4937-42.

Harding CV, et al., Turnover of Ia-peptide complexes is facilitated in viable antigen-presenting cells: biosynthetic turnover of Ia vs. peptide exchange. Proc Natl Acad Sci U S A. Jun. 1989;86(11):4230-4.

Hodgson J. Making monoclonals in microbes. Biotechnology (N Y). May 1991;9(5):421-5.

Hofmann K, et al., A model of Cdc25 phosphatase catalytic domain and Cdk-interaction surface based on the presence of a rhodanese homology domain. J Mol Biol. Sep. 11, 1998;282(1):195-208.

Hoogenboom et al., Building antibodies from their genes. Immunol. Reviews, 1992, 130: 43-68.

Holliger P, et al., "Diabodies": small bivalent and bispecific antibody fragments. Proc Natl Acad Sci U S A. Jul. 15, 1993;90(14):6444-8.

Houghten RA, et al., The use of synthetic peptide combinatorial libraries for the identification of bioactive peptides. Biotechniques. Sep. 1992;13(3):412-21.

Hsu LC, et al., Cloning of cDNAs for human aldehyde dehydrogenases 1 and 2. Proc Natl Acad Sci U S A. Jun. 1985;82(11):3771-5.

Hurwitz AA, et al., Combination immunotherapy of primary prostate cancer in a transgenic mouse model using CTLA-4 blockade. Cancer Res. May 1, 2000;60(9):2444-8.

Huston JS, et al., Protein engineering of antibody binding sites: recovery of specific activity in an anti-digoxin single-chain Fv analogue produced in Escherichia coli. Proc Natl Acad Sci U S A. Aug. 1988;85(16):5879-83.

Hynes RO. Integrins: versatility, modulation, and signaling in cell adhesion. Cell. Apr. 3, 1992;69(1):11-25.

Ill CR, et al., Design and construction of a hybrid immunoglobulin domain with properties of both heavy and light chain variable regions. Protein Eng. Aug. 1997;10(8):949-57.

Joukov V, et al., Identification of csk tyrosine phosphorylation sites and a tyrosine residue important for kinase domain structure. Biochem J. Mar. 15, 1997;322 ( Pt 3):927-35.

Junghans et al., Cancer Chemotherapy and Biotherapy, 2$^{nd}$ ed., chafier and Longo, Eds., Lippincott Raven 1996, pp. 655-686.

Kam W, et al., Cloning, sequencing, and chromosomal localization of human term placental alkaline phosphatase cDNA. Proc Natl Acad Sci U S A. Dec. 1985;82(24):8715-9.

Khorana HG. Total synthesis of a gene. Science. Feb. 16, 1979;203(4381):614-25.

Kostelny SA, et al., Formation of a bispecific antibody by the use of leucine zippers. J Immunol. Mar. 1, 1992;148(5):1547-53.

Kuwabara I, et al., Efficient epitope mapping by bacteriophage lambda surface display. Nat Biotechnol. Jan. 1997;15(1):74-8.

Langer R, et al., New advances in microsphere-based single-dose vaccines. Adv Drug Deliv Rev. Oct. 13, 1997;28(1):97-119.

Langer R. New methods of drug delivery. Science. Sep. 28, 1990;249(4976):1527-33.

Lathe R. Synthetic oligonucleotide probes deduced from amino acid sequence data. Theoretical and practical considerations. J Mol Biol. May 5, 1985;183(1):1-12.

LeRoith D, Helman L. The new kid on the block(ade) of the IGF-1 receptor. Cancer Cell. Mar. 2004;5(3):201-2. Review. Erratum in: Cancer Cell. Apr. 2004;5(4):403.

Liu AY, et al., Chimeric mouse-human IgG1 antibody that can mediate lysis of cancer cells. Proc Natl Acad Sci U S A. May 1987;84(10):3439-43.

Liu AY, et al., Production of a mouse-human chimeric monoclonal antibody to CD20 with potent Fc-dependent biologic activity. J Immunol. Nov. 15, 1987;139(10):3521-6.

Lu D et al. Simultaneous blockade of both the epidermal growth factor receptor and the insulin-like growth factor receptor signaling pathways in cancer cells with a fully human recombinant bispecific antibody. J Biol Chem. Jan. 23, 2004;279(4):2856-65.

Maloney EK et al. An anti-insulin-like growth factor I receptor antibody that is a potent inhibitor of cancer cell proliferation. Cancer Res. Aug. 5, 2003;63(16):5073-83-53.

Mandel C, et al., ABGEN: a knowledge-based automated approach for antibody structure modeling. Nat Biotechnol. Mar. 1996;14(3):323-8.

Mao S, et al., Phage-display library selection of high-affinity human single-chain antibodies to tumor-associated carbohydrate antigens sialyl Lewisx and Lewisx. Proc Natl Acad Sci U S A. Jun. 8, 1999;96(12):6953-8.

Marasco WA. Intrabodies: turning the humoral immune system outside in for intracellular immunization. Gene Ther. Jan. 1997;4(1):11-5.

Marks JD, et al., Human antibody fragments specific for human blood group antigens from a phage display library. Biotechnology (N Y). Oct. 1993;11(10):1145-9.

Martin F, et al., The affinity-selection of a minibody polypeptide inhibitor of human interleukin-6. EMBO J. Nov. 15, 1994;13(22):5303-9.

Mendez MJ, et al., Functional transplant of megabase human immunoglobulin loci recapitulates human antibody response in mice. Nat Genet. Feb. 1997;15(2):146-56. Erratum in: Nat Genet Aug. 1997;16(4):410.

Miyamoto S, et al., Blockade of paracrine supply of insulin-like growth factors using neutralizing antibodies suppresses the liver metastasis of human colorectal cancers. Clin Cancer Res. May 1, 2005;11(9):3494-502.

Monfardini C, et al., Rational design, analysis, and potential utility of GM-CSF antagonists. Proc Assoc Am Physicians. Nov. 1996;108(6):420-31.

Nyyssönen E, et al., Efficient production of antibody fragments by the filamentous fungus Trichoderma reesei. Biotechnology (N Y). May 1993;11(5):591-5.

Okayama H, Berg P. A cDNA cloning vector that permits expression of cDNA inserts in mammalian cells. Mol Cell Biol. Feb. 1983;3(2):280-9.

Osborn L. Leukocyte adhesion to endothelium in inflammation. Cell. Jul. 13, 1990;62(1):3-6.

Parmley SF, Smith GP. Antibody-selectable filamentous fd phage vectors: affinity purification of target genes. Gene. Dec. 20, 1988;73(2):305-18.

Paul A, et al., Transdermal immunization with large proteins by means of ultradeformable drug carriers. Eur J Immunol. Dec. 1995;25(12):3521-4.

Pennica D, et al., Cloning and expression of human tissue-type plasminogen activator cDNA in E. coli. Nature. Jan. 20, 1983;301(5897):214-21.

Peters WP, et al., Neutrophil migration is defective during recombinant human granulocyte-macrophage colony-stimulating factor infusion after autologous bone marrow transplantation in humans. Blood. Oct. 1988;72(4):1310-5.

Pinilla C, et al., Rapid identification of high affinity peptide ligands using positional scanning synthetic peptide combinatorial libraries. Biotechniques. Dec. 1992;13(6):901-5.

Queen C, et al., A humanized antibody that binds to the interleukin 2 receptor. Proc Natl Acad Sci U S A. Dec. 1989;86(24):10029-33.

Restifo et al., Cancer: Principles and Practice of Oncology, 61: 3023-3043, 1997.

Rizo J, Gierasch LM. Constrained peptides: models of bioactive peptides and protein substructures. Annu Rev Biochem. 1992;61:387-418.

Russell SJ, et al., Retroviral vectors displaying functional antibody fragments. Nucleic Acids Res. Mar. 11, 1993;21(5):1081-5.

Scott JK, Smith GP. Searching for peptide ligands with an epitope library. Science. Jul. 27, 1990;249(4967):386-90.

Scott JK. Discovering peptide ligands using epitope libraries. Trends Biochem Sci. Jul. 1992;17(7):241-5.

Singh J, et al., Structure-based design of a potent, selective, and irreversible inhibitor of the catalytic domain of the erbB receptor subfamily of protein tyrosine kinases. J Med Chem. Mar. 28, 1997;40(7):1130-5.

Siraganian et al., Histamine secretion from mast cells and basophils TIPS, 1983; 4:432-437.

Songsivilai S, Lachmann PJ. Bispecific antibody: a tool for diagnosis and treatment of disease. Clin Exp Immunol. Mar. 1990;79(3):315-21.

Springer TA. Adhesion receptors of the immune system. Nature. Aug. 2, 1990;346(6283):425-34.

Suzuki et al., Complete amino acid sequence of human vitronectin deduced from cDNA. Similarity of cell attachment sites in vitronectin and fibronectin. EMBO J., 1985, 4: 2519-2524.

Thornton JM, et al., Protein structure. Prediction of progress at last. Nature. Nov. 14, 1991;354(6349):105-6.

Traunecker A, et al., Bispecific single chain molecules (Janusins) target cytotoxic lymphocytes on HIV infected cells. EMBO J. Dec. 1991;10(12):3655-9.

Traunecker A, et al., Janusin: new molecular design for bispecific reagents. Int J Cancer Suppl. 1992;7:51-2.

van Elsas A, et al., Combination immunotherapy of B16 melanoma using anti-cytotoxic T lymphocyte-associated antigen 4 (CTLA-4) and granulocyte/macrophage colony-stimulating factor (GM-CSF)-producing vaccines induces rejection of subcutaneous and metastatic tumors accompanied by autoimmune depigmentation. J Exp Med. Aug. 2, 1999;190(3):355-66.

Veber and Freidinger, The design of metabolically-stable peptide analogs. TINS, 1985, 8:392-396.

Vitetta ES, et al., Immunotoxins: magic bullets or misguided missiles? Immunol Today. Jun. 1993;14(6):252-9.

Walter P, et al., Cloning of the human estrogen receptor cDNA. Proc Natl Acad Sci U S A. Dec. 1985;82(23):7889-93.

Ward ES, et al., Binding activities of a repertoire of single immunoglobulin variable domains secreted from *Escherichia coli*. Nature. Oct. 12, 1989;341(6242):544-6.

Windhagen A, et al., Modulation of cytokine patterns of human autoreactive T cell clones by a single amino acid substitution of their peptide ligand. Immunity. Apr. 1995;2(4):373-80.

Winter G, Harris WJ. Humanized antibodies. Immunol Today. Jun. 1993;14(6):243-6.

Wright A, et al., Genetically engineered antibodies: progress and prospects. Crit Rev Immunol. 1992;12(3-4):125-68.

Wu R, Bahl CP. Synthetic oligodeoxynucleotides for analyses of DNA structure and function. Prog Nucleic Acid Res Mol Biol. 1978;21:101-41.

Yu H, Rohan T. Role of the insulin-like growth factor family in cancer development and progression. J Natl Cancer Inst. Sep. 20, 2000;92(18):1472-89.

Zhang MY, et al., Identification and characterization of a new cross-reactive human immunodeficiency virus type 1-neutralizing human monoclonal antibody. J Virol. Sep. 2004;78(17):9233-42.

Hoogenboom and Chames, "Natural and Designer Binding Sites Made by Phage Display Technology," *Immunology Today* 21(8):371-378 (Aug. 2000).

Maynard and Georgiou, "Antibody Engineering," *Annual Review of Biomedical Engineering* 2:339-379 (2000).

* cited by examiner

HUMAN MONOCLONAL ANTIBODIES THAT BIND HUMAN INSULIN LIKE GROWTH FACTORS AND THEIR USE

CROSS-REFERENCE TO RELATED APPLICATIONS

This application is the National Stage of International Application No. PCT/US2007/066180, filed Apr. 6, 2007, which claims the benefit of U.S. Provisional Application No. 60/790,512 filed Apr. 7, 2006, each of which is incorporated herein by reference in its entirety.

FIELD

The invention generally relates to an antibody composition and a method for treatment of neoplastic disease in a mammalian subject. An isolated human monoclonal antibody binds to insulin-like growth factor I or to both insulin-like growth factor I and insulin-like growth factor II. The invention further relates to methods of diagnosing cancer in a mammalian subject.

BACKGROUND

Cancer therapies are based on the theory that cells with accelerated rates of division and proliferation are predisposed to the development of cancer. Recently, a number of epidemiologic studies have shown consistently that high circulating levels of a potent mitogen, insulin-like growth factor (IGF)-I, are associated with increased risk for several common cancers, including those of the breast, prostate, lung, and colorectum. The level of IGF-binding protein (IGFBP)-3, a major IGF-I-binding protein in serum that, in most situations, suppresses the mitogenic action of IGF-I, is inversely associated with the risk of these cancers.

Functionally, IGF-I not only stimulates cell proliferation but also inhibits apoptosis. The combination of these mitogenic and antiapoptotic effects can have an impact on tumor growth. Besides their direct effect on cancer-related cellular activities, members of the IGF family also interact with a variety of molecules that are involved in cancer development and progression, including the sex steroid hormones, products of tumor suppressor genes, and other growth factors. Furthermore, the expression and production of IGF-I, a peptide hormone that is involved in regulating human growth and development, are influenced by nutrition and physical activity. Experiments to understand the molecular structure and physiologic function of members of the IGF family provide insights into the role of mitogenic growth factors in carcinogenesis. Yu and Rohan, *J. Natl. Cancer Inst.* 92: 1472-1489, 2000.

IGFs stimulate the proliferation of cultured human breast cancer cells. This stimulation is mediated through the receptor, insulin-like growth factor receptor 1 (IGFR-1), which is a member of the receptor tyrosine kinase family. When activated by its ligands (IGF-I or IGF-II), IGFR1 phosphorylates tyrosine residues on two major substrates, IRS-1 and Shc, which subsequently signal through the Ras/Raf and phosphatidylinositol 3'-kinase/AKT pathways. IGFR1 plays a crucial role in transformation. Cells derived from IGFR1 knockout mice are resistant to transformation by various viral and cellular oncogenes, including SV40 large T antigen and activated ras, whereas fibroblast cells from wild-type mice can be readily transformed by these oncogenes.

There is increasing epidemiological evidence to link elevated plasma IGF-I level with prostate, breast, and colon cancer risk. Breast cancer tissues from patients exhibit higher IGFR1 expression than adjacent normal tissue, suggesting a link between IGFR1 and breast epithelial cell transformation. It has been reported that the transformation capacity of tumor cells is attenuated when IGFR1 is inhibited using an antisense strategy, neutralizing antibody (anti-IR3 or anti-IGF-I) or dominant negative truncation of the receptor. Hailey, J. et al, *Molecular Cancer Therapeutics* 1: 1349-1353, 2002; Maloney E. K., et al, *Cancer Res.* 63: 5073-5083, 2003; Burtrum D., et al, *Cancer Res.*, 63: 8912-8921, 2003; Lu et al., *J. Biol. Chem.* 279: 2856-2865, 2004; Miyamoto et al., *Clin. Cancer Res.* 11: 3494-3502, 2005; Goya et al., *Cancer Research* 64: 6252-6258, 2004. A need exists in the art for improved multi-target therapies to treat neoplastic disease and metastatic cancers.

SUMMARY

The present invention generally relates to antibody compositions and methods for treatment of neoplastic disease in a mammalian subject. The present invention further relates to methods of diagnosing neoplastic disease in a mammalian subject. The antibody compositions are isolated monoclonal antibodies that bind to insulin-like growth factor I. Another set of antibody compositions are monoclonal antibodies that bind to insulin-like growth factor I and are cross-reactive to and bind to insulin-like growth factor II. The isolated monoclonal antibodies are, for example, human, non-human primate, rabbit, rat or mouse antibodies. The isolated human monoclonal antibody compositions that bind to insulin-like growth factor I are, for example, m705 and m706. The isolated human monoclonal antibody compositions that bind to both insulin-like growth factor I and insulin-like growth factor II are m708 and m708.2. Monoclonal antibodies m705, m706, m708, and m708.2 do not bind to human insulin. m705 has a $V_H$ chain amino acid sequence comprising SEQ ID NO: 1 and a $V_L$ chain amino acid sequence comprising SEQ ID NO: 2. m706 has a $V_H$ chain amino acid sequence comprising SEQ ID NO: 3 and a $V_L$ chain amino acid sequence comprising SEQ ID NO: 4. m708 has a $V_H$ chain amino acid sequence comprising SEQ ID NO: 5 and a $V_L$ chain amino acid sequence comprising SEQ ID NO: 6. m708.2 has a $V_H$ chain amino acid sequence comprising SEQ ID NO: 7 and a $V_L$ chain amino acid sequence comprising SEQ ID NO: 8.

An isolated monoclonal antibody is provided which binds to human insulin-like growth factor I and human insulin-like growth factor II comprising an amino acid sequence in its heavy chain variable region as set forth in SEQ ID NO: 7 or an amino acid sequence which is at least 90% homologous to SEQ ID NO: 7.

An isolated monoclonal antibody is provided which binds to human insulin-like growth factor I and human insulin-like growth factor II comprising an amino acid sequence in its light chain variable region as set forth in SEQ ID NO: 8 or an amino acid sequence which is at least 90% homologous to SEQ ID NO: 8.

An isolated monoclonal antibody is provided which binds to human insulin-like growth factor I and human insulin-like growth factor II comprising amino acid sequences in their heavy chain variable regions or light chain variable regions as set forth in SEQ ID NOs: 7 and 8, respectively, or amino acid sequences which are at least 90% homologous, respectively. A pharmaceutical composition is provided comprising one or more of the antibodies of the present invention and a pharmaceutically acceptable carrier.

In a further aspect, the antibody provides at least one CDR sequence including, but not limited to, $V_L$: Q S I S S (SEQ ID NO: 9), V$_L$: A A S (SEQ ID NO: 10), V$_L$: Q Q S Y S T P S T F (SEQ ID NO: 11), V$_H$: G G T F S S Y A (SEQ ID NO: 12), V$_H$:G I I P I L G I A (SEQ ID NO: 13), or V$_H$: A R G P R G Y S Y N F D Y (SEQ ID NO: 14). In a further aspect, the antibody includes, but is not limited to, an IgG$_1$, an IgG$_2$, an IgG$_3$, an IgG$_4$, an IgM, an IgA$_1$, an IgA$_2$, a secretory IgA, an IgD, or an IgE antibody. The antibody can be an IgG$_1$κ or IgG$_1$λ isotype. the antibody is an IgG$_4$κ or IgG$_4$λ isotype. The antibody can be an IgG$_1$, an IgG$_2$, an IgG$_3$, an IgG$_4$, an IgM, an IgA$_1$, an IgA$_2$, a secretory IgA, an IgD, or an IgE antibody. The antibody can be an IgG$_1$κ or IgG$_1$λ isotype. The antibody can be an IgG$_4$κ or IgG$_4$λ isotype. In a detailed aspect the antibody is human, non-human primate, rabbit, rodent, rat, or mouse, or a combination thereof.

In another aspect, the isolated monoclonal antibody of the present invention has one or more of the following characteristics: (i) inhibits IGF-1 receptor phosphorylation in an in vitro MCF-7 breast cancer cell assay at an antibody concentration about 4 nM or greater; (ii) inhibits IGF-I binding or IGF-II binding to IGF-1 receptor; or (iii) inhibits cell migration in a cell migration assay.

In another aspect, the isolated monoclonal antibody of the present invention has a dissociation equilibrium constant (K$_D$) of approximately $10^{-8}$ M or less, when determined by surface plasmon resonance (SPR) using recombinant human insulin-like growth factor I or human insulin-like growth factor II as an analyte and the antibody as a ligand.

An isolated monoclonal antibody is provided in a further aspect which is capable of binding human insulin-like growth factor I and insulin-like growth factor II with a binding affinity of about $10^8$ M$^{-1}$ or greater. An isolated monoclonal antibody is provided in a further aspect which is capable of binding human insulin-like growth factor I and insulin-like growth factor II with a binding affinity of about $10^9$ M$^{-1}$ or greater. In a detailed aspect, the isolated monoclonal antibody is an intact antibody, an intact IgG$_1$ antibody, an intact IgG$_2$ antibody, an intact IgG$_3$ antibody, an intact IgG$_4$ antibody, an intact IgM antibody, an intact IgA$_1$ antibody, an intact IgA$_2$ antibody, an intact secretory IgA antibody, an intact IgD antibody, or an intact IgE antibody, wherein the antibody is glycosylated in a eukaryotic cell. In a further aspect, the isolated monoclonal antibody is an antibody fragment or a single chain antibody. The antibody can be a monoclonal antibody. The antibody can be a F(ab')$_2$, Fab, Fv, or Fd fragment. The antibody can be antigen-specific.

In a further aspect, the isolated monoclonal antibody of the present invention is a binding-domain immunoglobulin fusion protein comprising (i) a variable heavy chain amino acid sequence as set forth in SEQ ID NO: 7 or a variable heavy chain sequence which is at least 90% homologous to SEQ ID NO: 7, fused to a variable light chain amino acid sequence as set forth in SEQ ID NO: 8 or a variable light chain sequence which is at least 90% homologous to SEQ ID NO: 8 via a linker peptide, that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. The antibody can bind to a predetermined antigen with an equilibrium association constant (Ka), for example, of at least $10^8$ M$^{-1}$, of at least $10^9$ M$^{-1}$, or of at least $10^{10}$ M$^{-1}$.

An isolated human monoclonal antibody is provided which binds to human insulin-like growth factor I and human insulin-like growth factor II. In one aspect, the antibody comprises at least one CDR sequence of: V$_L$: Q S I S S (SEQ ID NO: 9), V$_L$: A A S (SEQ ID NO: 10), V$_L$: Q Q S Y S T P S T F (SEQ ID NO: 11), V$_H$: G G T F S S Y A (SEQ ID NO: 12), V$_H$: G I I P I L G I A (SEQ ID NO: 13), or V$_H$: A R G P R G Y S Y N F D Y (SEQ ID NO: 14).

An isolated human monoclonal antibody is provided which binds to human insulin-like growth factor I comprising an amino acid sequence in its human heavy chain variable region as set forth in SEQ ID NO: 1 or an amino acid sequence which is at least 90% homologous to SEQ ID NO: 1. An isolated human monoclonal antibody is provided which binds to human insulin-like growth factor I comprising an amino acid sequence in its human light chain variable region as set forth in SEQ ID NO: 2 or an amino acid sequence which is at least 90% homologous to SEQ ID NO: 2. An isolated human monoclonal antibody which binds to human insulin-like growth factor I comprising an amino acid sequence in its human heavy chain variable region as set forth in SEQ ID NO: 3 or an amino acid sequence which is at least 90% homologous to SEQ ID NO: 3. An isolated human monoclonal antibody is provided which binds to human insulin-like growth factor I comprising an amino acid sequence in its human light chain variable region as set forth in SEQ ID NO: 4 or an amino acid sequence which is at least 90% homologous to SEQ ID NO: 4. An isolated human monoclonal antibody is provided which binds to human insulin-like growth factor I and human insulin-like growth factor II comprising an amino acid sequence in its human heavy chain variable region as set forth in SEQ ID NO: 5 or an amino acid sequence which is at least 90% homologous to SEQ ID NO: 5. An isolated human monoclonal antibody is provided which binds to human insulin-like growth factor I and human insulin-like growth factor II comprising an amino acid sequence in its human light chain variable region as set forth in SEQ ID NO: 6 or an amino acid sequence which is at least 90% homologous to SEQ ID NO: 6. A pharmaceutical composition is provided comprising one or more of the antibodies of the present invention and a pharmaceutically acceptable carrier.

An isolated nucleic acid is provided encoding the heavy chain immunoglobulin variable domain sequence or the light chain immunoglobulin variable domain sequence of the protein/antibody of the present invention. A pharmaceutical composition is provided comprising the nucleic acid and a pharmaceutically acceptable carrier. A recombinant cell is provided that contains one or more nucleic acids that encode the immunoglobulin variable domain sequences of the antibody of the present invention. A host cell that contains a first nucleic acid sequence encoding a polypeptide comprising a HC variable domain of an antibody and a second nucleic acid sequence encoding a polypeptide comprising a LC variable domain of the antibody, wherein the antibody is a protein of the present invention. A method of preparing an antibody capable of binding insulin growth factor I and insulin growth factor II, the method comprising expressing the nucleic acid of the present invention in a host cell under conditions to provide for expression of the nucleic acid, followed by recovery of the antibody.

An isolated recombinant anti-IGF-I and anti-IGF-II antibody or antigen-binding fragment thereof, the antibody is provided comprising a human constant region wherein the antibody or antigen binding fragment (i) competitively inhibits binding of m708.2 antibody (ATCC Accession No. PTA-8341) to human IGF-I and human IGF-II, and (ii) binds to a neutralizing epitope of human IGF-I and human IGF-II in vivo with an affinity of at least 1×$10^8$ liter/mole, or with an affinity of at least 1×$10^9$ liter/mole, measured as an associate constant (Ka) as determined by surface plasmon resonance. The antibody or antigen-binding fragment can comprise a human constant region and a human variable region. The antibody or antigen-binding fragment can comprise at least one human light chain and at least one human heavy chain. In a further aspect, the light chain comprises all antigen-binding regions of the light chain of m708.2 (ATCC Accession No. PTA-8341). The heavy chain can comprise all antigen-binding regions of the heavy chain of m708.2 (ATCC Accession No. PTA-8341). The light chain can comprise all antigen-binding regions of the light chain of m708.2 (ATCC Accession No. PTA-8341) and wherein the heavy chain comprises all antigen-binding regions of the heavy chain of m708.2 (ATCC Accession No. PTA-8341).

An isolated recombinant anti-IGF-I and anti-IGF-II antibody or antigen-binding fragment thereof is provided, the antibody comprising a human constant region wherein the antibody or antigen binding fragment (i) comprises the antigen binding region of m708.2 antibody (ATCC Accession No. PTA-8341), and (ii) binds to a neutralizing epitope of human IGF-I and human IGF-II in vivo with an affinity of at least $1\times10^8$ liter/mole, or with an affinity of at least $1\times10^9$ liter/mole, measured as an associate constant (Ka) as determined by surface plasmon resonance. An isolated recombinant anti-IGF-I and anti-IGF-II antibody or antigen-binding fragment thereof is provided, the antibody comprising a human IgG1 constant region wherein the antibody or antigen binding fragment (i) competitively inhibits binding of m708.2 antibody (ATCC Accession No. PTA-8341) to human IGF-I and human IGF-II, and (ii) binds to a neutralizing epitope of human IGF-I and human IGF-II in vivo with an affinity of at least $1\times10^8$ liter/mole, or with an affinity of at least $1\times10^9$ liter/mole, measured as an associate constant (Ka) as determined by surface plasmon resonance. An isolated recombinant anti-IGF-I and anti-IGF-II antibody or antigen-binding fragment thereof is provided, the antibody comprising a human IgG1 constant region wherein the antibody or antigen binding fragment (i) comprises the antigen binding region of m708.2 antibody (ATCC Accession No. PTA-8341), and (ii) binds to a neutralizing epitope of human IGF-I and human IGF-II in vivo with an affinity of at least $1\times10^8$ liter/mole, or with an affinity of at least $1\times10^9$ liter/mole, measured as an associate constant (Ka) as determined by surface plasmon resonance.

A method of detecting human insulin growth factor I and insulin growth factor II in a sample is provided comprising: (a) providing a sample; (b) contacting the sample of (a) with a human monoclonal antibody m708 or m708.2 which specifically binds a polypeptide comprising human insulin growth factor I and insulin growth factor II under conditions which permit binding of the polypeptide ligand to human insulin growth factor I and insulin growth factor II; and (c) detecting binding of the antibody m708 or m708.2 with human insulin growth factor I and insulin growth factor II in the sample, wherein detection of binding indicates the presence of human insulin growth factor I and insulin growth factor II in the sample; thereby detecting human insulin growth factor I and insulin growth factor II in the sample.

A method of detecting human insulin growth factor I and insulin growth factor II in a sample is provided comprising: (a) providing a sample; (b) contacting the sample of (a) with a human monoclonal antibody m708 or m708.2 which specifically binds a polypeptide comprising human insulin growth factor I and insulin growth factor II under conditions which permit binding of the polypeptide ligand to human insulin growth factor I and insulin growth factor II; and (c) detecting binding of the antibody m708 or m708.2 with human insulin growth factor I and insulin growth factor II in the sample, wherein detection of binding indicates the presence of human insulin growth factor I and insulin growth factor II in the sample; thereby detecting human insulin growth factor I and insulin growth factor II in the sample.

A method of detecting human insulin growth factor I in a sample is provided comprising: (a) providing a sample; (b) contacting the sample of (a) with a human monoclonal antibody m705 or m706 which specifically binds a polypeptide comprising human insulin growth factor I under conditions which permit binding of the polypeptide ligand to human insulin growth factor I; and (c) detecting binding of the antibody m705 or m706 with human insulin growth factor I in the sample, wherein detection of binding indicates the presence of human insulin growth factor I in the sample; thereby detecting human insulin growth factor I in the sample.

A method of preparing an antibody capable of binding insulin growth factor I and insulin growth factor II, the method comprising expressing the nucleic acid of the present invention in a host cell under conditions to provide for expression of the nucleic acid, followed by recovery of the antibody.

A method of identifying a polypeptide ligand specific for human insulin growth factor I and insulin growth factor II is provided comprising: (a) providing a phage library comprising phage expressing candidate human insulin growth factor I and insulin growth factor I binding polypeptides; (b) contacting the phage library with human insulin growth factor I and insulin growth factor II protein; and (c) detecting binding of the human insulin growth factor I and insulin growth factor II protein to phage; thereby identifying a polypeptide ligand specific for human insulin growth factor I and insulin growth factor II.

A method for treating a neoplastic disease in a mammalian subject is provided comprising administering to the mammal subject a pharmaceutical composition comprising an antibody with an amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8, which specifically binds to an insulin-like growth factor I in an amount effective to reduce or eliminate the neoplastic disease in the mammalian subject. In one aspect, the antibody specifically binds to insulin-like growth factor I and insulin-like growth factor II. In a further aspect, the antibody comprises an amino acid sequence of SEQ ID NO: 5, SEQ ID NO: 6, SEQ ID NO: 7, or SEQ ID NO: 8. The antibody can be linked to a cytotoxic agent. The cytotoxic agent can be a cytotoxic drug or a radioactive isotope. In a detailed aspect, the neoplastic disease is a solid tumor, hematological malignancy, leukemia, colorectal cancer, benign or malignant breast cancer, uterine cancer, uterine leiomyomas, ovarian cancer, endometrial cancer, polycystic ovary syndrome, endometrial polyps, prostate cancer, prostatic hypertrophy, pituitary cancer, adenomyosis, adenocarcinomas, meningioma, melanoma, bone cancer, multiple myeloma, CNS cancer, glioma, or astroblastoma. In a further detailed aspect, the neoplastic disease is tumor cell metastasis in the mammalian subject. The neoplastic disease can be breast cancer metastasis in the mammalian subject.

A method of diagnosing cancer in a mammalian subject suspected of having neoplastic disease or suspected of being at risk for neoplastic disease is provided comprising, obtaining a test sample from blood or tissue of the subject, the test sample comprising a cell population, providing an antibody comprising an amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8 to detect the presence or absence of an IGF-I marker on the cells within the cell population, analyzing the cell population detected by the IGF-I marker to identify and characterize the cells, the presence of IGF-I marker on or in the cells indicative of neoplastic disease or risk of neoplastic disease in the mammalian subject.

The method of diagnosing cancer further comprises providing an antibody comprising an amino acid sequence of SEQ ID NO: 5, SEQ ID NO: 6, SEQ ID NO: 7 or SEQ ID NO: 8 to detect the presence or absence of an IGF-II marker and the IGF-I marker on or in the cells within the cell population, and analyzing the cell population detected by the IGF-I marker and the IGF-II marker to identify and characterize the cells, the presence of the IGF-I marker and the IGF-II marker on or in the cells indicative of neoplastic disease or risk of neoplastic disease in the mammalian subject.

In the diagnostic method, the presence of IGF-I marker or IGF-II marker on or in the cells in the specimen indicates the presence of metastatic cancer in the mammalian subject. In the diagnostic method, the presence of IGF-I marker or IGF-II marker on or in the cells in the specimen indicates the presence of early stage cancer in the mammalian subject. In the diagnostic method, the absence of IGF-I marker and IGF-II marker on or in the cells in the specimen indicates presence of a disease free state or a non-measurable disease state in the mammalian subject. In a further aspect of the diagnostic method, the presence or absence of IGF-I marker or IGF-II marker on or in the cells in the specimen monitors therapy management during cancer therapy or cancer recovery. In a further aspect, the method comprises an imaging moiety associated with the antibody. The imaging moiety can be imaged through magnetic resonance spectroscopy, X-ray spectroscopy, or positron emission tomography (PET). The association can be a covalent bond or a non-covalent bond. The neoplastic disease includes, but is not limited to, solid tumor, hematological malignancy, leukemia, colorectal cancer, breast cancer, uterine cancer, uterine leiomyomas, ovarian cancer, endometrial cancer, polycystic ovary syndrome, endometrial polyps, prostate cancer, prostatic hypertrophy, pituitary cancer, adenomyosis, adenocarcinomas, meningioma, melanoma, bone cancer, multiple myeloma, CNS cancer, glioma, or astroblastoma.

A method of screening a drug candidate compound for treatment of cancer in a mammalian subject comprising administering a therapeutically effective amount of the drug candidate compound to the subject suspected of having cancer, obtaining test samples from blood or tissue of the subject before and after treatment with the drug candidate compound, the test samples comprising a cell population suspected of containing tumor cells, providing an antibody comprising an amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8 to detect the presence or absence of an IGF-I marker on the cells in the test sample, analyzing the cell population detected by the IGF-I marker to identify the tumor cells in the test samples before treatment with the drug candidate compound compared to after treatment with the drug candidate compound, wherein the presence of a decreased number of the tumor cells in the specimen after treatment compared to a number of the tumor cells in a specimen before treatment indicating effectiveness of the drug candidate compound in treating the cancer in the mammalian subject.

In another aspect, the method of screening a drug candidate compound for treatment of cancer in a mammalian subject comprises providing an antibody comprising an amino acid sequence of SEQ ID NO: 5, SEQ ID NO: 6, SEQ ID NO: 7, or SEQ ID NO: 8 to detect the presence or absence of an IGF-II marker and the IGF-I marker on the cells in the test samples, and analyzing the cell population detected by the IGF-I marker and IGF-II marker to identify the tumor cells in the test samples before treatment with the drug candidate compound compared to after treatment with the drug candidate compound, wherein the presence of a decreased number of the tumor cells in the specimen after treatment compared to a number of the tumor cells in a specimen before treatment indicating effectiveness of the drug candidate compound in treating the cancer in the mammalian subject. The cancer can be metastatic cancer or early stage cancer.

DETAILED DESCRIPTION

Figure 1B:
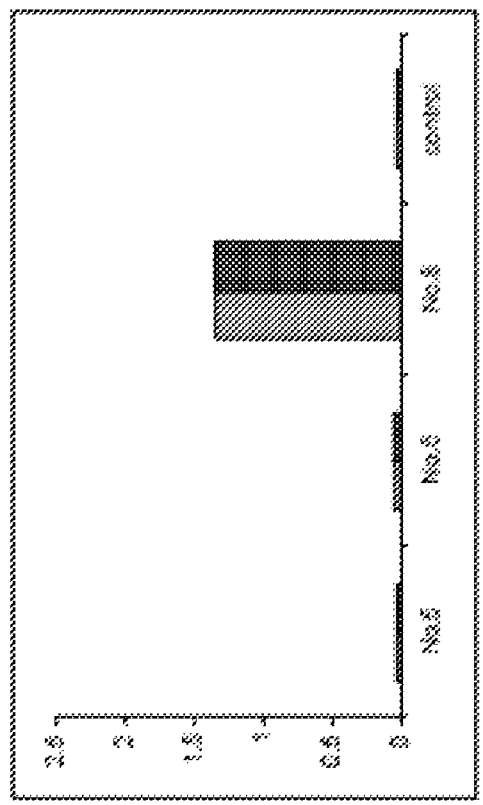
FIG. 1A and 1B are bar graphs illustrating that human monoclonal antibodies selected against IGF-I that bind to IGF-I or IGF-I and IGF-II. m705 (No. 5) and m706 (No. 6) react with IGF-I and not with IGF-II. m708 (No. 8) cross reacts with IGF-I and IGF-II.

The present invention is generally related to antibody compositions and methods for treatment of neoplastic disease in a mammalian subject. The present invention further relates to methods of diagnosing neoplastic disease in a mammalian subject. The antibody compositions are isolated monoclonal antibodies that bind to insulin-like growth factor I. Another set of antibody compositions are monoclonal antibodies that bind to insulin-like growth factor I and are cross-reactive to and bind to insulin-like growth factor II. The isolated monoclonal antibodies are, for example, human, non-human primate, rabbit, rat or mouse antibodies. The isolated human monoclonal antibody compositions that bind to insulin-like growth factor I are, for example, m705 and m706. The isolated human monoclonal antibody compositions that bind to both insulin-like growth factor I and insulin-like growth factor II are m708 and m708.2. Monoclonal antibodies m705, m706, m708, and m708.2 do not bind to human insulin.

The insulin-like growth factors (IGF) are mitogens that play a role in regulating cell proliferation, differentiation, and apoptosis. The effects of IGFs are mediated through the insulin-like growth factor receptor, IGF-1R. Insulin-like growth factor I (IGF-I) and insulin-like growth factor II (IGF-II) mediate an effect through binding to type I insulin-like growth factor receptor (IGF-1R). IGF-1R is overexpressed by many tumors and mediates proliferation, motility and protection from apoptosis. Its major ligand which is overexpressed by tumors is IGF-I. Inhibition of the IGF-1R-mediated signaling can occur at extracellular or intracellular targets.

Extracellular IGFs bind to the IGF-IR and the activated tyrosine kinase leads to enhanced proliferation and cell survival mediated by signaling pathways that include PI3 kinase/Akt and the MAPK pathways. Inhibition of the IGF-IR may occur at multiple levels both extracellular and intracellular. LeRoith D, Helman L, *Cancer Cell* 5: 201-202, 2004.

Prevention of binding of IGF-I to its receptor can lead to inhibition of signal transduction that is required for cell proliferation. By screening an antibody human naïve phage library, two antibodies, m705 and m706, have been identified that are specific for IGF-I and do not cross-react with IGF-II and insulin. Two antibodies, m708 and m708.2, are cross reactive with IGF-I and IGF-II. M708 shows the highest affinity binding to IGF-I and was converted to IgG1. All antibodies showed competition with the receptor (IGF-1R) binding of IGF-I and IGF-II. The IgG1 m708 potently inhibited signal transduction mediated by IGF-1R in the MCF-7 breast cancer cell line with an $IC_{50}$ equal to 1 nM. The mechanism of inhibition occurs by outcompeting the IGF-1R for binding to IGF-II. This is in agreement with its high nM range affinity to IGF-I. These antibodies are useful for both therapeutic treatment for cancer and diagnostic assays related to cancer therapy.

It is to be understood that this invention is not limited to particular methods, reagents, compounds, compositions or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a cell" includes a combination of two or more cells, and the like.

The term "about" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

"Patient", "subject" or "mammal" are used interchangeably and refer to mammals such as human patients and non-human primates, as well as experimental animals such as rabbits, rats, and mice, and other animals. Animals include all vertebrates, e.g., mammals and non-mammals, such as sheep, dogs, cows, chickens, amphibians, and reptiles.

"Treating" or "treatment" includes the administration of the antibody compositions, compounds or agents of the present invention to prevent or delay the onset of the symptoms, complications, or biochemical indicia of a disease, alleviating the symptoms or arresting or inhibiting further development of the disease, condition, or disorder (e.g., cancer, metastatic cancer, or metastatic breast cancer). Treatment can be prophylactic (to prevent or delay the onset of the disease, or to prevent the manifestation of clinical or subclinical symptoms thereof) or therapeutic suppression or alleviation of symptoms after the manifestation of the disease.

"Cancer" or "malignancy" are used as synonymous terms and refer to any of a number of diseases that are characterized by uncontrolled, abnormal proliferation of cells, the ability of affected cells to spread locally or through the bloodstream and lymphatic system to other parts of the body (i.e., metastasize) as well as any of a number of characteristic structural and/or molecular features. A "cancerous" or "malignant cell" is understood as a cell having specific structural properties, lacking differentiation and being capable of invasion and metastasis. Examples of cancers are, breast, lung, brain, bone, liver, kidney, colon, and prostate cancer. (see DeVita et al., Eds., *Cancer Principles and Practice of Oncology*, 6th. Ed., Lippincott Williams & Wilkins, Philadelphia, Pa., 2001; this reference is herein incorporated by reference in its entirety for all purposes).

"Cancer-associated" refers to the relationship of a nucleic acid and its expression, or lack thereof, or a protein and its level or activity, or lack thereof, to the onset of malignancy in a subject cell. For example, cancer can be associated with expression of a particular gene that is not expressed, or is expressed at a lower level, in a normal healthy cell. Conversely, a cancer-associated gene can be one that is not expressed in a malignant cell (or in a cell undergoing transformation), or is expressed at a lower level in the malignant cell than it is expressed in a normal healthy cell.

In the context of the cancer, the term "transformation" refers to the change that a normal cell undergoes as it becomes malignant. In eukaryotes, the term "transformation" can be used to describe the conversion of normal cells to malignant cells in cell culture.

"Proliferating cells" are those which are actively undergoing cell division and growing exponentially. "Loss of cell proliferation control" refers to the property of cells that have lost the cell cycle controls that normally ensure appropriate restriction of cell division. Cells that have lost such controls proliferate at a faster than normal rate, without stimulatory signals, and do not respond to inhibitory signals.

"Advanced cancer" means cancer that is no longer localized to the primary tumor site, or a cancer that is Stage III or IV according to the American Joint Committee on Cancer (AJCC).

"Well tolerated" refers to the absence of adverse changes in health status that occur as a result of the treatment and would affect treatment decisions.

"Metastatic" refers to tumor cells, e.g., human breast cancer cells, that are able to establish secondary tumor lesions in the lungs, liver, bone or brain of immune deficient mice upon injection into the mammary fat pad and/or the circulation of the immune deficient mouse.

"Non-metastatic" refers to tumor cells, e.g., human breast cancer cells, that are unable to establish secondary tumor lesions in the lungs, liver, bone or brain or other target organs of breast cancer metastasis in immune deficient mice upon injection into the mammary fat pad and/or the circulation. The human tumor cells used herein and addressed herein as non-metastatic are able to establish primary tumors upon injection into the mammary fat pad of the immune deficient mouse, but they are unable to disseminate from those primary tumors.

"Lymphocyte" as used herein has the normal meaning in the art, and refers to any of the mononuclear, nonphagocytic leukocytes, found in the blood, lymph, and lymphoid tissues, e.g., B and T lymphocytes.

"Polypeptide fragment" as used herein refers to a polypeptide that has an amino-terminal and/or carboxy-terminal deletion, but where the remaining amino acid sequence is identical to the corresponding positions in the naturally-occurring sequence deduced, for example, from a full-length cDNA sequence. Fragments typically are at least 5, 6, 8 or 10 amino acids long, preferably at least 14 amino acids long, more preferably at least 20 amino acids long, usually at least 50 amino acids long, and even more preferably at least 70 amino acids long. The term "analog" as used herein refers to polypeptides which are comprised of a segment of at least 25 amino acids that has substantial identity to a portion of a deduced amino acid sequence and which has at least one of the following properties: (1) specific binding to IGF-I or IGF-II, under suitable binding conditions, (2) ability to block IGF-I or IGF-II binding to IGF-1 receptor, or (3) ability to inhibit IGF-I expressing or IGF-II expressing cell growth in vitro or in vivo. Typically, polypeptide analogs comprise a conservative amino acid substitution (or addition or deletion) with respect to the naturally-occurring sequence. Analogs typically are at least 20 amino acids long, preferably at least 50 amino acids long or longer, and can often be as long as a full-length naturally-occurring polypeptide.

Peptide analogs are commonly used in the pharmaceutical industry as non-peptide drugs with properties analogous to those of the template peptide. These types of non-peptide compound are termed "peptide mimetics" or "peptidomimetics". Fauchere, *J. Adv. Drug Res.* 15: 29, 1986; Veber and Freidinger *TINS* p. 392 (1985); and Evans et al. *J. Med. Chem.* 30: 1229, 1987, which are incorporated herein by reference. Such compounds are often developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from the group consisting of: —CH$_2$NH—, —CH$_2$S—, —CH$_2$—CH$_2$—, —CH=CH-(cis and trans), —COCH$_2$—, —CH(OH)CH$_2$—, and —CH$_2$SO—, by methods well known in the art. Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch *Ann. Rev. Biochem.* 61: 387, 1992, incorporated herein by reference); for example, by adding internal cysteine residues capable of forming intramolecular disulfide bridges which cyclize the peptide.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity. Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleuci-ne, phenylalanine-tyrosine, lysine-arginine, alanine-valine, glutamic-aspartic, and asparagine-glutamine.

As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99% homology. In particular, conservative amino acid replacements are contemplated. Conservative amino acid replacement does not against the overall homology which can be maintained at least 75%, more preferably at least 80%, 90%, 95%, and most preferably 99% homology. Conservative replacements are those that take place within a family of amino acids that are related in their side chains. Genetically encoded amino acids are generally divided into families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. *Science* 253: 164, 1991. Thus, the foregoing examples demonstrate that those of skill in the art can recognize sequence motifs and structural conformations that may be used to define structural and functional domains in accordance with the invention.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W.H. Freeman and Company, New York (1984)); Introduction to Protein Structure (C. Branden and J. Tooze, eds., Garland Publishing, New York, N.Y. (1991)); and Thornton et al. *Nature* 354: 105, 1991, which are each incorporated herein by reference.

"Antibody" or "antibody peptide(s)" refer to an intact antibody, or a binding fragment thereof that competes with the intact antibody for specific binding. Binding fragments are produced by recombinant DNA techniques, or by enzymatic or chemical cleavage of intact antibodies. Binding fragments include Fab, Fab', F(ab')$_2$, Fv, and single-chain antibodies. An intact "antibody" comprises at least two heavy (H) chains and two light (L) chains inter-connected by disulfide bonds. Each heavy chain is comprised of a heavy chain variable region (abbreviated herein as HCVR or VH) and a heavy chain constant region. The heavy chain constant region is comprised of three domains, $CH_1$, $CH_2$ and $CH_3$. Each light chain is comprised of a light chain variable region (abbreviated herein as LCVR or $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxyl-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (Clq) of the classical complement system. The term antibody includes antigen-binding portions of an intact antibody that retain capacity to bind IGF-I or IGF-II. Examples of binding include (i) a Fab fragment, a monovalent fragment consisting of the $V_L$, $V_H$, $C_L$ and CH1 domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb fragment (Ward et al., *Nature* 341: 544-546, 1989), which consists of a $V_H$ domain; and (vi) an isolated complementarity determining region (CDR).

An antibody other than a "bispecific" or "bifunctional" antibody is understood to have each of its binding sites identical. An antibody substantially inhibits adhesion of a receptor to a counterreceptor when an excess of antibody reduces the quantity of receptor bound to counterreceptor by at least about 20%, 40%, 60% or 80%, and more usually greater than about 85% (as measured in an in vitro competitive binding assay).

"Fab antibodies" or "Fab fragments" refers to antibody fragments lacking all or part of an immunoglobulin constant region, and containing the Fab regions of the antibodies. Fab antibodies are prepared as described herein.

"Single chain antibodies" or "single chain Fv (scFv)" refers to an antibody fusion molecule of the two domains of the Fv fragment, $V_L$ and $V_H$. Although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see, e.g., Bird et al., *Science* 242: 423-426, 1988; and Huston et al., *Proc. Natl. Acad. Sci. USA,* 85: 5879-5883, 1988). Such single chain antibodies are included by reference to the term "antibody" fragments can be prepared by recombinant techniques or enzymatic or chemical cleavage of intact antibodies.

"Human sequence antibody" includes antibodies having variable and constant regions (if present) derived from human germline immunoglobulin sequences. The human sequence antibodies of the invention can include amino acid residues not encoded by human germline immunoglobulin sequences (e.g., mutations introduced by random or site-specific mutagenesis in vitro or by somatic mutation in vivo). Such antibodies can be generated in non-human transgenic animals, e.g., as described in PCT Publication Nos. WO 01/14424 and WO 00/37504. However, the term "human sequence antibody", as used herein, is not intended to include antibodies in which CDR sequences derived from the germline of another mammalian species, such as a mouse, have been grafted onto human framework sequences (e.g., humanized antibodies).

Also, recombinant immunoglobulins may be produced. See, Cabilly, U.S. Pat. No. 4,816,567, incorporated herein by reference in its entirety and for all purposes; and Queen et al., *Proc. Nat'l Acad. Sci. USA* 86: 10029-10033, 1989.

"Monoclonal antibody" refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions (if present) derived from human germline immunoglobulin sequences. In one embodiment, the human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

"Polyclonal antibody" refers to a preparation of more than 1 (two or more) different antibodies to a cell surface receptor or a ligand, e.g., IGF-I or IGF-II binding to IGF-1 receptor. Such a preparation includes antibodies binding to a range of different epitopes. Antibodies to IGF-I or IGF-II can bind to an epitope on IGF-I or IGF-II so as to inhibit IGF-I or IGF-II binding to IGF-1 receptor. Similarly antibodies to IGF-I or IGF-II can act as peptidomimetics that bind to IGF-1 receptor and thus inhibit IGF-I or IGF-II binding to IGF-1 receptor. These and other antibodies suitable for use in the present invention can be prepared according to methods that are well known in the art and/or are described in the references cited here. In preferred embodiments, anti-IGF-I or anti-IGF-II antibodies used in the invention are "human antibodies"—e.g., antibodies isolated from a human—or they are "human sequence antibodies" (defined supra).

"Immune cell response" refers to the response of immune system cells to external or internal stimuli (e.g., antigen, cell surface receptors, IGF-I, IGF-IIT, IGF-1 receptor, cytokines, chemokines, and other cells) producing biochemical changes in the immune cells that result in immune cell migration, killing of target cells, phagocytosis, production of antibodies, other soluble effectors of the immune response, and the like.

"Immune response" refers to the concerted action of lymphocytes, antigen presenting cells, phagocytic cells, granulocytes, and soluble macromolecules produced by the above cells or the liver (including antibodies, cytokines, and complement) that results in selective damage to, destruction of, or elimination from the human body of cancerous cells, metastatic tumor cells, metastatic breast cancer cells, invading pathogens, cells or tissues infected with pathogens, or, in cases of autoimmunity or pathological inflammation, normal human cells or tissues.

"T lymphocyte response" and "T lymphocyte activity" are used here interchangeably to refer to the component of immune response dependent on T lymphocytes (e.g., the proliferation and/or differentiation of T lymphocytes into helper, cytotoxic killer, or suppressor T lymphocytes, the provision of signals by helper T lymphocytes to B lymphocytes that cause or prevent antibody production, the killing of specific target cells by cytotoxic T lymphocytes, and the release of soluble factors such as cytokines that modulate the function of other immune cells).

Cancer Treatment

Blockade of IGF-I or IGF-II binding to IGF-1 receptor by antibody compositions can enhance the memory or secondary immune response to cancerous cells in the patient. Antibodies to IGF-I or IGF-II can be combined with an immunogenic agent, such as cancerous cells, purified tumor antigens (including recombinant proteins, peptides, and carbohydrate molecules), cells, and cells transfected with genes encoding immune stimulating cytokines and cell surface antigens, or used alone, to stimulate immunity.

Antibodies to IGF-I or IGF-II is effective when following a vaccination protocol. Many experimental strategies for vaccination against tumors have been devised (see Rosenberg, *ASCO Educational Book Spring:* 60-62, 2000; Logothetis, *ASCO Educational Book Spring:* 300-302, 2000; Khayat, *ASCO Educational Book Spring:* 414-428, 2000; Foon, *ASCO Educational Book Spring:* 730-738, 2000; see also Restifo et al., *Cancer: Principles and Practice of Oncology*, 61: 3023-3043, 1997. In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination. Dranoff et al., *Proc. Natl. Acad. Sci. U.S.A.*, 90: 3539-43, 1993.

Antibodies to IGF-I or IGF-II can boost GMCSF-modified tumor cell vaccines improves efficacy of vaccines in a number of experimental tumor models such as mammary carcinoma (Hurwitz et al., 1998, supra), primary prostate cancer (Hurwitz et al., *Cancer Research*, 60: 2444-8, 2000) and melanoma (van Elsas et al., *J. Exp. Med.*, 190: 355-66, 1999). In these instances, non-immunogenic tumors, such as the B 16 melanoma, have been rendered susceptible to destruction by the immune system. The tumor cell vaccine can also be modified to express other immune activators such as IL2, and costimulatory molecules, among others.

"Antineoplastic agent" is used herein to refer to agents that have the functional property of inhibiting a development or progression of a neoplasm in a human, particularly a malignant (cancerous) lesion, such as a carcinoma, sarcoma, lymphoma, or leukemia. Inhibition of metastasis is frequently a property of antineoplastic agents.

A "solid tumor" includes, but is not limited to, sarcoma, melanoma, carcinoma, or other solid tumor cancer.

"Sarcoma" refers to a tumor which is made up of a substance like the embryonic connective tissue and is generally composed of closely packed cells embedded in a fibrillar or homogeneous substance. Sarcomas include, but are not limited to, chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

"Melanoma" refers to a tumor arising from the melanocytic system of the skin and other organs. Melanomas include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

"Carcinoma" refers to a malignant new growth made up of epithelial cells tending to infiltrate the surrounding tissues and give rise to metastases. Exemplary carcinomas include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidernoid carcinoma, carcinoma mucosum, mucous carcinoma, carcinoma myxomatodes, naspharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma viflosum.

"Leukemia" refers to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease—acute or chronic; (2) the type of cell involved; myeloid (myelogenous), lymphoid (lymphogenous), or monocytic; and (3) the increase or non-increase in the number of abnormal cells in the blood—leukemic or aleukemic (subleukemic). Leukemia includes, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

Additional cancers include, for example, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, cervical cancer, endometrial cancer, adrenal cortical cancer, and prostate cancer.

Antibody Structure

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)) (incorporated by reference in its entirety for all purposes). The variable regions of each light/heavy chain pair form the antibody binding site.

Thus, an intact IgG antibody has two binding sites. Except in bifunctional or bispecific antibodies, the two binding sites are the same.

The chains all exhibit the same general structure of relatively conserved framework regions (FR) joined by three hyper variable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat Sequences of Proteins of Immunological Interest (National Institutes of Health, Bethesda, Md. (1987 and 1991)), or Chothia & Lesk *J. Mol. Biol.* 196: 901-917, 1987; Chothia et al., *Nature* 342: 878-883, 1989.

A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai and Lachmann, *Clin. Exp. Immunol.* 79: 315-321, 1990, Kostelny et al., *J. Immunol.* 148: 1547-1553, 1992. In addition, bispecific antibodies may be formed as "diabodies" (Holliger et al., *PNAS USA* 90: 6444-6448, 1993 or "Janusins" (Traunecker et al., *EMBO J.* 10: 3655-3659, 1991 and Traunecker et al., *Int J Cancer* 7:51-52, 1992). Production of bispecific antibodies can be a relatively labor intensive process compared with production of conventional antibodies and yields and degree of purity are generally lower for bispecific antibodies. Bispecific antibodies do not exist in the form of fragments having a single binding site (e.g., Fab, Fab', and Fv).

FAB or scFV Phage Libraries

An approach for a phage display library to identify an antibody composition that specifically binds to a ligand or a cell surface receptor on a metastatic cell, for example, IGF-I, IGF-II, or IGF-1 receptor, has been the use of Fab or single-chain Fv (scFv) phage-libraries. See, e.g., Huston et al., *Proc. Natl. Acad. Sci. U.S.A.*, 85: 5879-5883, 1988; Chaudhary et al., *Proc. Natl. Acad. Sci. U.S.A.*, 87: 1066-1070, 1990; Zhang et al., *J. Virol.* 78: 9233-9242, 2004. Various embodiments of Fab or scFv libraries displayed on bacteriophage coat proteins have been described. Refinements of phage display approaches are also known, for example as described in WO96/06213 and WO92/01047 (Medical Research Council et al.) and WO97/08320 (Morphosys), which are incorporated herein by reference. The display of Fab libraries is known, for instance as described in WO92/01047 (CAT/MRC) and WO91/17271 (Affymax).

Hybrid antibodies or hybrid antibody fragments that are cloned into a display vector can be selected against the appropriate antigen associated with a metastatic cell, e.g., a cell surface receptor or ligand to a cell surface receptor on a metastatic tumor cell, in order to identify variants that maintained good binding activity because the antibody or antibody fragment will be present on the surface of the phage or phagemid particle. See for example Barbas III et al., *Phage Display, A Laboratory Manual*, Cold Spring Harbor Laboratory Press, Cold Spring Harbor, N.Y., 2001, the contents of which are incorporated herein by reference. For example, in the case of Fab fragments, the light chain and heavy chain Fd products are under the control of a lac promoter, and each chain has a leader signal fused to it in order to be directed to the periplasmic space of the bacterial host. It is in this space that the antibody fragments will be able to properly assemble. The heavy chain fragments are expressed as a fusion with a phage coat protein domain which allows the assembled antibody fragment to be incorporated into the coat of a newly made phage or phagemid particle. Generation of new phagemid particles requires the addition of helper phage which contain all the necessary phage genes. Once a library of antibody fragments is presented on the phage or phagemid surface, a process termed panning follows. This is a method whereby i) the antibodies displayed on the surface of phage or phagemid particles are bound to the desired antigen, ii) non-binders are washed away, iii) bound particles are eluted from the antigen, and iv) eluted particles are exposed to fresh bacterial hosts in order to amplify the enriched pool for an additional round of selection. Typically three or four rounds of panning are performed prior to screening antibody clones for specific binding. In this way phage/phagemid particles allow the linkage of binding phenotype (antibody) with the genotype (DNA) making the use of antibody display technology very successful. However, other vector formats could be used for this humanization process, such as cloning the antibody fragment library into a lytic phage vector (modified T7 or Lambda Zap systems) for selection and/or screening.

After selection of desired hybrid antibodies and/or hybrid antibody fragments, it is contemplated that they can be produced in large volume by any technique known to those skilled in the art, e.g., prokaryotic or eukaryotic cell expression and the like. For example, hybrid antibodies or fragments may be produced by using conventional techniques to construct an expression vector that encodes an antibody heavy chain in which the CDRs and, if necessary, a minimal portion of the variable region framework, that are required to retain original species antibody binding specificity (as engineered according to the techniques described herein) are derived from the originating species antibody and the remainder of the antibody is derived from a target species immunoglobulin which may be manipulated as described herein, thereby producing a vector for the expression of a hybrid antibody heavy chain.

In a detailed embodiment, a Fab or single-chain Fv (scFv) antibody library can be prepared from the peripheral blood lymphocytes of 5, 10, 15, or 20 or more patients with various cancer diseases. Completely human high-affinity Fab or scFv antibodies can then be selected by using synthetic sialyl Lewis$^x$ and Lewis$^x$ BSA conjugates. In one study, these human scFv antibodies were specific for sialyl Lewis$^x$ and Lewis$^x$, as demonstrated by ELISA, BIAcore, and flow cytometry binding to the cell surface of pancreatic adenocarcinoma cells. Nucleotide sequencing revealed that at least four unique scFv genes were obtained. The $K_d$ values ranged from 1.1 to $6.2 \times 10^{-7}$ M that were comparable to the affinities of mAbs derived from the secondary immune response. These antibodies could be valuable reagents for probing the structure and function of carbohydrate antigens and in the treatment of human tumor diseases. Mao et al., Proc. Natl. Acad. Sci. U.S.A. 96: 6953-6958, 1999.

In a further detailed embodiment, phage displayed combinatorial antibody libraries can be used to generate and select a wide variety of antibodies to an appropriate antigen associated with a metastatic cell, e.g., a cell surface receptor or a ligand to a cell surface receptor on a metastatic tumor cell. The phage coat proteins pVII and pIX can be used to display the heterodimeric structure of the antibody Fv region. Aspects of this technology have been extended to construct a large, human Fab or single-chain Fv (scFv) library of $4.5 \times 10^9$ members displayed on pIX of filamentous bacteriophage. Furthermore, the diversity, quality, and utility of the library were demonstrated by the selection of Fab or scFv clones against six different protein antigens. Notably, more than 90% of the selected clones showed positive binding for their respective antigens after as few as three rounds of panning. Analyzed Fabs or scFvs were also found to be of high affinity. For example, kinetic analysis (BIAcore) revealed that Fabs or scFvs against staphylococcal enterotoxin B and cholera toxin B subunit had a nanomolar and subnanomolar dissociation constant, respectively, affording affinities comparable to, or exceeding that, of mAbs obtained from immunization. High specificity was also attained, not only between very distinct proteins, but also in the case of more closely related proteins, e.g., Ricinus communis ("ricin") agglutinins ($RCA_{60}$ and $RCA_{120}$), despite >80% sequence homology between the two. The results suggested that the performance of pIX-display libraries can potentially exceed that of the pIII-display format and make it ideally suited for panning a wide variety of target antigens. Gao et al, Proc. Natl. Acad. Sci. U.S.A. 99: 12612-12616, 2001.

Specific binding between an antibody or other binding agent and an antigen means a binding affinity of at least $10^{-6}$ M. Preferred binding agents bind with affinities of at least about $10^{-7}$ M, and preferably $10^{-8}$ M to $10^{-9}$ M, $10^{-10}$ M, $10^{-11}$ M, or $10^{-12}$ M. The term epitope means an antigenic determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

"Epitope" refers to that portion of any molecule capable of being recognized by and bound by an antibody or T-cell receptor at one or more of the antibody's or T cell receptor's antigen binding region. Epitopes usually consist of chemically active surface groupings of molecules such as amino acids or sugar side chains and have specific three dimensional structural characteristics as well as specific charge characteristics. By "inhibiting and/or neutralizing epitope" is intended an epitope, which, when bound by an antibody, results in loss of biological activity of the molecule or organism containing the epitope, in vivo, in vitro or in situ, more preferably in vivo, including binding of IGF-I or IGF-II to an IGF-1 receptor. An antibody is said to specifically bind an antigen when the dissociation constant is less than 1 µM, preferably less than 100 nM and most preferably less than 10 nM. Conformational and nonconformational epitopes are distinguished in that the binding to the former but not the latter is lost in the presence of denaturing solvents.

Epitopes recognized by antibodies, and fragments and regions thereof, of the present invention can include 5 or more amino acids comprising at least one amino acid of each or both of the following amino acid sequences of IGF-I or IGF-IIT, which provide a topographical or three dimensional epitope of IGF-I or IGF-II which is recognized by, and/or binds with anti-IGF-I or IGF-II activity, an antibody, and fragments, and variable regions thereof, of the present invention: Screening Methods for determining IGF-I or IGF-II neutralizing and/or inhibiting activity are also provided in the present invention. In the context of the present invention, anti-IGF-I or anti-IGF-II neutralizing activity or IGF-I or IGF-II inhibiting activity refers to the ability of an IGF-I or IGF-II neutralizing compound to block at least one biological activity of IGF-I or IGF-II, such as preventing IGF-I or IGF-II from binding to a IGF-1 receptor, blocking production of IGF-I or IGF-II by intracellular processing, such as transcription, translation or post-translational modification, expression on the cell surface, secretion or assembly of the bioactive IGF-I or IGF-II. Additionally, IGF-I or IGF-II neutralizing compounds can act by inducing regulation of metabolic pathways such as those involving the up or down regulation of IGF-I or IGF-II production. Alternatively IGF-I or IGF-II neutralizing compounds can modulate cellular sensitivity to IGF-I or IGF-II by decreasing such sensitivity. IGF-I or IGF-II neutralizing compounds can be selected from the group consisting of antibodies, or fragments or portions thereof, peptides, peptido mimetic compounds or organo mimetic compounds that neutralizes IGF-I or IGF-II activity in vitro, in situ or in vivo is considered a IGF-I or IGF-II neutralizing compound If used according to the present invention. Screening methods which can be used to determine IGF-I or IGF-II neutralizing activity of a IGF-I or IGF-II neutralizing compound can include in vitro or in vivo assays. Such in vitro assays can include an assay for (i) inhibition of IGF-1 receptor phosphorylation in an in vitro MCF-7 breast cancer cell assay at an antibody concentration about 4 nM or greater; (ii) inhibition of IGF-I binding or IGF-II binding to IGF-1 receptor; or (iii) inhibition of cell migration in a cell migration assay. Alternatively or additionally, in vivo testing of IGF-I or IGF-II neutralizing activity of IGF-I or IGF-I neutralizing compounds can be tested using an in vitro assay for inhibition of IGF-1 receptor phosphorylation in an in vitro MCF-7 breast cancer cell assay at an antibody concentration about 4 nM or greater, as described herein.

"Neutralizing" refers to an antibody that inhibits IGF-I or IGF-II activity by preventing the binding of human IGF-I or IGF-II to its specific receptor, IGF-1R, or by inhibiting the signaling of IGF-I or IGF-II through its receptor, should binding occur. A mAb is neutralizing if it is 90% effective, preferably 95% effective and most preferably 100% effective in inhibiting IGF-I or IGF-II activity, for example, as measured in the phosphorylation assay of MCF-7 breast cancer cells.

"Agent" is used herein to denote a chemical compound, a mixture of chemical compounds, a biological macromolecule, or an extract made from biological materials.

"Altered antibody" refers to a protein encoded by an altered immunoglobulin coding region, which may be obtained by expression in a selected host cell. Such altered antibodies are engineered antibodies (e.g., chimeric or humanized antibodies) or antibody fragments lacking all or part of an immunoglobulin constant region, e.g., Fv, Fab, or F(ab)$_2$ and the like.

"Altered immunoglobulin coding region" refers to a nucleic acid sequence encoding altered antibody of the invention. When the altered antibody is a CDR-grafted or humanized antibody, the sequences that encode the complementarity determining regions (CDRs) from a non-human immunoglobulin are inserted into a first immunoglobulin partner comprising human variable framework sequences. Optionally, the first immunoglobulin partner is operatively linked to a second immunoglobulin partner.

"High affinity" refers to an antibody having a binding affinity characterized by a K$_d$ equal to or less than 3.5×10$^{-11}$ M for human IGF-I or IGF-II as determined by surface plasmon resonance.

By "binding specificity for human IGF-I or IGF-II" is meant a high affinity for human IGF-I or human IGF-II. Monoclonal antibodies m705 and m706 have a high binding specificity for human IGF-I, and do not bind to human insulin. Monoclonal antibodies m708 and m708.2 have a high binding specificity for human IGF-I and human IGF-II, and do not bind to human insulin.

The terms Fv, Fc, Fd, Fab, or F(ab)$_2$ are used with their standard meanings (see, e.g., Harlow et al., Antibodies A Laboratory Manual, Cold Spring Harbor Laboratory, (1988)).

"Engineered antibody" describes a type of altered antibody, i.e. a full-length synthetic antibody (e.g., a chimeric or humanized antibody as opposed to an antibody fragment) in which a portion of the light and/or heavy chain variable domains of a selected acceptor antibody are replaced by analogous parts from one or more donor antibodies which have specificity for the selected epitope. For example, such molecules may include antibodies characterized by a humanized heavy chain associated with an unmodified light chain (or chimeric light chain), or vice versa. Engineered antibodies may also be characterized by alteration of the nucleic acid sequences encoding the acceptor antibody light and/or heavy variable domain framework regions in order to retain donor antibody binding specificity. These antibodies can comprise replacement of one or more CDRs (preferably all) from the acceptor antibody with CDRs from a donor antibody described herein.

A "chimeric antibody" refers to a type of engineered antibody which contains naturally-occurring variable region (light chain and heavy chains) derived from a donor antibody in association with light and heavy chain constant regions derived from an acceptor antibody.

A "humanized antibody" refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity. See, e.g., Queen et al., *Proc. Natl. Acad Sci USA*, 86: 10029-10032, 1989, Hodgson et al., *Bio/Technology*, 2: 421, 1991.

"Donor antibody" refers to an antibody (monoclonal, or recombinant) which contributes the nucleic acid sequences of its variable regions, CDRs, or other functional fragments or analogs thereof to a first immunoglobulin partner, so as to provide the altered immunoglobulin coding region and resulting expressed altered antibody with the antigenic specificity and neutralizing activity characteristic of the donor antibody.

"Acceptor antibody" refers to an antibody (monoclonal, or recombinant) heterologous to the donor antibody, which contributes all (or any portion, but preferably all) of the nucleic acid sequences encoding its heavy and/or light chain framework regions and/or its heavy and/or light chain constant regions to the first immunoglobulin partner. Preferably a human antibody is the acceptor antibody.

"CDRs" are defined as the complementarity determining region amino acid sequences of an antibody which are the hypervariable regions of immunoglobulin heavy and light chains. See, e.g., Kabat et al., Sequences of Proteins of Immunological Interest, 4th Ed., U.S. Department of Health and Human Services, National Institutes of Health (1987). There are three heavy chain and three light chain CDRs (or CDR regions) in the variable portion of an immunoglobulin. Thus, "CDRs" as used herein refers to all three heavy chain CDRs, or all three light chain CDRs (or both all heavy and all light chain CDRs, if appropriate).

CDRs provide the majority of contact residues for the binding of the antibody to the antigen or epitope. CDRs of interest in this invention are derived from donor antibody variable heavy and light chain sequences, and include analogs of the naturally occurring CDRs, which analogs also share or retain the same antigen binding specificity and/or neutralizing ability as the donor antibody from which they were derived.

By "sharing the antigen binding specificity or neutralizing ability" is meant, for example, that although mAb m705, m706, m708, or m708.2 may be characterized by a certain level of antigen affinity, a CDR encoded by a nucleic acid sequence of m705, m706, m708, or m708.2 in an appropriate structural environment may have a lower, or higher affinity. It is expected that CDRs of m705, m706, m708, or m708.2 in such environments will nevertheless recognize the same epitope(s) as the original monoclonal antibodies. Exemplary heavy chain CDRs include SEQ ID NO: 1; SEQ ID NO: 3; SEQ ID NO: 5; SEQ ID NO: 7, and exemplary light chain CDRs include SEQ ID NO: 2; SEQ ID NO: 4; SEQ ID NO: 6 and SEQ ID NO: 8. See, for example, Tables 1 and 2.

A "functional fragment" is a partial heavy or light chain variable sequence (e.g., minor deletions at the amino or carboxy terminus of the immunoglobulin variable region) which retains the same antigen binding specificity and/or neutralizing ability as the antibody from which the fragment was derived.

An "analog" is an amino acid sequence modified by at least one amino acid, wherein said modification can be chemical or a substitution or a rearrangement of a few amino acids (i.e., no more than 10), which modification permits the amino acid sequence to retain the biological characteristics, e.g., antigen specificity and high affinity, of the unmodified sequence. For example, (silent) mutations can be constructed, via substitutions, when certain endonuclease restriction sites are created within or surrounding CDR-encoding regions.

Analogs may also arise as allelic variations. An "allelic variation or modification" is an alteration in the nucleic acid sequence encoding the amino acid or peptide sequences of the invention. Such variations or modifications may be due to degeneracy in the genetic code or may be deliberately engineered to provide desired characteristics. These variations or modifications may or may not result in alterations in any encoded amino acid sequence.

"Carrier agents" or "effector agents" refers to non-protein carrier molecules to which the altered antibodies, and/or natural or synthetic light or heavy chains of the donor antibody or other fragments of the donor antibody may be associated by conventional means. Such non-protein carriers can include conventional carriers used in the diagnostic field, e.g., polystyrene or other plastic beads, polysaccharides, e.g., as used in the BIAcore® [Pharmacia] system, or other non-protein substances useful in the medical field and safe for administration to humans and animals. Other effector agents may include a macrocycle, for chelating a heavy metal atom, or radioisotopes. Such effector agents may also be useful to increase the half-life of the altered antibodies, e.g., polyethylene glycol.

Components of an immune response can be detected in vitro by various methods that are well known to those of ordinary skill in the art. For example, (1) cytotoxic T lymphocytes can be incubated with radioactively labeled target cells and the lysis of these target cells detected by the release of radioactivity; (2) helper T lymphocytes can be incubated with antigens and antigen presenting cells and the synthesis and secretion of cytokines measured by standard methods (Windhagen et al., *Immunity*, 2: 373-80, 1995); (3) antigen presenting cells can be incubated with whole protein antigen and the presentation of that antigen on MHC detected by either T lymphocyte activation assays or biophysical methods (Harding et al., *Proc. Natl. Acad. Sci.*, 86: 4230-4, 1989); (4) mast cells can be incubated with reagents that cross-link their Fc-epsilon receptors and histamine release measured by enzyme immunoassay (Siraganian et al., *TIPS*, 4: 432-437, 1983).

Similarly, products of an immune response in either a model organism (e.g., mouse) or a human patient can also be detected by various methods that are well known to those of ordinary skill in the art. For example, (1) the production of antibodies in response to vaccination can be readily detected by standard methods currently used in clinical laboratories, e.g., an ELISA; (2) the migration of immune cells to sites of inflammation can be detected by scratching the surface of skin and placing a sterile container to capture the migrating cells over scratch site (Peters et al., *Blood*, 72: 1310-5, 1988); (3) the proliferation of peripheral blood mononuclear cells in response to mitogens or mixed lymphocyte reaction can be measured using $^3$H-thymidine; (4) the phagocytic capacity of granulocytes, macrophages, and other phagocytes in PBMCs can be measured by placing PMBCs in wells together with labeled particles (Peters et al., *Blood*, 72: 1310-5, 1988); and (5) the differentiation of immune system cells can be measured by labeling PBMCs with antibodies to CD molecules such as CD4 and CD8 and measuring the fraction of the PBMCs expressing these markers.

For convenience, immune responses are often described in the present invention as being either "primary" or "secondary" immune responses. A primary immune response, which is also described as a "protective" immune response, refers to an immune response produced in an individual as a result of some initial exposure (e.g. the initial "immunization") to a particular antigen, e.g., cell surface receptor, ligand, IGF-I, IGF-II, or IGF-1 receptor. Such an immunization can occur, for example, as the result of some natural exposure to the antigen (for example, from initial infection by some pathogen that exhibits or presents the antigen) or from antigen presented by cancer cells of some tumor in the individual (for example, a metastatic breast cancer cell). Alternatively, the immunization can occur as a result of vaccinating the individual with a vaccine containing the antigen. For example, the vaccine can be a cancer vaccine comprising one or more antigens from a cancer cell e.g., a metastatic breast cancer cell.

A primary immune response can become weakened or attenuated over time and can even disappear or at least become so attenuated that it cannot be detected. Accordingly, the present invention also relates to a "secondary" immune response, which is also described here as a "memory immune response." The term secondary immune response refers to an immune response elicited in an individual after a primary immune response has already been produced. Thus, a secondary or immune response can be elicited, e.g., to enhance an existing immune response that has become weakened or attenuated, or to recreate a previous immune response that has either disappeared or can no longer be detected. An agent that can be administrated to elicit a secondary immune response is after referred to as a "booster" since the agent can be said to "boost" the primary immune response.

As an example, and not by way of limitation, a secondary immune response can be elicited by re-introducing to the individual an antigen that elicited the primary immune response (for example, by re-administrating a vaccine). However, a secondary immune response to an antigen can also be elicited by administrating other agents that can not contain the actual antigen. For example, the present invention provides methods for potentiating a secondary immune response by administrating an antibody to IGF-I or IGF-II to an individual. In such methods the actual antigen need not necessarily be administered with the antibody to IGF-I or IGF-II and the composition containing the antibody need not necessarily contain the antigen. The secondary or memory immune response can be either a humoral (antibody) response or a cellular response. A secondary or memory humoral response occurs upon stimulation of memory B cells that were generated at the first presentation of the antigen. Delayed type hypersensitivity (DTH) reactions are a type of cellular secondary or memory immune response that are mediated by CD4$^+$ cells. A first exposure to an antigen primes the immune system and additional exposure(s) results in a DTH.

"Immunologically cross-reactive" or "immunologically reactive" refers to an antigen which is specifically reactive with an antibody which was generated using the same ("immunologically reactive") or different ("immunologically cross-reactive") antigen. Generally, the antigen is IGF-I, IGF-II, or IGF-1 receptor, or subsequence thereof.

"Immunologically reactive conditions" refers to conditions which allow an antibody, generated to a particular epitope of an antigen, to bind to that epitope to a detectably greater degree than the antibody binds to substantially all other epitopes, generally at least two times above background binding, preferably at least five times above background. Immunologically reactive conditions are dependent upon the format of the antibody binding reaction and typically are those utilized in immunoassay protocols. See, Harlow and Lane, *Antibodies, A Laboratory Manual*, Cold Spring Harbor Publications, New York, 1988 for a description of immunoassay formats and conditions.

"Cell surface receptor" refers to molecules and complexes of molecules capable of receiving a signal and the transmission of such a signal across the plasma membrane of a cell. An example of a "cell surface receptor" of the present invention is an IGF-1 receptor on a metastatic cell.

"Nonspecific T cell activation" refers to the stimulation of T cells independent of their antigenic specificity.

"Effector cell" refers to an immune cell which is involved in the effector phase of an immune response, as opposed to the cognitive and activation phases of an immune response. Exemplary immune cells include a cell of a myeloid or lymphoid origin, e.g., lymphocytes (e.g., B cells and T cells including cytolytic T cells (CTLs)), killer cells, natural killer cells, macrophages, monocytes, eosinophils, neutrophils, polymorphonuclear cells, granulocytes, mast cells, and basophils. Effector cells express specific Fc receptors and carry out specific immune functions. An effector cell can induce antibody-dependent cell-mediated cytotoxicity (ADCC), e.g., a neutrophil capable of inducing ADCC. For example, monocytes, macrophages, neutrophils, eosinophils, and lymphocytes which express FcαR are involved in specific killing of target cells and presenting antigens to other components of the immune system, or binding to cells that present antigens. An effector cell can also phagocytose a target antigen, target cell, metastatic cancer cell, or microorganism.

"Target cell" refers to any undesirable cell in a subject (e.g., a human or animal) that can be targeted by the Ab or Ab composition of the invention. The target cell can be a cell expressing or overexpressing human IGF-1 receptor. Cells expressing human IGF-1 receptor can include tumor cells, e.g. breast cancer cells or metastatic breast cancer cells.

Targets of interest for antibody compositions metastatic cancer cells, e.g., metastatic breast cancer cells, include, but are not limited to, cell surface receptors, growth factor receptors, IGF-1, IGF-II, IGF-1 receptor, (See, for example, Burtrum D., et al, *Cancer Res.*, 63: 8912-8921, 2003; Lu et al., *J. Biol. Chem.* 279: 2856-2865, 2004; Miyamoto et al., *Clin. Cancer Res.* 11: 3494-3502, 2005; Goya et al., *Cancer Research* 64: 6252-6258, 2004.) antibodies, including anti-idiotypic antibodies and autoantibodies present in cancer, such as metastatic cancer and metastatic breast cancer. Other targets are adhesion proteins such as integrins, selectins, and immunoglobulin superfamily members. Springer, *Nature*, 346: 425-433, 1990; Osborn, *Cell*, 62: 3, 1990; Hynes, *Cell*, 69: 11, 1992. Other targets of interest are growth factor receptors (e.g., FGFR, PDGFR, EGF, her/neu, NGFR, and VEGF) and their ligands. Other targets are G-protein receptors and include substance K receptor, the angiotensin receptor, the α- and β-adrenergic receptors, the serotonin receptors, and PAF receptor. See, e.g., Gilman, *Ann. Rev. Biochem.* 56: 625-649, 1987. Other targets include ion channels (e.g., calcium, sodium, potassium channels, channel proteins that mediate multidrug resistance), muscarinic receptors, acetylcholine receptors, GABA receptors, glutamate receptors, and dopamine receptors (see Harpold, U.S. Pat. No. 5,401,629 and U.S. Pat. No. 5,436,128). Other targets are cytokines, such as interleukins IL-1 through IL-13, tumor necrosis factors α- and β, interferons α-, β- and γ, tumor growth factor Beta (TGF-β), colony stimulating factor (CSF) and granulocyte monocyte colony stimulating factor (GM-CSF). See Aggrawal et al., eds., *Human Cytokines: Handbook for Basic & Clinical Research*, Blackwell Scientific, Boston, Mass., 1991. Other targets are hormones, enzymes, and intracellular and intercellular messengers, such as adenyl cyclase, guanyl cyclase, and phospholipase C. Drugs are also targets of interest. Target molecules can be human, mammalian or bacterial. Other targets are antigens, such as proteins, glycoproteins and carbohydrates from microbial pathogens, both viral and bacterial, and tumors. Still other targets are described in U.S. Pat. No. 4,366,241, incorporated herein by reference in its entirety and for all purposes. Some agents screened by the target merely bind to a target. Other agents agonize or antagonize the target.

Recombinant Expression of Anti-IGF-I or Anti-IGF-II Antibodies

Recombinant human antibodies that inhibit IGF-I or IGF-II binding to IGF-1R, are provided according to the present invention using known techniques based on the teaching provided herein. See, e.g., Ausubel et al., eds. *Current Protocols in Molecular Biology*, Wiley Interscience, N.Y. (1987, 1992, 1993); and Sambrook et al. *Molecular Cloning: A Laboratory Manual*, Cold Spring Harbor Laboratory Press (1989), the entire contents of which are incorporated herein by reference.

The DNA encoding an anti-IGF-I or anti-IGF-II antibody of the present invention can be genomic DNA or cDNA which encodes at least one of the heavy chain constant region (CH), the heavy chain variable region ($V_H$), the light chain variable region ($V_L$) and the light chain constant regions ($C_L$). A convenient alternative to the use of chromosomal gene fragments as the source of DNA encoding the murine V region antigen-binding segment is the use of cDNA for the construction of chimeric immunoglobulin genes, e.g., as reported by Liu et al., *Proc. Natl. Acad. Sci., USA* 84:3439 (1987) and *J. Immunology* 139: 3521 (1987), which references are hereby entirely incorporated herein by reference. The use of cDNA requires that gene expression elements appropriate for the host cell be combined with the gene in order to achieve synthesis of the desired protein. The use of cDNA sequences is advantageous over genomic sequences (which contain introns), in that cDNA sequences can be expressed in bacteria or other hosts which lack appropriate RNA splicing systems.

Such techniques for synthesizing such oligonucleotides are well known and disclosed by, for example, Wu, et al., *Prog. Nucl. Acid. Res. Molec. Biol* 21:101-141 (1978)), and Ausubel et al., eds. *Current Protocols in Molecular Biology*, Wiley Interscience (1987, 1993), the entire contents of which are herein incorporated by reference.

Because the genetic code is degenerate, more than one codon can be used to encode a particular amino acid (Watson, et al., infra). Using the genetic code, one or more different oligonucleotides can be identified, each of which would be capable of encoding the amino acid. The probability that a particular oligonucleotide will, in fact, constitute the actual anti-IGF-I or anti-IGF-II antibody encoding sequence can be estimated by considering abnormal base pairing relationships and the frequency with which a particular codon is actually used (to encode a particular amino acid) in eukaryotic or prokaryotic cells expressing an anti-IGF-I or IGF-II antibody or fragment. Such "codon usage rules" are disclosed by Lathe, et al., *J. Molec. Biol.* 183:1-12 (1985). Using the "codon usage rules" of Lathe, a single oligonucleotide, or a set of oligonucleotides, that contains a theoretical "most probable" nucleotide sequence capable of encoding anti-IGF-I or IGF-II variable or constant region sequences is identified.

Although occasionally an amino acid sequence can be encoded by only a single oligonucleotide, frequently the amino acid sequence can be encoded by any of a set of similar oligonucleotides. Importantly, whereas all of the members of this set contain oligonucleotides which are capable of encoding the peptide fragment and, thus, potentially contain the same oligonucleotide sequence as the gene which encodes the peptide fragment, only one member of the set contains the nucleotide sequence that is identical to the nucleotide sequence of the gene. Because this member is present within the set, and is capable of hybridizing to DNA even in the presence of the other members of the set, it is possible to employ the unfractionated set of oligonucleotides in the same manner in which one would employ a single oligonucleotide to clone the gene that encodes the protein.

The oligonucleotide, or set of oligonucleotides, containing the theoretical "most probable" sequence capable of encoding an anti-IGF-I or anti-IGF-II antibody or fragment including a variable or constant region is used to identify the sequence of a complementary oligonucleotide or set of oligonucleotides which is capable of hybridizing to the "most probable" sequence, or set of sequences. An oligonucleotide containing such a complementary sequence can be employed as a probe to identify and isolate the variable or constant region anti-IGF-I or anti-IGF-II gene (Sambrook et al., infra).

A suitable oligonucleotide, or set of oligonucleotides, which is capable of encoding a fragment of the variable or constant anti-IGF-I or anti-IGF-II region (or which is complementary to such an oligonucleotide, or set of oligonucleotides) is identified (using the above-described procedure), synthesized, and hybridized by means well known in the art, against a DNA or, more preferably, a cDNA preparation derived from cells which are capable of expressing anti-IGF-I or anti-IGF-II antibodies or variable or constant regions thereof. Single stranded oligonucleotide molecules complementary to the "most probable" variable or constant anti-IGF-I or anti-IGF-II region peptide coding sequences can be synthesized using procedures which are well known to those of ordinary skill in the art (Belagaje, et al., *J. Biol. Chem.* 254: 5765-5780 (1979); Maniatis, et al., In: Molecular Mechanisms in the Control of Gene Expression, Nierlich, et al., Eds., Acad. Press, NY (1976); Wu, et al., *Prog. Nucl. Acid Res. Molec. Biol.* 21: 101-141 (1978); Khorana, *Science* 203: 614-625 (1979)). Additionally, DNA synthesis can be achieved through the use of automated synthesizers. Techniques of nucleic acid hybridization are disclosed by Sambrook et al. (infra), and by Haymes, et al. (In: Nucleic Acid Hybridization, A Practical Approach, IRL Press, Washington, D.C. (1985)), which references are herein incorporated by reference. Techniques such as, or similar to, those described above have successfully enabled the cloning of genes for human aldehyde dehydrogenases (Hsu, et al., *Proc. Natl. Acad. Sci. USA* 82: 3771-3775 (1985)), fibronectin (Suzuki, et al., *Bur. Mol. Biol. Organ. J.* 4: 2519-2524 (1985)), the human estrogen receptor gene (Walter, et al., *Proc. Natl. Acad. Sci. USA* 82: 7889-7893 (1985)), tissue-type plasminogen activator (Pennica, et al., *Nature* 301: 214-221 (1983)) and human term placental alkaline phosphatase complementary DNA (Keun, et al., *Proc. Natl. Acad. Sci. USA* 82: 8715-8719 (1985)).

In an alternative way of cloning a polynucleotide encoding an anti-IGF-I or anti-IGF-II variable or constant region, a library of expression vectors is prepared by cloning DNA or, more preferably, cDNA (from a cell capable of expressing an anti-IGF-I or anti-IGF-II antibody or variable or constant region) into an expression vector. The library is then screened for members capable of expressing a protein which competitively inhibits the binding of an anti-IGF-I or anti-IGF-II antibody, such as m705, m706, m708, or m708.2, to IGF-1R and which has a nucleotide sequence that is capable of encoding polypeptides that have the same amino acid sequence as anti-IGF-I or anti-IGF-II antibodies or fragments thereof. In this embodiment, DNA, or more preferably cDNA, is extracted and purified from a cell which is capable of expressing an anti-IGF-I or anti-IGF-II antibody or fragment. The purified cDNA is fragmentized (by shearing, endonuclease digestion, etc.) to produce a pool of DNA or cDNA fragments. DNA or cDNA fragments from this pool are then cloned into an expression vector in order to produce a genomic library of expression vectors whose members each contain a unique cloned DNA or cDNA fragment such as in a lambda phage library, expression in prokaryotic cell (e.g., bacteria) or eukaryotic cells, (e.g., mammalian, yeast, insect or, fungus). See, e.g., Ausubel, infra, Harlow, infra, Colligan, infra; Nyyssonen et al. *Bio/Technology* 11: 591-595 (Can 1993); Marks et al., *Bio/Technology* 11: 1145-1149, 1993. Once nucleic acid encoding such variable or constant anti-IGF-I or anti-IGF-II regions is isolated, the nucleic acid can be appropriately expressed in a host cell, along with other constant or variable heavy or light chain encoding nucleic acid, in order to provide recombinant MAbs that bind IGF-I or IGF-II with inhibitory activity. Such antibodies preferably include a murine or human anti-IGF-I or anti-IGF-II variable region which contains a framework residue having complimentarily determining residues which are responsible for antigen binding. In a preferred embodiment, an anti-IGF-I or anti-IGF-II variable light or heavy chain encoded by a nucleic acid as described above binds an epitope of at least 5 amino acids of SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8.

Human genes which encode the constant (C) regions of the murine and chimeric antibodies, fragments and regions of the present invention can be derived from a human fetal liver library, by known methods. Human C regions genes can be derived from any human cell including those which express and produce human immunoglobulins. The human $C_H$ region can be derived from any of the known classes or isotypes of human H chains, including $\gamma$, $\mu$, $\alpha$, $\delta$, or $\epsilon$, and subtypes thereof, such as G1, G2, G3 and G4. Since the H chain isotype is responsible for the various effector functions of an antibody, the choice of $C_H$ region will be guided by the desired effector functions, such as complement fixation, or activity in antibody-dependent cellular cytotoxicity (ADCC). Preferably, the $C_H$ region is derived from gamma 1 (IgG1), gamma 3 (IgG3), gamma 4 (IgG4), or mu (IgM).

Human Antibodies and Humanization of Antibodies

Human antibodies avoid certain of the problems associated with antibodies that possess murine or rat variable and/or constant regions. The presence of such murine or rat derived proteins can lead to the rapid clearance of the antibodies or can lead to the generation of an immune response against the antibody by a patient. In order to avoid the utilization of murine or rat derived antibodies, it has been postulated that one can develop humanized antibodies or generate fully human antibodies through the introduction of human antibody function into a rodent so that the rodent would produce antibodies having fully human sequences.

The ability to clone and reconstruct megabase-sized human loci in YACs and to introduce them into the mouse germline provides a powerful approach to elucidating the functional components of very large or crudely mapped loci as well as generating useful models of human disease. Furthermore, the utilization of such technology for substitution of mouse loci with their human equivalents could provide unique insights into the expression and regulation of human gene products during development, their communication with other systems, and their involvement in disease induction and progression.

An important practical application of such a strategy is the "humanization" of the mouse humoral immune system. Introduction of human immunoglobulin (Ig) loci into mice in which the endogenous Ig genes have been inactivated offers the opportunity to study the mechanisms underlying programmed expression and assembly of antibodies as well as their role in B-cell development. Furthermore, such a strategy could provide an ideal source for production of fully human monoclonal antibodies (Mabs) an important milestone towards fulfilling the promise of antibody therapy in human disease. Fully human antibodies are expected to minimize the immunogenic and allergic responses intrinsic to mouse or mouse-derivatized Mabs and thus to increase the efficacy and safety of the administered antibodies. The use of fully human antibodies can be expected to provide a substantial advantage in the treatment of chronic and recurring human diseases, such as inflammation, autoimmunity, and cancer, which require repeated antibody administrations.

One approach towards this goal was to engineer mouse strains deficient in mouse antibody production with large fragments of the human Ig loci in anticipation that such mice would produce a large repertoire of human antibodies in the absence of mouse antibodies. Large human Ig fragments would preserve the large variable gene diversity as well as the proper regulation of antibody production and expression. By exploiting the mouse machinery for antibody diversification and selection and the lack of immunological tolerance to human proteins, the reproduced human antibody repertoire in these mouse strains should yield high affinity antibodies against any antigen of interest, including human antigens. Using the hybridoma technology, antigen-specific human Mabs with the desired specificity could be readily produced and selected.

This general strategy was demonstrated in connection with our generation of the first XenoMouse™ strains as published in 1994. See Green et al., *Nature Genetics* 7: 13-21, 1994. The XenoMouse™ strains were engineered with yeast artificial chromosomes (YACs) containing 245 kb and 190 kb-sized germline configuration fragments of the human heavy chain locus and kappa light chain locus, respectively, which contained core variable and constant region sequences. Id. The human Ig containing YACs proved to be compatible with the mouse system for both rearrangement and expression of antibodies and were capable of substituting for the inactivated mouse Ig genes. This was demonstrated by their ability to induce B-cell development, to produce an adult-like human repertoire of fully human antibodies, and to generate antigen-specific human Mabs. These results also suggested that introduction of larger portions of the human Ig loci containing greater numbers of V genes, additional regulatory elements, and human Ig constant regions might recapitulate substantially the full repertoire that is characteristic of the human humoral response to infection and immunization. The work of Green et al. was recently extended to the introduction of greater than approximately 80% of the human antibody repertoire through introduction of megabase sized, germline configuration YAC fragments of the human heavy chain loci and kappa light chain loci, respectively, to produce XenoMouse™ mice. See Mendez et al., *Nature Genetics* 15: 146-156, 1997, Green and Jakobovits, *J. Exp. Med.* 188: 483-495, 1998, and U.S. patent application Ser. No. 08/759,620, filed Dec. 3, 1996, the disclosures of which are hereby incorporated by reference.

Such approach is further discussed and delineated in U.S. patent application Ser. No. 07/466,008, filed Jan. 12, 1990, Ser. No. 07/610,515, filed Nov. 8, 1990, Ser. No. 07/919,297, filed Jul. 24, 1992, Ser. No. 07/922,649, filed Jul. 30, 1992, filed Ser. No. 08/031,801, filed Mar. 15, 1993, Ser. No. 08/112,848, filed Aug. 27, 1993, Ser. No. 08/234,145, filed Apr. 28, 1994, Ser. No. 08/376,279, filed Jan. 20, 1995, Ser. No. 08/430,938, Apr. 27, 1995, Ser. No. 08/464,584, filed Jun. 5, 1995, Ser. No. 08/464,582, filed Jun. 5, 1995, Ser. No. 08/463,191, filed Jun. 5, 1995, Ser. No. 08/462,837, filed Jun. 5, 1995, Ser. No. 08/486,853, filed Jun. 5, 1995, Ser. No. 08/486,857, filed Jun. 5, 1995, Ser. No. 08/486,859, filed Jun. 5, 1995, Ser. No. 08/462,513, filed Jun. 5, 1995, Ser. No. 08/724,752, filed Oct. 2, 1996, and Ser. No. 08/759,620, filed Dec. 3, 1996. See also Mendez et al., *Nature Genetics* 15: 146-156, 1997 and Green and Jakobovits, *J. Exp. Med.* 188: 483-495, 1998. See also European Patent No., EP 0 463 151 B1, grant published Jun. 12, 1996, International Patent Application No., WO 94/02602, published Feb. 3, 1994, International Patent Application No., WO 96/34096, published Oct. 31, 1996, and WO 98/24893, published Jun. 11, 1998. The disclosures of each of the above-cited patents, applications, and references are hereby incorporated by reference in their entirety.

In an alternative approach, others, including GenPharm International, Inc., have utilized a "minilocus" approach. In the minilocus approach, an exogenous Ig locus is mimicked through the inclusion of pieces (individual genes) from the Ig locus. Thus, one or more $V_H$ genes, one or more $D_H$ genes, one or more $J_H$ genes, a mu constant region, and a second constant region (preferably a gamma constant region) are formed into a construct for insertion into an animal. This approach is described in U.S. Pat. No. 5,545,807 to Surani et al. and U.S. Pat. Nos. 5,545,806, 5,625,825, 5,625,126, 5,633,425, 5,661,016, 5,770,429, 5,789,650, and 5,814,318 each to Lonberg and Kay, U.S. Pat. No. 5,591,669 to Krimpenfort and Berns, U.S. Pat. Nos. 5,612,205, 5,721,367, 5,789,215 to Berns et al., and U.S. Pat. No. 5,643,763 to Choi and Dunn, and GenPharm International U.S. patent application Ser. No. 07/574,748, filed Aug. 29, 1990, now abandoned, Ser. No. 07/575,962, filed Aug. 31, 1990, now abandoned, Ser. No. 07/810,279, filed Dec. 17, 1991, issued as U.S. Pat. No. 5,569,825, Ser. No. 07/853,408, filed Mar. 18, 1992, issued as U.S. Pat. No. 5,789,650, Ser. No. 07/904,068, filed Jun. 23, 1992, now abandoned, Ser. No. 07/990,860, filed Dec. 16, 1992, issued as U.S. Pat. No. 5,545,806, Ser. No. 08/053,131, filed Apr. 26, 1993, issued as U.S. Pat. No. 5,661,016, Ser. No. 08/096,762, filed Jul. 22, 1993, isssued as U.S. Pat. No. 5,814,318, Ser. No. 08/155,301, filed Nov. 18, 1993, Ser. No. 08/161,739, filed Dec. 3, 1993, Ser. No. 08/165,699, filed Dec. 10, 1993, Ser. No. 08/209,741, filed Mar. 9, 1994, now abandoned the disclosures of which are hereby incorporated by reference. See also European Patent No. 0 546 073 B1, International Patent Application Nos. WO 92/03918, WO 92/22645, WO 92/22647, WO92/22670, WO 93/12227, WO 94/00569, WO 94/25585, WO 96/14436, WO 97/13852, and WO 98/24884, the disclosures of which are hereby incorporated by reference in their entirety. See further Taylor et al., 1992, Chen et al., 1993, Tuaillon et al., 1993, Choi et al., 1993, Lonberg et al., 1994, Taylor et al., 1994, and Tuaillon et al., 1995, Fishwild et al., 1996, the disclosures of which are hereby incorporated by reference in their entirety.

A transgenic mouse possessing an Ig locus has been produced through use of the minilocus approach. An advantage of the minilocus approach is the rapidity with which constructs including portions of the Ig locus can be generated and introduced into animals. Commensurately, however, a significant disadvantage of the minilocus approach is that, in theory, insufficient diversity is introduced through the inclusion of small numbers of V, D, and J genes. Indeed, the published work appears to support this concern. B-cell development and antibody production of animals produced through use of the minilocus approach appear stunted. Therefore, research surrounding the present invention has consistently been directed towards the introduction of large portions of the Ig locus in order to achieve greater diversity and in an effort to reconstitute the immune repertoire of the animals.

Human anti-mouse antibody (HAMA) responses have led the industry to prepare chimeric or otherwise humanized antibodies. While chimeric antibodies have a human constant region and a murine variable region, it is expected that certain human anti-chimeric antibody (HACA) responses will be observed, particularly in chronic or multi-dose utilizations of the antibody. Thus, it would be desirable to provide fully human antibodies against IGF-I or IGF-II in order to vitiate concerns and/or effects of HAMA or HACA response.

Humanization and Display Technologies

As was discussed above in connection with human antibody generation, there are advantages to producing antibodies with reduced immunogenicity. To a degree, this can be accomplished in connection with techniques of humanization and display techniques using appropriate libraries. It will be appreciated that murine antibodies or antibodies from other species can be humanized or primatized using techniques well known in the art. See e.g., Winter and Harris, *Immunol Today* 14: 43-46, 1993 and Wright et al., *Crit. Reviews in Immunol.* 12:125-168, 1992. The antibody of interest may be engineered by recombinant DNA techniques to substitute the $C_H1$, $C_H2$, $C_H3$, hinge domains, and/or the framework domain with the corresponding human sequence (see WO 92/02190 and U.S. Pat. Nos. 5,530,101, 5,585,089, 5,693,761, 5,693,792, 5,714,350, and 5,777,085). Also, the use of Ig cDNA for construction of chimeric immunoglobulin genes is known in the art (Liu et al., *PNAS USA* 84: 3439, 1987 and J. Immunol. 139: 3521, 1987). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) Sequences of Proteins of Immunological Interest, NIH publication no. 91-3242. Human C region genes are readily available from known clones. The choice of isotype will be guided by the desired effector functions, such as complement fixation, or activity in antibody-dependent cellular cytotoxicity. Preferred isotypes are IgG1, IgG2, IgG3 and IgG4. Particularly preferred isotypes for antibodies of the invention are IgG2 and IgG4. Either of the human light chain constant regions, kappa or lambda, may be used. The chimeric, humanized antibody is then expressed by conventional methods.

Antibody fragments, such as Fv, F(ab')$_2$ and Fab may be prepared by cleavage of the intact protein, e.g. by protease or chemical cleavage. Alternatively, a truncated gene is designed. For example, a chimeric gene encoding a portion of the F(ab')$_2$ fragment would include DNA sequences encoding the CH1 domain and hinge region of the H chain, followed by a translational stop codon to yield the truncated molecule.

In one approach, consensus sequences encoding the heavy and light chain J regions may be used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, cosmids, YACs, EBV derived episomes, and the like. A convenient vector is one that encodes a functionally complete human $C_H$ or $C_L$ immunoglobulin sequence, with appropriate restriction sites engineered so that any $V_H$ or $V_L$ sequence can be easily inserted and expressed. In such vectors, splicing usually occurs between the splice donor site in the inserted J region and the splice acceptor site preceding the human C region, and also at the splice regions that occur within the human $C_H$ exons. Polyadenylation and transcription termination occur at native chromosomal sites downstream of the coding regions. The resulting chimeric antibody may be joined to any strong promoter, including retroviral LTRs, e.g. SV-40 early promoter, (Okayama et al., *Mol. Cell. Bio.* 3: 280, 1983), Rous sarcoma virus LTR (Gorman et al., *P.N.A.S.* 79: 6777, 1982), and moloney murine leukemia virus LTR (Grosschedl et al., *Cell* 41: 885, 1985); native 1 g promoters, etc.

Further, human antibodies or antibodies from other species can be generated through display-type technologies, including, without limitation, phage display, retroviral display, ribosomal display, and other techniques, using techniques well known in the art and the resulting molecules can be subjected to additional maturation, such as affinity maturation, as such techniques are well known in the art. Wright and Harris, supra., Hanes and Plucthau, *PNAS USA* 94: 4937-4942, 1997 (ribosomal display), Parmley and Smith, *Gene* 73: 305-318, 1988 (phage display), Scott, *TIBS* 17: 241-245, 1992, Cwirla et al., *PNAS USA* 87: 6378-6382, 1990, Russel et al., *Nucl. Acids Research* 21: 1081-1085, 1993, Hoganboom et al., *Immunol. Reviews* 130: 43-68, 1992, Chiswell and McCafferty, *TIBTECH* 10: 80-84, 1992, and U.S. Pat. No. 5,733, 743. If display technologies are utilized to produce antibodies that are not human, such antibodies can be humanized as described above.

Using these techniques, antibodies can be generated to IGF-I expressing or IGF-II expressing cells, IGF-I or IGF-II or forms of IGF-I or IGF-II, epitopes or peptides thereof, and expression libraries thereto (see e.g. U.S. Pat. No. 5,703,057) which can thereafter be screened as described above for the activities described above.

Design and Generation of Other Therapeutics

In accordance with the present invention and based on the activity of the antibodies that are produced and characterized herein with respect to IGF-I or IGF-II, the design of other therapeutic modalities including other antibodies, other antagonists, or chemical moieties other than antibodies is facilitated. Such modalities include, without limitation, antibodies having similar binding activity or functionality, advanced antibody therapeutics, such as bispecific antibodies, immunotoxins, and radiolabeled therapeutics, generation of peptide therapeutics, gene therapies, particularly intrabodies, antisense therapeutics, and small molecules. Furthermore, as discussed above, the effector function of the antibodies of the invention may be changed by isotype switching to an IgG1, IgG2, IgG3, IgG4, IgD, IgA, IgE, or IgM for various therapeutic uses.

In connection with the generation of advanced antibody therapeutics, where complement fixation is a desirable attribute, it may be possible to sidestep the dependence on complement for cell killing through the use of bispecifics, immunotoxins, or radiolabels, for example.

In connection with bispecific antibodies, bispecific antibodies can be generated that comprise (i) two antibodies one with a specificity to IGF-I or IGF-II and another to a second molecule that are conjugated together, (ii) a single antibody that has one chain specific to IGF-I or IGF-II and a second chain specific to a second molecule, or (iii) a single chain antibody that has specificity to IGF-I or IGF-II and the other molecule. Such bispecific antibodies can be generated using techniques that are well known for example, in connection with (i) and (ii) see e.g., Fanger et al., *Immunol Methods* 4: 72-81, 1994 and Wright and Harris, supra. and in connection with (iii) see e.g., Traunecker et al., *Int. J. Cancer* 7: 51-52, 1992.

In addition, "Kappabodies" (Ill et al., *Protein Eng* 10: 949-57, 1997), "Minibodies" (Martin et al., *EMBO J.* 13: 5303-9, 1994), "Diabodies" (Holliger et al., *PNAS USA* 90: 6444-6448, 1993), or "Janusins" (Traunecker et al., *EMBO J.* 10: 3655-3659, 1991) and Traunecker et al., *Int J Cancer* 7:51-52, 1992) may also be prepared.

In connection with immunotoxins, antibodies can be modified to act as immunotoxins utilizing techniques that are well known in the art. See e.g., Vitetta, *Immunol Today* 14: 252, 1993. See also U.S. Pat. No. 5,194,594. In connection with the preparation of radiolabeled antibodies, such modified antibodies can also be readily prepared utilizing techniques that are well known in the art. See e.g., Junghans et al., Cancer Chemotherapy and Biotherapy 655-686 (2d edition, Chafier and Longo, eds., Lippincott Raven, 1996). See also U.S. Pat. Nos. 4,681,581, 4,735,210, 5,101,827, 5,102,990 (RE 35,500), 5,648,471, and 5,697,902. Each of immunotoxins and radiolabeled molecules would be likely to kill cells expressing IGF-I or IGF-II, and particularly those cells in which the antibodies of the invention are effective.

In connection with the generation of therapeutic peptides, through the utilization of structural information related to IGF-I or IGF-II and antibodies thereto, such as the antibodies of the invention (as discussed below in connection with small molecules) or screening of peptide libraries, therapeutic peptides can be generated that are directed against IGF-I or IGF-II. Design and screening of peptide therapeutics is discussed in connection with Houghten et al., *Biotechniques* 13: 412-421, 1992, Houghten *PNAS USA* 82: 5131-5135, 1985, Pinalla et al., *Biotechniques* 13: 901-905, 1992, Blake and Litzi-Davis, *BioConjugate Chem.* 3: 510-513, 1992. Immunotoxins and radiolabeled molecules can also be prepared, and in a similar manner, in connection with peptidic moieties as discussed above in connection with antibodies.

Important information related to the binding of an antibody to an antigen can be gleaned through phage display experimentation. Such experiments are generally accomplished through panning a phage library expressing random peptides for binding with the antibodies of the invention to determine if peptides can be isolated that bind. If successful, certain epitope information can be gleaned from the peptides that bind.

In general, phage libraries expressing random peptides can be purchased from New England Biolabs (7-mer and 12-mer libraries, Ph.D.-7 Peptide 7-mer Library Kit and Ph.D.-12 Peptide 12-mer Library Kit, respectively) based on a bacteriophage M13 system. The 7-mer library represents a diversity of approximately $2.0 \times 10^9$ independent clones, which represents most, if not all, of the $20^7 = 1.28 \times 10^9$ possible 7-mer sequences. The 12-mer library contains approximately $1.9 \times 10^9$ independent clones and represents only a very small sampling of the potential sequence space of $20^{12} = 4 \times 10^{15}$ 12-mer sequences. Each of 7-mer and 12-mer libraries are panned or screened in accordance with the manufacturer's recommendations in which plates were coated with an antibody to capture the appropriate antibody (a goat anti-human IgG Fc for an IgG antibody for example) followed by washing. Bound phage are eluted with 0.2 M glycine-HCl, pH 2.2. After 3 rounds of selection/amplification at constant stringency (0.5% Tween), through use of DNA sequencing, one can characterize clones from the libraries that are reactive with one or more of the antibodies. Reactivity of the peptides can be determined by ELISA. For an additional discussion of epitope analysis of peptides see also Scott and Smith, *Science* 249: 386-390, 1990; Cwirla et al., *PNAS USA* 87: 6378-6382, 1990; Felici et al., *J. Mol. Biol.* 222: 301-310, 1991, and Kuwabara et al., *Nature Biotechnology* 15: 74-78, 1997.

The design of gene and/or antisense therapeutics through conventional techniques is also facilitated through the present invention. Such modalities can be utilized for modulating the function of IGF-I or IGF-II. In connection therewith the antibodies of the present invention facilitate design and use of functional assays related thereto. A design and strategy for antisense therapeutics is discussed in detail in International Patent Application No. WO 94/29444. Design and strategies for gene therapy are well known. However, in particular, the use of gene therapeutic techniques involving intrabodies could prove to be particularly advantageous. See e.g., Chen et al., *Human Gene Therapy* 5: 595-601, 1994 and Marasco, *Gene Therapy* 4: 11-15, 1997. General design of and considerations related to gene therapeutics is also discussed in International Patent Application No. WO 97/38137. Genetic materials encoding an antibody of the invention (such as mAb m705, m706, m708 and m708.2, or others) may be included in a suitable expression system (whether viral, attenuated viral, non-viral, naked, or otherwise) and administered to a host for in vivo generation of the antibody in the host.

Small molecule therapeutics can also be envisioned in accordance with the present invention. Drugs can be designed to modulate the activity of IGF-I or IGF-II based upon the present invention. Knowledge gleaned from the structure of the IGF-I or IGF-II molecule and its interactions with other molecules in accordance with the present invention, such as the antibodies of the invention, IGF-1R, and others can be utilized to rationally design additional therapeutic modalities. In this regard, rational drug design techniques such as X-ray crystallography, computer-aided (or assisted) molecular modeling (CAMM), quantitative or qualitative structure-activity relationship (QSAR), and similar technologies can be utilized to focus drug discovery efforts. Rational design allows prediction of protein or synthetic structures which can interact with the molecule or specific forms thereof which can be used to modify or modulate the activity of IGF-I or IGF-II. Such structures can be synthesized chemically or expressed in biological systems. This approach has been reviewed in Capsey et al., Genetically Engineered Human Therapeutic Drugs (Stockton Press, NY, 1988). Indeed, the rational design of molecules (either peptides, peptidomimetics, small molecules, or the like) based upon known, or delineated, structure-activity relationships with other molecules (such as antibodies in accordance with the invention) has become generally routine. See, e.g., Fry et al., *Proc Natl Acad Sci USA* 95: 12022-7, 1998; Hoffman et al., *J Mol Biol* 282: 195-208, 1998; Ginalski et al., *Acta Biochim Pol* 44: 557-64, 1997; Jouko et al., *Biochem J* 322: 927-35, 1997; Singh et al., *J Med*

Chem 40: 1130-5, 1997; Mandel et al., *Nat Biotechnol* 14: 323-8, 1996; Monfardini et al., *Proc Assoc Am Physicians* 108: 420-31, 1996; Furet et al., *J Comput Aided Mol Des* 9: 465-72, 1995.

Further, combinatorial libraries can be designed and synthesized and used in screening programs, such as high throughput screening efforts.

Preparation of Antibodies in Transgenic Mice

Antibodies in accordance with the invention are preferably prepared through the utilization of a transgenic mouse that has a substantial portion of the human antibody producing genome inserted but that is rendered deficient in the production of endogenous, murine, antibodies. Such mice, then, are capable of producing human immunoglobulin molecules and antibodies and are deficient in the production of murine immunoglobulin molecules and antibodies. In particular, however, a preferred embodiment of transgenic production of mice and antibodies therefrom is disclosed in U.S. patent application Ser. No. 08/759,620, filed Dec. 3, 1996, the disclosure of which is hereby incorporated by reference. See also Mendez et al., *Nature Genetics* 15: 146-156, 1997, the disclosure of which is hereby incorporated by reference.

Through use of such technology, we have produced fully human monoclonal antibodies to a variety of antigens. Essentially, we immunize XenoMouse™ lines of mice with an antigen of interest, recover lymphatic cells (such as B-cells) from the mice that express antibodies, fuse such recovered cells with a myeloid-type cell line to prepare immortal hybridoma cell lines, and such hybridoma cell lines are screened and selected to identify hybridoma cell lines that produce antibodies specific to the antigen of interest. We utilized these techniques in accordance with the present invention for the preparation of antibodies specific to IGF-I or IGF-II. Herein, we describe the production of multiple hybridoma cell lines that produce antibodies specific to IGF-I or IGF-II. Further, we provide a characterization of the antibodies produced by such cell lines, including nucleotide and amino acid sequence analyses of the heavy and light chains of such antibodies.

The antibodies derived from 293 free style cell lines for mAb m705, m706, m708 and m708.2 were expressed as discussed herein. Each of the antibodies produced by the aforementioned cell lines are either fully human IgG1 heavy chains and human IgG1 light chains. In general, antibodies in accordance with the invention possess very high affinities, typically possessing $K_d$'s of from about $10^{-9}$ through about $10^{-11}$ M, when measured by either solid phase or solution phase.

As will be appreciated, antibodies in accordance with the present invention can be expressed in cell lines other than hybridoma cell lines. Sequences encoding the cDNAs or genomic clones for the particular antibodies can be used for transformation of a suitable mammalian or nonmammalian host cells. Transformation can be by any known method for introducing polynucleotides into a host cell, including, for example packaging the polynucleotide in a virus (or into a viral vector) and transducing a host cell with the virus (or vector) or by transfection procedures known in the art, as exemplified by U.S. Pat. Nos. 4,399,216, 4,912,040, 4,740, 461, and 4,959,455 (which patents are hereby incorporated herein by reference). The transformation procedure used depends upon the host to be transformed. Methods for introduction of heterologous polynucleotides into mammalian cells are well known in the art and include, but are not limited to, dextran-mediated transfection, calcium phosphate precipitation, polybrene mediated transfection, protoplast fusion, electroporation, particle bombardment, encapsulation of the polynucleotide(s) in liposomes, peptide conjugates, dendrimers, and direct microinjection of the DNA into nuclei.

Mammalian cell lines available as hosts for expression are well known in the art and include many immortalized cell lines available from the American Type Culture Collection (ATCC), including but not limited to Chinese hamster ovary (CHO) cells, $NSO_O$, HeLa cells, baby hamster kidney (BHK) cells, monkey kidney cells (COS), human hepatocellular carcinoma cells (e.g., Hep G2), and a number of other cell lines. Non-mammalian cells including but not limited to bacterial, yeast, insect, and plants can also be used to express recombinant antibodies. Site directed mutagenesis of the antibody CH2 domain to eliminate glycosylation may be preferred in order to prevent changes in either the immunogenicity, pharmacokinetic, and/or effector functions resulting from non-human glycosylation. The expression methods are selected by determining which system generates the highest expression levels and produce antibodies with constitutive IGF-I or IGF-II binding properties.

Further, expression of antibodies of the invention (or other moieties therefrom) from production cell lines can be enhanced using a number of known techniques. For example, the glutamine sythetase and DHFR gene expression systems are common approaches for enhancing expression under certain conditions. High expressing cell clones can be identified using conventional techniques, such as limited dilution cloning and Microdrop technology. The GS system is discussed in whole or part in connection with European Patent Nos. 0 216 846, 0 256 055, and 0 323 997 and European Patent Application No. 89303964.4.

Antibodies of the invention can also be produced transgenically through the generation of a mammal or plant that is transgenic for the immunoglobulin heavy and light chain sequences of interest and production of the antibody in a recoverable form therefrom. In connection with the transgenic production in mammals, antibodies can be produced in, and recovered from, the milk of goats, cows, or other mammals. See, e.g., U.S. Pat. Nos. 5,827,690, 5,756,687, 5,750, 172, and 5,741,957.

In connection with functional analysis of antibodies in accordance with the present invention, such antibodies proved to be potent inhibitors of IGF-I or IGF-II and its binding to its IGF-1R. For example, antibodies in accordance with the present invention, e.g., mAb m705, m706, m708 and m708.2, were demonstrated to bind to IGF-I or to IGF-I and IGF-II. See FIG. 2. For example, antibodies in accordance with the present invention, e.g., mAb m708.2, was shown to inhibit phosphorylation of IGF-1R in MCF-7 breast cancer cells.

The results demonstrated in accordance with the present invention indicate that antibodies of the present invention possess certain qualities that may make the present antibodies more efficacious than current therapeutic antibodies against IGF-I or IGF-II, for treatment of neoplastic disease.

In particular, the antibodies mAb m705, m706, m708 and m708.2 of the invention possess highly desirable properties. Their structural characteristics, functions, or activities provide criteria that facilitate the design or selection of additional antibodies or other molecules as discussed above.

Treatment Regimes

The invention provides pharmaceutical compositions comprising one or a combination of antibodies, e.g., antibodies to IGF-I or IGF-II (monoclonal, polyclonal or single chain Fv; intact or binding fragments thereof) formulated together with a pharmaceutically acceptable carrier. Some compositions include a combination of multiple (e.g., two or more) monoclonal antibodies or antigen-binding portions thereof of the invention. In some compositions, each of the antibodies or antigen-binding portions thereof of the composition is a monoclonal antibody or a human sequence antibody that binds to a distinct, pre-selected epitope of an antigen.

In prophylactic applications, pharmaceutical compositions or medicaments are administered to a patient susceptible to, or otherwise at risk of a disease or condition (i.e., a neoplastic disease) in an amount sufficient to eliminate or reduce the risk, lessen the severity, or delay the outset of the disease, including biochemical, histologic and/or behavioral symptoms of the disease, its complications and intermediate pathological phenotypes presenting during development of the disease. In therapeutic applications, compositions or medicants are administered to a patient suspected of, or already suffering from such a disease in an amount sufficient to cure, or at least partially arrest, the symptoms of the disease (biochemical, histologic and/or behavioral), including its complications and intermediate pathological phenotypes in development of the disease. An amount adequate to accomplish therapeutic or prophylactic treatment is defined as a therapeutically- or prophylactically-effective dose. In both prophylactic and therapeutic regimes, agents are usually administered in several dosages until a sufficient immune response has been achieved. Typically, the immune response is monitored and repeated dosages are given if the immune response starts to wane.

Effective Dosages

Effective doses of the antibody compositions of the present invention, e.g., antibodies to IGF-I or IGF-II, for the treatment of cancer-related conditions and diseases, e.g., metastic cancer, described herein vary depending upon many different factors, including means of administration, target site, physiological state of the patient, whether the patient is human or an animal, other medications administered, and whether treatment is prophylactic or therapeutic. Usually, the patient is a human but nonhuman mammals including transgenic mammals can also be treated. Treatment dosages need to be titrated to optimize safety and efficacy.

For administration with an antibody, the dosage ranges from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. An exemplary treatment regime entails administration once per every two weeks or once a month or once every 3 to 6 months. In some methods, two or more monoclonal antibodies with different binding specificities are administered simultaneously, in which case the dosage of each antibody administered falls within the ranges indicated. Antibody is usually administered on multiple occasions. Intervals between single dosages can be weekly, monthly or yearly. Intervals can also be irregular as indicated by measuring blood levels of antibody in the patient. In some methods, dosage is adjusted to achieve a plasma antibody concentration of 1-1000 μg/ml and in some methods 25-300 μg/ml. Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

Doses for nucleic acids encoding immunogens range from about 10 ng to 1 g, 100 ng to 100 mg, 1 μg to 10 mg, or 30-300 μg DNA per patient. Doses for infectious viral vectors vary from 10-100, or more, virions per dose.

Routes of Administration

Antibody compositions for inducing an immune response, e.g., antibodies to IGF-I or IGF-II, for the treatment of cancer-related conditions and diseases, e.g., metastic cancer, can be administered by parenteral, topical, intravenous, oral, subcutaneous, intraarterial, intracranial, intraperitoneal, intranasal or intramuscular means for prophylactic as inhalants for antibody preparations targeting brain lesions, and/or therapeutic treatment. The most typical route of administration of an immunogenic agent is subcutaneous although other routes can be equally effective. The next most common route is intramuscular injection. This type of injection is most typically performed in the arm or leg muscles. In some methods, agents are injected directly into a particular tissue where deposits have accumulated, for example intracranial injection. Intramuscular injection on intravenous infusion are preferred for administration of antibody. In some methods, particular therapeutic antibodies are injected directly into the cranium. In some methods, antibodies are administered as a sustained release composition or device, such as a Medipad™ device.

Agents of the invention can optionally be administered in combination with other agents that are at least partly effective in treating various diseases including various cancer-related diseases. In the case of tumor metastasis to the brain, agents of the invention can also be administered in conjunction with other agents that increase passage of the agents of the invention across the blood-brain barrier (BBB).

Formulation

Antibody compositions for inducing an immune response, e.g., antibodies to IGF-I or IGF-II for the treatment of cancer-related conditions and diseases, e.g., metastic cancer, are often administered as pharmaceutical compositions comprising an active therapeutic agent, i.e., and a variety of other pharmaceutically acceptable components. (See Remington's Pharmaceutical Science, 15th ed., Mack Publishing Company, Easton, Pa., 1980). The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

Pharmaceutical compositions can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes). Additionally, these carriers can function as immunostimulating agents (i.e., adjuvants).

For parenteral administration, compositions of the invention can be administered as injectable dosages of a solution or suspension of the substance in a physiologically acceptable diluent with a pharmaceutical carrier that can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions. Antibodies can be administered in the form of a depot injection or implant preparation which can be formulated in such a manner as to permit a sustained release of the active ingredient. An exemplary composition comprises monoclonal antibody at 5 mg/mL, formulated in aqueous buffer consisting of 50 mM L-histidine, 150 mM NaCl, adjusted to pH 6.0 with HCl.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, *Science* 249: 1527, 1990 and Hanes, *Advanced Drug Delivery Reviews* 28: 97-119, 1997. The agents of this invention can be administered in the form of a depot injection or implant preparation which can be formulated in such a manner as to permit a sustained or pulsatile release of the active ingredient.

Additional formulations suitable for other modes of administration include oral, intranasal, and pulmonary formulations, suppositories, and transdermal applications.

For suppositories, binders and carriers include, for example, polyalkylene glycols or triglycerides; such suppositories can be formed from mixtures containing the active ingredient in the range of 0.5% to 10%, preferably 1%-2%. Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained release formulations or powders and contain 10%-95% of active ingredient, preferably 25%-70%.

Topical application can result in transdermal or intradermal delivery. Topical administration can be facilitated by co-administration of the agent with cholera toxin or detoxified derivatives or subunits thereof or other similar bacterial toxins. Glenn et al., Nature 391: 851, 1998. Co-administration can be achieved by using the components as a mixture or as linked molecules obtained by chemical crosslinking or expression as a fusion protein.

Alternatively, transdermal delivery can be achieved using a skin patch or using transferosomes. Paul et al., *Eur. J. Immunol.* 25: 3521-24, 1995; Cevc et al., *Biochem. Biophys. Acta* 1368: 201-15, 1998.

The pharmaceutical compositions are generally formulated as sterile, substantially isotonic and in full compliance with all Good Manufacturing Practice (GMP) regulations of the U.S. Food and Drug Administration.

Diagnostic Uses

Characteristics of Antibodies and Antibody Compositions of the invention for Use as Diagnostic Reagents. Human antibodies for use in diagnostic methods to identify metastatic tumor cells, e.g., metastatic breast cancer cells, are preferably produced using the methods described above. The methods result in virtually unlimited numbers of antibodies and antibody compositions of the invention of any epitope binding specificity and very high binding affinity to any desired antigen. In general, the higher the binding affinity of an antibody for its target, the more stringent wash conditions can be performed in an immunoassay to remove nonspecifically bound material without removing target antigen. Accordingly, antibodies and antibody compositions of the invention used in the above assays usually have binding affinities of at least $10^8$, $10^9$, $10^{10}$, $10^{11}$ or $10^{12}$ $M^{-1}$. Further, it is desirable that antibodies used as diagnostic reagents have a sufficient on-rate to reach equilibrium under standard conditions in at least 12 hours, preferably at least five hours and more preferably at least one hour.

Antibodies and antibody compositions of the invention used in the claimed methods preferably have a high immunoreactivity, that is, percentages of antibodies molecules that are correctly folded so that they can specifically bind their target antigen. Such can be achieved by expression of sequences encoding the antibodies in *E. coli* as described above. Such expression usually results in immunoreactivity of at least 80%, 90%, 95% or 99%.

Some methods of the invention employ polyclonal preparations of antibodies and antibody compositions of the invention as diagnostic reagents, and other methods employ monoclonal isolates. The use of polyclonal mixtures has a number of advantages with respect to compositions made of one monoclonal antibody. By binding to multiple sites on a target, polyclonal antibodies or other polypeptides can generate a stronger signal (for diagnostics) than a monoclonal that binds to a single site. Further, a polyclonal preparation can bind to numerous variants of a prototypical target sequence (e.g., allelic variants, species variants, strain variants, drug-induced escape variants) whereas a monoclonal antibody may bind only to the prototypical sequence or a narrower range of variants thereto. However, monoclonal antibodies are advantageous for detecting a single antigen in the presence or potential presence of closely related antigens.

In methods employing polyclonal human antibodies prepared in accordance with the methods described above, the preparation typically contains an assortment of antibodies with different epitope specificities to the intended target antigen. In some methods employing monoclonal antibodies, it is desirable to have two antibodies of different epitope binding specificities. A difference in epitope binding specificities can be determined by a competition assay.

Samples and Target. Although human antibodies can be used as diagnostic reagents for any kind of sample, they are most useful as diagnostic reagents for human samples. Samples can be obtained from any tissue or body fluid of a patient. Preferred sources of samples include, whole blood, plasma, semen, saliva, tears, urine, fecal material, sweat, buccal, skin and hair. Samples can also be obtained from biopsies of internal organs or from cancers. Samples can be obtained from clinical patients for diagnosis or research or can be obtained from undiseased individuals, as controls or for basic research.

The methods can be used for detecting any type of target antigen. Exemplary target antigens including bacterial, fungal and viral pathogens that cause human disease, such as. HIV, hepatitis (A, B, & C), influenza, herpes, *Giardia*, malaria, *Leishmania, Staphylococcus aureus, Pseudomonas aeruginosa*. Other target antigens are human proteins whose expression levels or compositions have been correlated with human disease or other phenotype. Examples of such antigens include adhesion proteins, hormones, growth factors, cellular receptors, autoantigens, autoantibodies, and amyloid deposits. Other targets of interest include tumor cell antigens, such as carcinoembryonic antigen. Other antigens of interest are class I and class II MHC antigens.

Formats for Diagnostic Assays. Human antibodies can be used to detect a given target in a variety of standard assay formats. Such formats include immunoprecipitation, Western blotting, ELISA, radioimmunoassay, and immunometric assays. See Harlow & Lane, supra; U.S. Pat. Nos. 3,791,932; 3,839,153; 3,850,752; 3,879,262; 4,034,074; 3,791,932; 3,817,837; 3,839,153; 3,850,752; 3,850,578; 3,853,987; 3,867,517; 3,879,262; 3,901,654; 3,935,074; 3,984,533; 3,996,345; 4,034,074; and 4,098,876, each incorporated herein by reference in their entirety and for all purposes.

Immunometric or sandwich assays are a preferred format. See U.S. Pat. Nos. 4,376,110; 4,486,530; 5,914,241; and 5,965,375, each incorporated herein by reference in their entirety and for all purposes. Such assays use one antibody or population of antibodies immobilized to a solid phase, and another antibody or population of antibodies in solution. Typically, the solution antibody or population of antibodies is labelled. If an antibody population is used, the population typically contains antibodies binding to different epitope specificities within the target antigen. Accordingly, the same population can be used for both solid phase and solution antibody. If monoclonal antibodies are used, first and second monoclonal antibodies having different binding specificities are used for the solid and solution phase. Solid phase and solution antibodies can be contacted with target antigen in either order or simultaneously. If the solid phase antibody is contacted first, the assay is referred to as being a forward assay. Conversely, if the solution antibody is contacted first, the assay is referred to as being a reverse assay. If target is contacted with both antibodies simultaneously, the assay is referred to as a simultaneous assay. After contacting the target with antibody, a sample is incubated for a period that usually varies from about 10 min to about 24 hr and is usually about 1 hr. A wash step is then performed to remove components of the sample not specifically bound to the antibody being used as a diagnostic reagent. When solid phase and solution antibodies are bound in separate steps, a wash can be performed after either or both binding steps. After washing, binding is quantified, typically by detecting label linked to the solid phase through binding of labelled solution antibody. Usually for a given pair of antibodies or populations of antibodies and given reaction conditions, a calibration curve is prepared from samples containing known concentrations of target antigen. Concentrations of antigen in samples being tested are then read by interpolation from the calibration curve. Analyte can be measured either from the amount of labelled solution antibody bound at equilibrium or by kinetic measurements of bound labelled solution antibody at a series of time points before equilibrium is reached. The slope of such a curve is a measure of the concentration of target in a sample Suitable supports for use in the above methods include, for example, nitrocellulose membranes, nylon membranes, and derivatized nylon membranes, and also particles, such as agarose, a dextran-based gel, dipsticks, particulates, microspheres, magnetic particles, test tubes, microtiter wells, SEPHADEX™. (Amersham Pharmacia Biotech, Piscataway N.J.) Immobilization can be by absorption or by covalent attachment. Optionally, antibodies can be joined to a linker molecule, such as biotin for attachment to a surface bound linker, such as avidin.

Labels

The particular label or detectable group used in the assay is not a critical aspect of the invention, so long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., Dynabeads™), fluorescent dyes (e.g., fluorescein isothiocyanate, Texas red, rhodamine, and the like), radiolabels (e.g., $^{3}H$, $^{14}C$, $^{35}S$, $^{125}I$, $^{121}I$, $^{112}In$, $^{99}mTc$), other imaging agents such as microbubbles (for ultrasound imaging), $^{18}F$, $^{11}C$, $^{15}O$, (for Positron emission tomography), $^{99m}TC$, $^{111}In$ (for Single photon emission tomography), enzymes (e.g., horse radish peroxidase, alkaline phosphatase and others commonly used in an ELISA), and calorimetric labels such as colloidal gold or colored glass or plastic (e.g. polystyrene, polypropylene, latex, and the like) beads. Patents that described the use of such labels include U.S. Pat. Nos. 3,817,837; 3,850,752; 3,939,350; 3,996,345; 4,277,437; 4,275,149; and 4,366,241, each incorporated herein by reference in their entirety and for all purposes. See also *Handbook of Fluorescent Probes and Research Chemicals*, 6$^{th}$ Ed., Molecular Probes, Inc., Eugene Oreg.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, and the like Chemiluminescent compounds include luciferin, and 2,3-dihydrophthalazinediones, e.g., luminol. For a review of various labeling or signal producing systems which may be used, see, U.S. Pat. No. 4,391,904, incorporated herein by reference in its entirety and for all purposes.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple calorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

Frequently, the IGF-I or IGF-II proteins and antibodies to IGF-I or IGF-II will be labeled by joining, either covalently or non-covalently, a substance which provides for a detectable signal.

Toxicity

Preferably, a therapeutically effective dose of the antibody compositions described herein will provide therapeutic benefit without causing substantial toxicity.

Toxicity of the proteins described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the proteins described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the patient's condition. (See, e.g., Fingl et al., 1975, In: The Pharmacological Basis of Therapeutics, Ch. 1, Kits Also within the scope of the invention are kits comprising the compositions (e.g., monoclonal antibodies, human sequence antibodies, human antibodies, multispecific and bispecific molecules) of the invention and instructions for use. The kit can further contain a least one additional reagent, or one or more additional human antibodies of the invention (e.g., a human antibody having a complementary activity which binds to an epitope in the antigen distinct from the first human antibody). Kits typically include a label indicating the intended use of the contents of the kit. The term label includes any writing, or recorded material supplied on or with the kit, or which otherwise accompanies the kit.

The following cDNA clones described in the specification and further described in the examples below will be deposited with the American Type Culture Collection, 10801 University Boulevard, Manassas, Va. 20110-2209 under the Budapest Treaty on Apr. 18, 2007. The cDNA clone for m705 $V_H$ has the ATCC Accession No. indicated: PTA-8342, deposited on Apr. 18, 2007. The cDNA clone for m705 $V_L$ has the ATCC Accession No. indicated: PTA-8342, deposited on Apr. 18, 2007. The cDNA clone for m706 $V_H$ has the ATCC Accession No. indicated: PTA-8344 deposited on Apr. 18, 2007. The cDNA clone for m706 $V_L$ has the ATCC Accession No. indicated: PTA-8344, deposited on Apr. 18, 2007. The cDNA clone for m708 $V_H$ has the ATCC Accession No. indicated: PTA-8343, deposited on Apr. 18, 2007. The cDNA clone for m708 $V_L$ has the ATCC Accession No. indicated: PTA-8343, deposited on Apr. 18, 2007. The cDNA clone for m708.2 $V_H$ has the ATCC Accession No. indicated:PTA-8341, deposited on Apr. 18, 2007. The cDNA clone for m708.2 $V_L$ has the ATCC Accession No. indicated: PTA-8341, deposited on Apr. 18, 2007.

Other embodiments and uses will be apparent to one skilled in the art in light of the present disclosures.

EXEMPLARY EMBODIMENTS

Example 1

Selection of Phage-Displayed human Fabs Against human IGF I

Most, if not all, of the currently available antibodies to IGF-II are not human but are typically of mouse origin. To develop human mAbs against IGF-IIT, we used a large naive human Fab library containing $10^{10}$ different phage-displayed Fabs, which was recently developed. A recombinant human IGFI was conjugated to dynal beads and used as a target antigen for the antibody library panning. After three rounds of panning, screening of 200 random individual phage clones was performed by phage ELISA using IGF I as target. Of clones that exhibited significant binding to IGF I and were sequenced, 3 Fabs had unique sequences; they were expressed in bacteria as soluble Fabs, purified, and tested for binding activity. Two Fabs, designated m705 and m706 showed binding specifically to IGF I only, while one Fab m708, exhibited significant levels of binding to both IGF I and IGF II in ELISA and were selected for affinity maturation and characterization.

$2\times10^8$ independent clones were obtained after the light chain shuffled m708 mutant library construction as described in Material and methods. Two rounds of panning against IGF I conjugated bead were performed and 200 clones from the second round of panning were screened by phage ELISA, 5 unique clones were identified after DNA sequencing and ELISA binding test, clone m708.2 showed the highest binding activity to both IGF I and IGF II was selected for further characterization.

TABLE 1 m705 and m706 antibody protein sequences with CDR1, CDR2, and CDR3 identified.

m705 (IGF-I specific mAb)

(SEQ ID NO: 1)

$V_H$

Q V Q L V Q S G V E V K K P G A S V K V P C K A S <u>G Y T F T S Y Y</u> M H W V R Q A P
                                                              CDR1

G Q G L E W M <u>G I I N P S G G S T</u> S Y A Q K F Q G R V T M T R D T S T S T V Y M E L S
               CDR2

S L R S E D T A V Y Y C <u>A R D D F W S G A V G M D V</u> W G Q G T T V T V S S
                                CDR3

(SEQ ID NO: 2)

$V_L$

D I Q M T Q S P A T L S L S P G E R A T L S C R A S <u>Q D V G S</u> D L A W Y Q Q K P G Q P
                                               CDR1

P R L L V <u>S D A S</u> N R A T G I P A R F S G S G S G T D F K L T I N S L E P E D S A V Y Y
         CDR2

C <u>Q Q R R R W P P G A T F</u> G G G T K V E I K R
        CDR3 m706 (IGF-I specific mAb)

(SEQ ID NO: 3)

$V_H$

E V Q L V Q S G V D V K K P G S S V K V S C K A S <u>G G T F S S Y A</u> I S W V R Q A P G
                                              CDR1

Q G L E W M G <u>G I I P I F G T A</u> N Y A Q K F Q G R V T I T A D E S A S T A Y M E L S S
               CDR2

L R S E D T A V Y Y C <u>A S G Y E G P L W A F D I</u> W G Q G T M V T V S S
                           CDR3

(SEQ ID NO: 4)

$V_L$

Q A S Q S V L T Q P P S V S A A P G Q R V S I S C S G S <u>S S N I G N Y H</u> V S W Y Q H L
                                                CDR1

P G R A P K L L I Y <u>D N S</u> K R P S G I P D R F S G S K S G T S A T L D I T G L Q T G D E
                  CDR2

G D Y Y C <u>A T W D T S L R W V F</u> G T G T K V T V L
         CDR3

TABLE 2 m708 and m708.2 are cross-reactive monoclonal antibodies to IGF-I and IGF-II.
$V_H$ and $V_L$ antibody protein sequences with CDR1, CDR2, and CDR3 identified.

m708

(SEQ ID NO: 5)

$V_H$
Q V Q L Q Q S G A E V K K P G S S V K V S C K A S <u>G G T F S S Y A</u> I S W V R Q A P G
                                                                   CDR1
Q G L E W M G <u>G I I P I L G I A</u> N Y A Q K F Q G R V T I T A D E S T S T A Y M E L S S L
            CDR2
R S E D T A V Y Y C <u>A R G P R G Y S Y N F D Y</u> W G Q G T L V T V S S
                  CDR3

(SEQ ID NO: 6)

$V_L$
D I Q M T Q S P S S L S A S V G D R V T I T C R A S <u>Q S I S S</u> Y L N W Y Q Q K P G K A
                                                   CDR1
P K L L I Y <u>A A S</u> S L Q S G V P S R F S G S G S G T D F T L T I S S L Q P E D F A T Y Y
        CDR2
C <u>Q Q S Y S T P S T F</u> G G G T K V E I K R
    CDR3 m708.2

(SEQ ID NO: 7)

$V_H$
Q V Q L Q Q S G A E V K K P G S S V K V S C K A S <u>G G T F S S Y A</u> I S W V R Q
                                                  CDR1
A P G Q G L E W M G <u>G I I P I L G I A</u> N Y A Q K F Q G R V T I T A D E S T S T A
                CDR2
Y M E L S S L R S E D T A V Y Y C <u>A R G P R G Y S Y N F D Y</u> W G Q G T L V T V S S
                             CDR3

(SEQ ID NO: 8)

$V_L$
D I Q M T Q S P S S L S A S V G D R V T I A C R A S <u>Q T I S R Y</u> L N W Y Q Q K P
                                                CDR1
G K A P K L L I Y <u>A A S</u> S L Q S G V S S R F S G S G S G T E F T L T I S S L Q P E
            CDR2
D F A T Y F C <u>Q Q T Y S P P I T F</u> G Q G T R L E I K R
          CDR3

Table 1 shows the $V_H$ and $V_L$ regions of IGF-I specific monoclonal antibodies M705 and m706. The CDR regions of each antibody are underlined. Table 2 shows the $V_H$ and $V_L$ regions of IGF-I specific and IGF-II specific monoclonal antibodies m708 and m708.2. The CDR regions of each antibody are underlined. The CDR region sequence of m708 and M708.2 are:

$V_L$: Q S I S S (SEQ ID NO: 9, L-CDR1 of m708), $V_L$: Q T I S R Y (amino acids 27-32 of SEQ ID NO: 8, L-CDR1 of m708.2) $V_L$: A A S (SEQ ID NO: 10, L-CDR2 of m708 and m708.2), $V_L$: Q Q S Y S T P S T F (SEQ ID NO: 11, L-CDR3 of m708), Q Q T Y S P P I T F (amino acids 89-98 of SEQ ID NO : 8, L-CDR3 of m708.2)

$V_H$: G G T F S S Y A (SEQ ID NO: 12, H-CDR1 of m708 and m708.2), $V_H$: G I I P I L G I A (SEQ ID NO: 13, H-CDR2 of m708 and m708.2), and $V_H$: A R G P R G Y S Y N F D Y (SEQ ID NO: 14, H-CDR3 of m708 and m708.2).

Figure 1A:
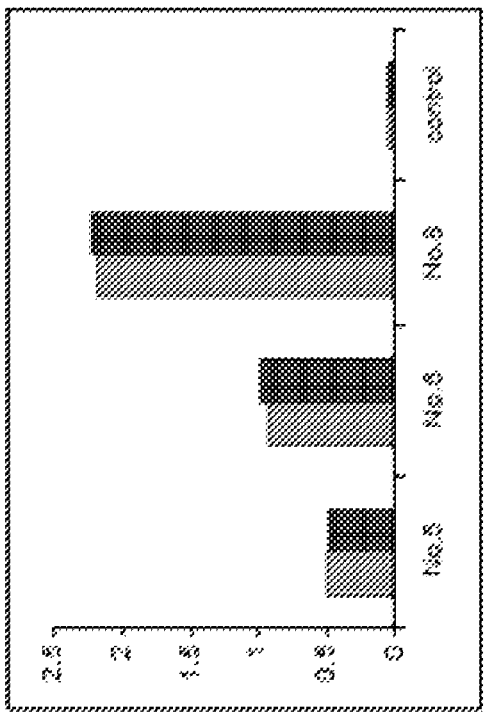

FIG. 1 shows human monoclonal antibodies selected against IGF-I that bind to IGF-I or IGF-I and IGF-II. m705 (No. 5) and m706 (No. 6) react with IGF-I and not with IGF-II. m708 (No. 8) cross reacts with IGF-I and IGF-II.

Figure 2:
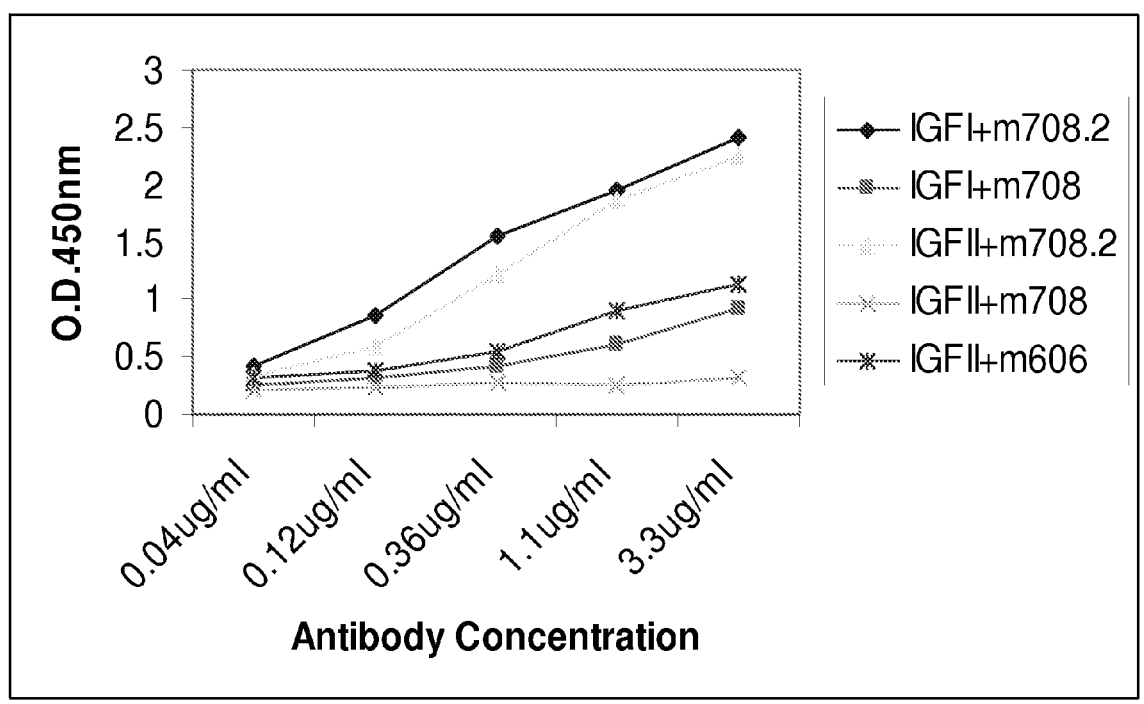
FIG. 2 shows an ELISA binding assay of IgG 708.2 binding to IGF-I and IGF-II.

FIG. 2 shows an ELISA binding assay of IgG 708.2 binding to IGF-I and IGF-II. An ELISA binding assay of m708.2 Fab to human IGF-I and IGF-II is shown using m708 Fab and m606 Fab binding as a control. IgG 708.2 Fab demonstrates a binding affinity for both IGF-I and IGF-II. IgG 606 Fab demonstrates a binding affinity for IGF-II. IgG 708 Fab demonstrates a binding affinity for IGF-I which is greater than its binding affinity for IGF-II.

Example 2

Inhibition of IGF-1R and Insulin Receptor Phosphorylation

Figure 3:
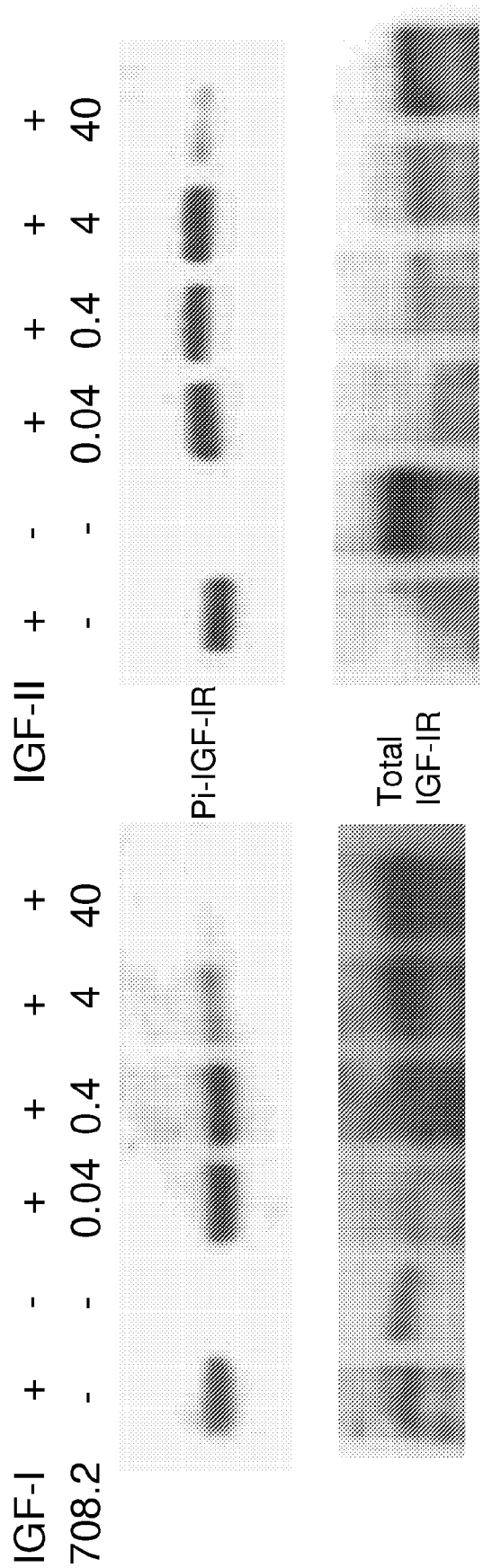
FIG. 3 shows that IgG 708.2 inhibits phosphorylation of IGF-IR in MCF-7 cells.

FIG. 3 shows that IgG 708.2 inhibits phosphorylation of IGF-1R in MCF-7 cells. MCF-7 cells were starved in serum free medium for 6 hours, followed by addition of treatment medium with 1.5 nM IGF-1 or 10 nM IGF-II with indicated concentrations of IgG708.2. Twenty minutes later cells were chilled and lysed. IGF-1R was immunopreciptated, the phosphorylated receptor was detected with a phosphotyrosine specific monoclonal antibody. The total amount of IGF-1R was detected by the same polyclonal antibody used for the immunoprecipitation.

Figure 4:
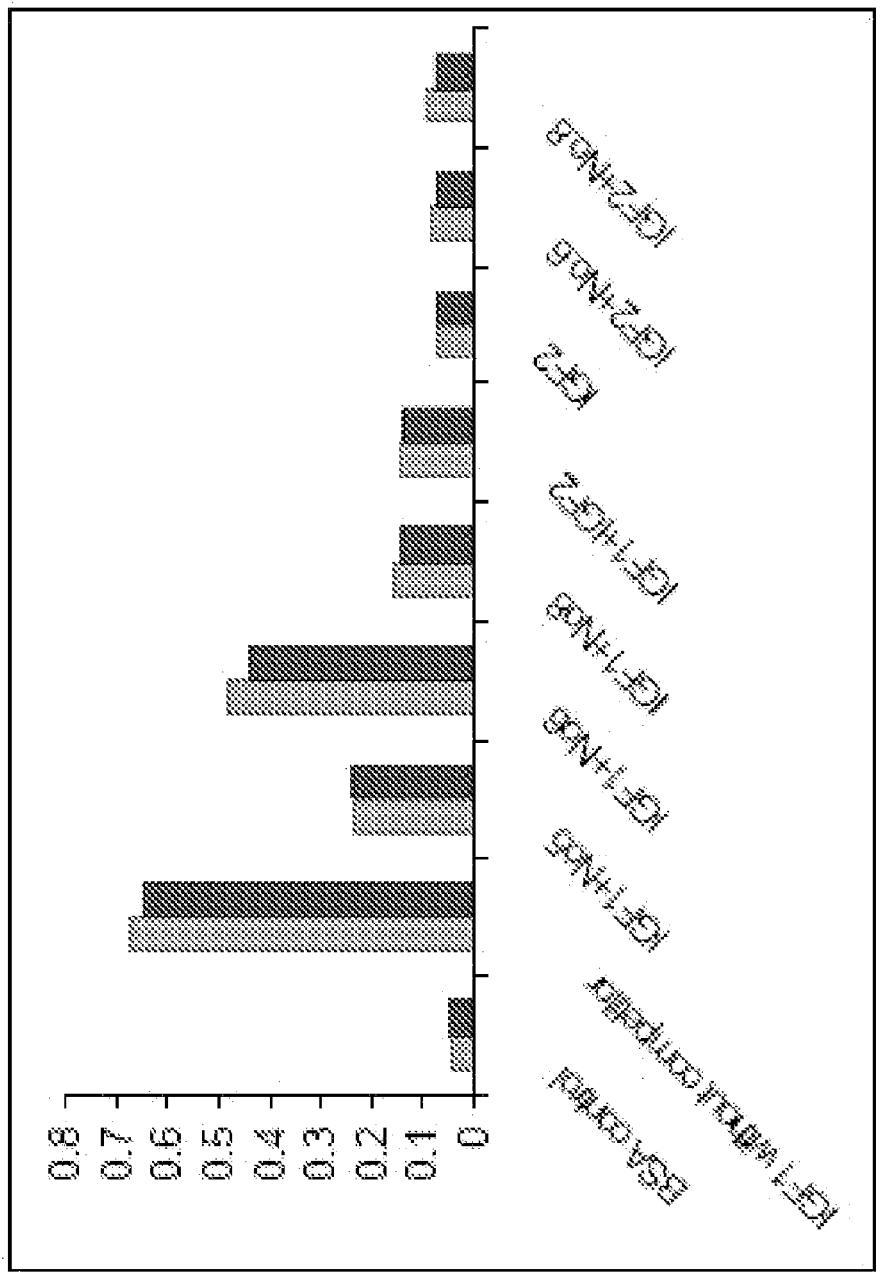
FIG. 4 shows the inhibition of IGF-I binding to soluble IGF-IR by human monoclonal antibodies selected against IGF-I.

FIG. 4 shows the inhibition of TGF-I binding to soluble TGF-1R by human monoclonal antibodies selected against IGF-I. Concentration of m705 and m708 was 400 nM. Concentration of m706 was 100 nM. Concentration of IGF-I was 50 nM and IGF-II was 500 nM.

Figure 5:
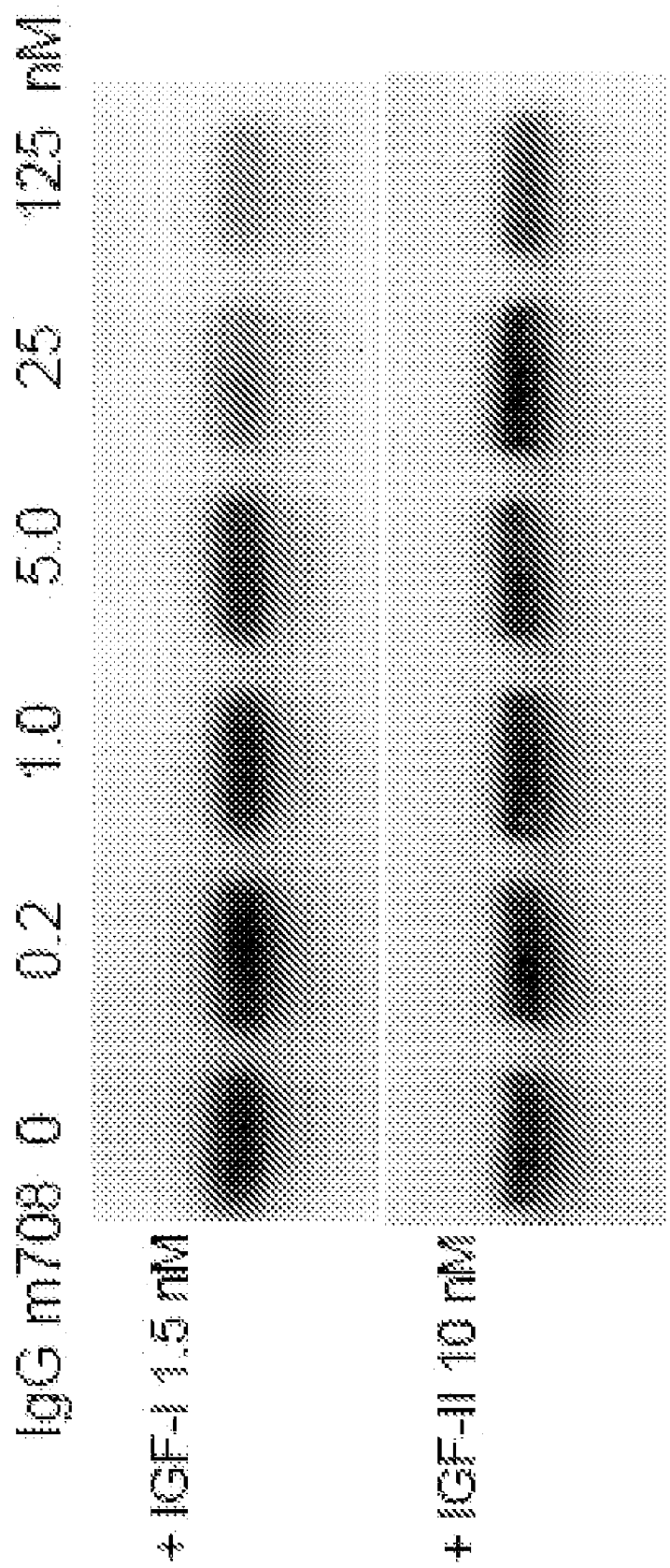
FIG. 5 shows a dose-dependent inhibition of IGF-II and IGF-1-induced IGF-IR phosphorylation in MCF7 cells by anti-IGF-II human antibody IgG1 m708.2.

FIG. 5 shows a dose-dependent inhibition of IGF-II and IGF-1-induced IGF-IR phosphorylation in MCF7 cells by anti-IGF-II human antibody IgG1 m708. Concentration of m708 was from 0 to 125 nM. Concentration of IGF-I was 1.5 nM and IGF-II was 10 nM.

Figure 6:
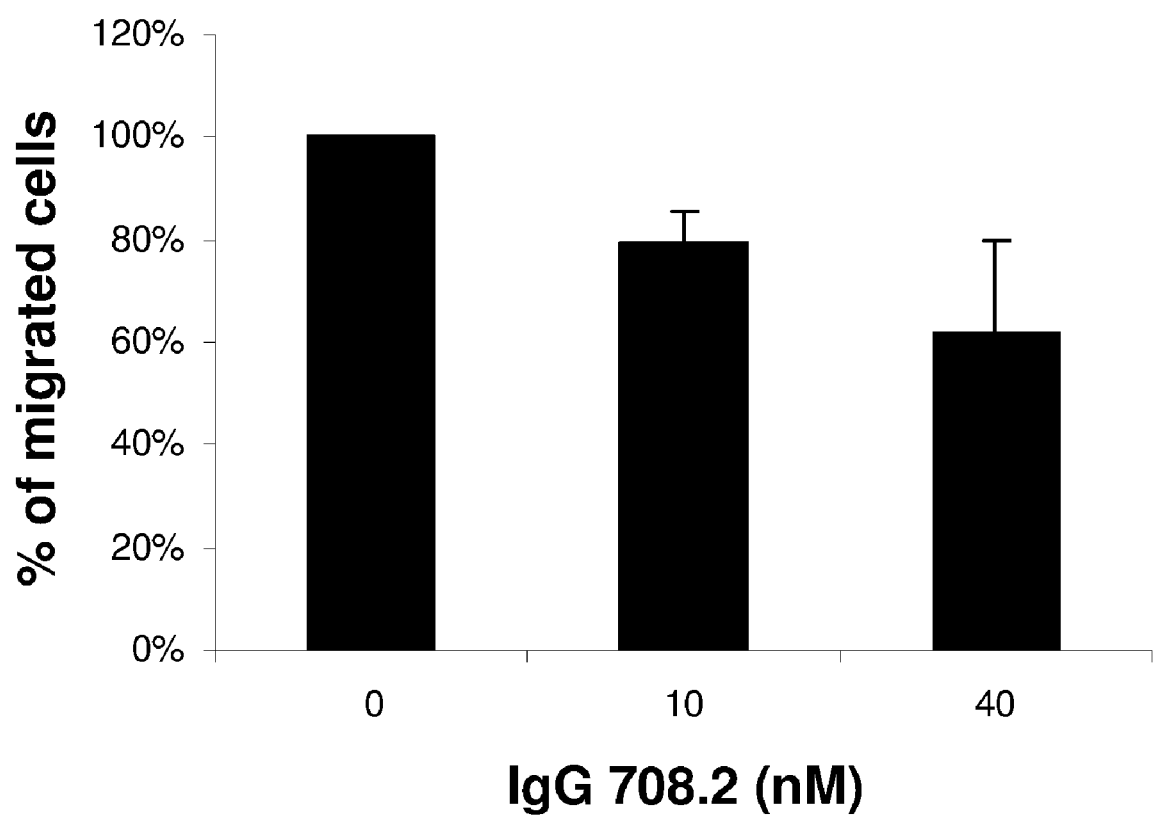
FIG. 6 shows inhibition of cell motility by IgG1 708.2.

FIG. 6 shows inhibition of cancer cell motility by IgG1 m708.2. Motility of cancer cells is essential for tumor metastases. A cell migration assay was performed to test whether IgG m708.2 can inhibit migration of MCF-7 cells through 8 μm membrane pores. IgG m708.2 at 40 nmol/L concentration inhibited 40% of cell migration in medium containing 5% fetal bovine serum.

Figure 7:
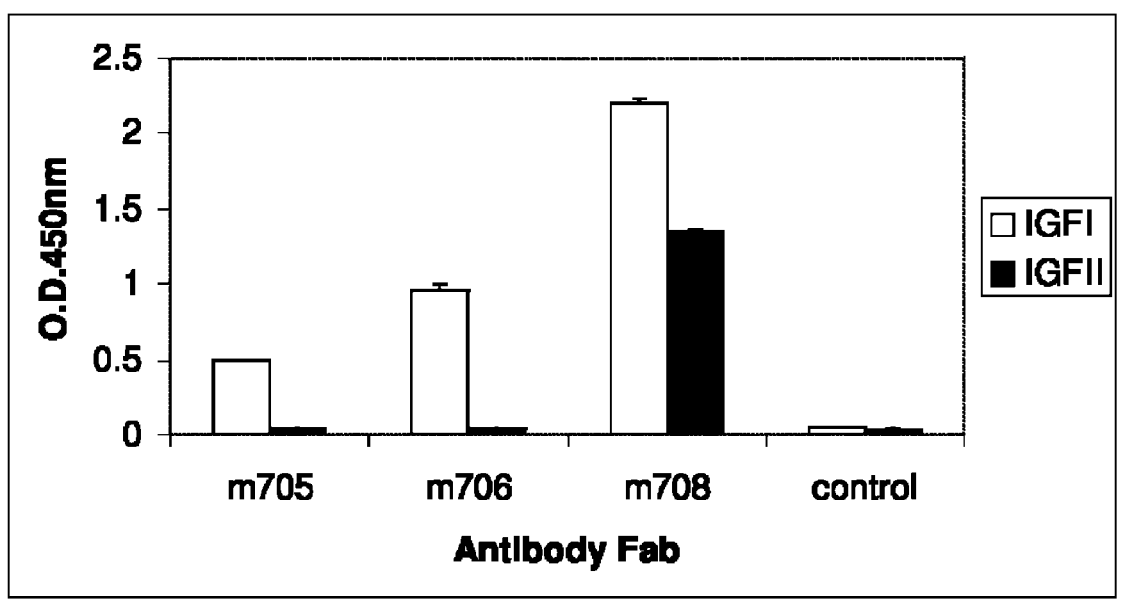
FIG. 7 shows the binding specificity of monoclonal antibodies m705, m706, and m708 to IGF-I and IGF-II by ELISA assay.

FIG. 7 shows the binding specificity of monoclonal antibodies m705, m706, and m708 to IGF-I and IGF-II by ELISA assay. The data show that m705 and m706 specifically bind to IGF-1, and m708 binds to both IGF-I and IGF-II.

Figure 8:
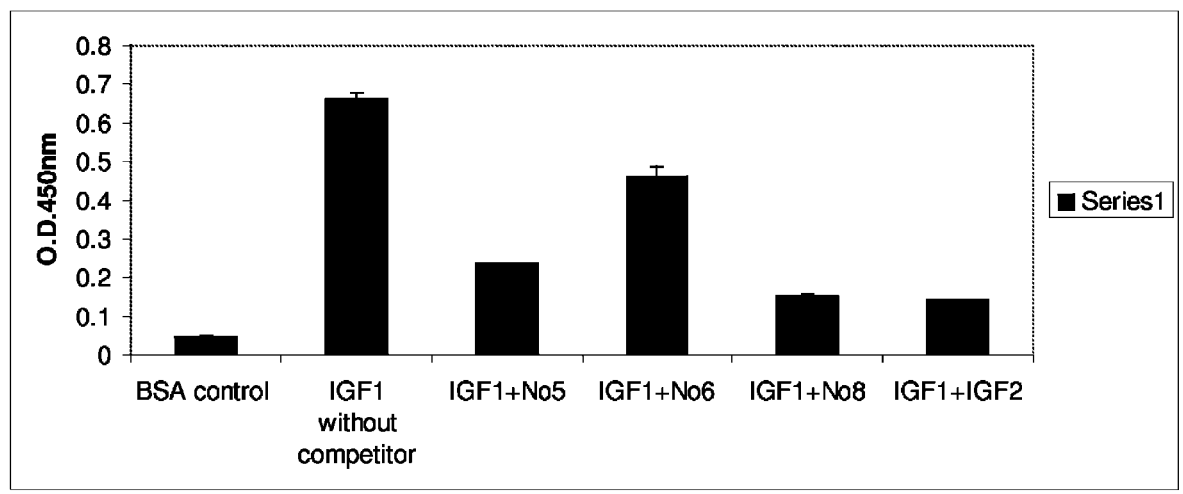
FIG. 8 shows binding competition of monoclonal antibodies m705, m706 and m708 to binding between IGF-I and IGF-1 receptor.

FIG. 8 shows binding competition of monoclonal antibodies m705, m706 and m708 to binding between IGF-I and IGF-1 receptor. m705, m706 and m708 each showed competitive inhibition of binding between IGF-I and IGF-1 receptor.

Figure 9:
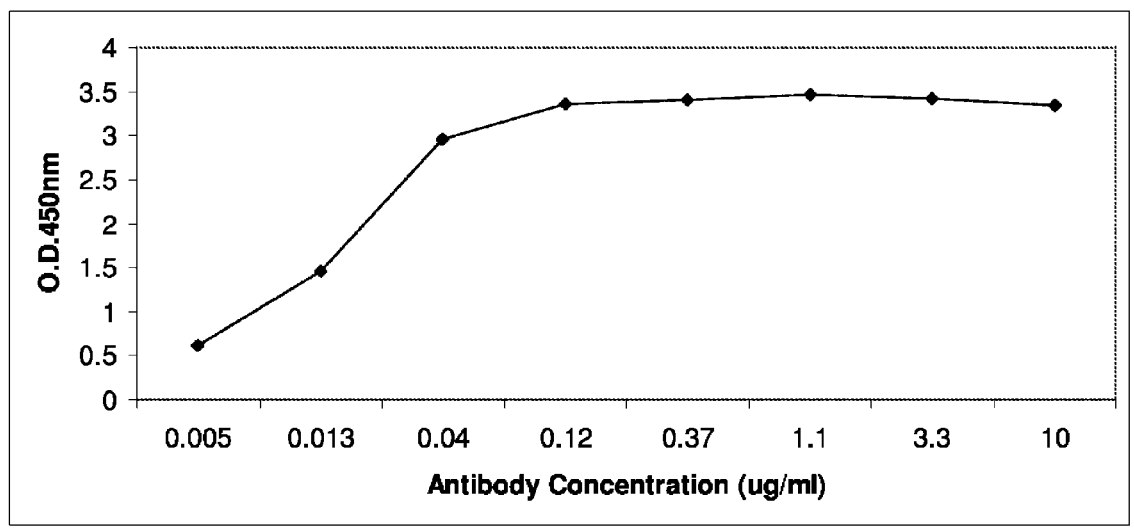
FIG. 9 shows binding of monoclonal antibody m708.2 IgG to IGF-II.

FIG. 9 shows binding of monoclonal antibody m708.2 IgG to IGF-II. The binding affinity Kd of m708.2 IgG to IGF II is about $0.8 \times 10^{-10}$ M.

Monoclonal antibodies m705 and m706 have a high binding specificity for human IGF-I, and do not bind to human insulin. Monoclonal antibodies m708 and m708.2 have a high binding specificity for human IGF-I and human IGF-II, and do not bind to human insulin.

Example 3

Materials and Methods

Phage Display Fab library panning. Recombinant human IGF I was used to screen a human naive Fab phage library containing $10^{10}$ unique clones. Zhang et al., *J. Virol.* 78: 9233-9242, 2004. Recombinant human IGF I was conjugated onto magnetic beads as target for the library panning. 10 μg of the antigen was used in the first round of panning. 1012 amplified phages were used for the panning, after washing, bound phage on the beads were directly used to infect exponentially growing TG1 cells and rescued by M13KO7 helper phage. Panning was repeated two times with 2 μg antigen and 10 times wash after each round. Two hundred individual colonies after the third round were picked and inoculated into 2YT medium in 96-well plate for phage ELISA screening.

Generation and selection of the Light Chain-shuffled Phage Display Library. The original human Fab phage display library was used as the source of the $V_L$ repertoire in the shuffled library. The phagemid preparation from the original library was first digested with Nco I and Spe I followed by electrophoresis on an agarose gel to delete the entire $V_H$ repertoire. The gene encoding the $V_H$ domain of clone m708 was amplified by error-prone PCR kit from Stratagene to introduce random mutations and then fused with CH1 gene fragment by splicing by overlap extension (SOE) PCR. The fused fragment was digested with NcoI and Spe I and purified from gel and was then ligated into the purified backbone vector to create the VL-shuffled Fab repertoire. *E. coli* TG1 cells were transformed with the ligation mixtures via electroporation. The transformed TG1 cells were plated on 2YT agar plates containing 100 μg/ml ampicillin and 2% glucose. After incubation overnight at 37° C., all of the colonies grown on the plates were scraped into 5 ml of 2YTAG medium, mixed with 1.2 ml of 50% glycerol (final concentration 10%), aliquoted, and stored at −70° C. as the mutant library stock.

Selection of the VL-shuffled Library against IGF-I. The library stock (100 μl) was grown to log phase in 20 ml of 2YT medium, rescued with M13K07 helper phage, and amplified overnight in 2YT medium (2YT containing 100 μg/ml of ampicillin and 50 μg/ml of kanamycin) at 30° C. The phage preparation was precipitated in 4% PEG, 0.5 M NaCl, resuspended in 1 ml of PBS as phage library stock. Two round of biopanning were performed on human IGF I conjugated magnetic beads as described in the original library panning.

Conversion from Fab to IgG1. Fabs in pComb3H were cloned into pDR12 which allows simultaneous expression of the heavy chain and light chains. See, for example, Barbas III et al., *Phage Display, A Laboratory Manual*, Cold Spring Harbor Laboratory Press, Cold Spring Harbor, N.Y., 2001. Briefly, the heavy chain variable region was first cloned into pDR12 via XbaI and SacI sites. The light chain sequence (VL+CL) was then cloned into pDR12 via HindIII and EcoRI sites.

Expression of Fab and IgG1. HB2151 cells were transformed with pCombIII plasmid containing Fab sequences. Single fresh colonies were inoculated into 2YT medium+100 Ag/mL ampicillin +0.2% glucose. The culture was shaken at 250 rpm at 37° C. until A600=0.5. Isopropyl-L-thio-h-D-galactopyranoside (1 mmol/L) was added to induce expression. After overnight growth at 30° C., the culture was harvested. Bacteria were centrifuged at 5,000×g for 15 minutes. The pellet was resuspended in PBS with polymycin B (10,000 units/mL). Soluble Fab was released from periplasm by incubating at room temperature for 45 minutes. The extract was clarified at 15,000 g for 30 minutes. The clear supernatant was recovered for purification on protein G column.

IgG1 was expressed in 293 free style cells. 293Fectin was used to transfect 293 free style cells according to the instructions from manufacturer (Invitrogen). Four days after transfection, the culture supernatant was harvested. IgG was purified on protein A column.

ELISA Binding Assay. Antigen was coated on narrow-well, 96-well plate at 50 ng/well overnight at 4° C. For phage ELISA, $10^{10}$ phage from each round of panning was incubated with antigen. Bound phage was detected with anti-M13-HRP polyclonal antibody (Pharmacia, Piscataway, N.J.). For soluble Fab binding assay, anti-Flag HRP conjugate was used to detect the binding.

Determination of Kinetics Rate Constants and Affinity by Surface Plasmon Resonance. Interactions between various Fabs and human IGF I and IGF-II were analyzed by surface plasmon resonance technology using a Biacore 1000 instrument (Pharmacia). IGF I and IGF-II was covalently immobilized onto a sensor chip (CM5) using carbodiimide coupling chemistry. A control reference surface was prepared for nonspecific binding and refractive index changes. For analysis of the kinetics of interactions, varying concentrations of Fabs were injected at flow rate of 30 AL/min using running buffer containing 150 mmol/L NaCl, 3 mmol/L EDTA, and 0.005% P-20 (pH 7.4). The association and dissociation phase data were fitted simultaneously to a 1:1 Langumir global model by using the nonlinear data analysis program BIAevaluation 3.2. All the experiments were done at 25° C.

Phosphorylation Assay. MCF-7 cells were seeded in a six-well plate at $1.0 \times 10^6$ per well in complete growth medium. After overnight culture, cells were rinsed with serum-free DMEM and then cultured in serum-free DMEM for 6 hours. Cells were incubated with various concentrations of recombinant Fab or IgG for 30 minutes, and then IGF-II was added to a final concentration of 10 nmol/L. In some cases, antibody and IGF-II were added to the cultures at the same time but were not premixed. Twenty minutes after addition of IGF II, cells were chilled on ice, rinsed in cold PBS, and lysed in 1 mL of lysis buffer [50 mmol/L HEPES (pH 7.4), 150 mmol/L NaCl, 10% glycerol, 1% Triton X-100, 1.5 mmol/L $MgCl_2$, 2 mmol/L sodium vanadate, and protease inhibitors]. Lysates were kept on ice for 30 minutes, followed by centrifugation at 17,000×g for 30 minutes. The supernatant was used for immunoprecipitation: 20 AL of protein G Sepharose 4B and 2 Ag of rabbit anti-IGF-IR h (C-20, Santa Cruz Biotechnologies, Santa Cruz, Calif.). After extensive wash, the immunoprecipitates were run on 4% to 12% NUPAGE, transferred to polyvinylidene difluoride membrane, and blotted with antiphosphotyrosine mAb 4G10. The membrane was stripped and reprobed with C-20 polyclonal antibody to detect total IGF-IR or C-19 to detect total insulin receptor in the immunoprecipitates. A similar procedure was used for Akt and MAPK but Western blots were done with antibodies recognizing phospho-Akt and phospho-MAPK.

Cell Migration Assay. Transwell culture plates with 8 μm pore size polycarbonate membrane were used according to the instructions of the manufacturer (Corning Life Sciences Q5). Briefly, the bottom wells contained 2.6 mL DMEM with 5% fetal bovine serum and various concentrations of antibodies. DMEM with 5% fetal bovine serum and serum-free DMEM were used as positive and negative controls. The top inserts contained 1.5 mL of $0.5 \times 10^6$ MCF-7 single cell suspension in serum-free DMEM. Cells were incubated in 37° C. incubator. Four hours later, cells attached to the upper side of membrane were cleaned off with cotton-tipped applicator. Cells on the downside of membrane were stained with Hema3 kit (Fischer). The membranes were removed from the transwell, mounted onto microscopic slides, and cells were counted under a microscope.

When ranges are used herein for physical properties, such as molecular weight, or chemical properties, such as chemical formulae, all combinations and subcombinations of ranges and specific embodiments therein are intended to be included.

The disclosures of each patent, patent application and publication cited or described in this document are hereby incorporated herein by reference in their entirety.

Those skilled in the art will appreciate that numerous changes and modifications can be made to the embodiments of the invention and that such changes and modifications can be made without departing from the spirit of the invention. It is, therefore, intended that the appended claims cover all such equivalent variations as fall within the true spirit and scope of the invention.

What is claimed:

1. An isolated fully human monoclonal antibody that binds to human insulin-like growth factor I and human insulin-like growth factor II comprising the amino acid sequence set forth in SEQ ID NO: 7 in its heavy chain variable region and the amino acid sequence set forth in SEQ ID NO:8 in its light chain variable region.

2. The antibody of claim 1, wherein the antibody is an $IgG_1$, an $IgG_2$, an $IgG_3$, an $IgG_4$, an IgM, an $IgA_1$, an $IgA_2$ a secretory IgA, an IgD, or an IgE antibody.

3. The antibody of claim 2, wherein the antibody is an $IgG_1\kappa$ or $IgG_1\lambda$ isotype.

4. The antibody of claim 2, wherein the antibody is an $IgG_4\kappa$ or $IgG_4\lambda$ isotype.

5. The antibody of claim 1, wherein the antibody has one or more of the following characteristics: (i) inhibits IGF-1 receptor phosphorylation in an in vitro MCF-7 breast cancer cell assay at an antibody concentration about 4 nM or greater; (ii) inhibits IGF-I binding or IGF-II binding to IGF-1 receptor; or (iii) inhibits cell migration in a cell migration assay.

6. The antibody of claim 1 having a dissociation equilibrium constant ($K_D$) of approximately $10^{-8}$ M or less, when determined by surface plasmon resonance (SPR) using recombinant human insulin-like growth factor I or human insulin-like growth factor II as an analyte and the antibody as a ligand.

7. The antibody of claim 1, wherein the antibody is capable of binding human insulin-like growth factor I and insulin-like growth factor II with a binding affinity of about $10^8$ $M^{-1}$ or greater.

8. The antibody of claim 1 that is an intact antibody, an intact $IgG_1$ antibody, an intact $IgG_2$ antibody, an intact $IgG_3$ antibody, an intact $IgG_4$ antibody, an intact IgM antibody, an intact $IgA_1$ antibody, an intact $IgA_2$ antibody, an intact secretory IgA antibody, an intact IgD antibody, or an intact IgE antibody, wherein the antibody is glycosylated in a eukaryotic cell.

9. The antibody of claim 1 that is an antibody fragment or a single chain antibody.

10. The antibody of claim 1 that is a binding-domain immunoglobulin fusion protein comprising (i) the variable heavy chain amino acid sequence set forth in SEQ ID NO: 7 fused via a linker peptide to the variable light chain amino acid sequence set forth in SEQ ID NO: 8, fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region.

11. The antibody of claim 1, wherein the antibody is a F(ab')$_2$, Fab, Fv, or Fd fragment.

12. A pharmaceutical composition comprising the antibody of claim 1 and a pharmaceutically acceptable carrier.

13. A method of preparing an antibody that binds human insulin growth factor I comprising expressing a nucleic acid encoding the heavy chain immunoglobulin variable domain sequence and the light chain immunoglobulin variable domain sequence of the antibody of claim 1 in a host cell under conditions that permit expression of the nucleic acid, and recovering the antibody.

14. A method of preparing an antibody that binds human insulin growth factor II comprising expressing a nucleic acid encoding the heavy chain immunoglobulin variable domain sequence or the light chain immunoglobulin variable domain sequence of the antibody of claim 1 in a host cell under conditions that permit expression of the nucleic acid, and recovering the antibody.

15. An isolated fully human monoclonal antibody or an antigen binding fragment thereof comprising one of:
(a) a light chain variable domain comprising three complementarity determining region (CDR) amino acid sequences set forth as SEQ ID NO: 9, SEQ ID NO: 10, and SEQ ID NO: 11, and a heavy chain variable domain comprising three CDR amino acid sequences set forth as SEQ ID NO: 12, SEQ ID NO: 13 and SEQ ID NO: 14, wherein the fully human monoclonal antibody binds to human insulin-like growth factor I and human insulin-like growth factor II;
(b) a light chain variable domain comprising three CDR amino acid sequences set forth as amino acids 27-32 of SEQ ID NO: 8, SEQ ID NO: 10, and amino acids 89-98 of SEQ ID NO: 8, and a heavy chain variable domain comprising three CDR amino acid sequences set forth as SEQ ID NO: 12, SEQ ID NO: 13 and SEQ ID NO: 14, wherein the fully human monoclonal antibody binds to human insulin-like growth factor I and human insulin-like growth factor II;
(c) a heavy chain variable domain comprising the CDR amino acid sequences set forth as amino acids 26-33, amino acids 49-58, and amino acids 97-110 of the amino acid sequence set forth as SEQ ID NO: 1 and a light chain variable domain comprising three CDR amino acid sequences set forth as amino acids 27-31, amino acids 49-52, and amino acids 89-100 of the amino acid sequence set forth as SEQ ID NO: 2 wherein the fully human monoclonal antibody binds human insulin like growth factor I; or
(d) a heavy chain variable domain comprising three CDR amino acid sequences set forth as amino acids 26-33, amino acids 50-58, and amino acids 97-109 of the amino acid sequence set forth as SEQ ID NO: 3 and a light chain variable domain comprising three CDR amino acid sequences set forth as 29-36, amino acids 54-56, and amino acids 93-103 of the amino acid sequence set forth as SEQ ID NO: 4 wherein the fully human monoclonal antibody binds human insulin like growth factor I.

16. The antibody of claim 15, wherein the antibody binds to a human insulin-like growth factor I and human insulin-like growth factor II with an equilibrium association constant (Ka) of at least $10^{10}$ $M^{-1}$.

17. The antibody of claim 15, wherein the antibody binds to a human insulin-like growth factor I and human insulin-like growth factor II with an equilibrium association constant (Ka) of at least $10^9$ $M^{-1}$.

18. The antibody of claim 15, wherein the antibody binds to a human insulin-like growth factor I and human insulin-like growth factor II with an equilibrium association constant (Ka) of at least $10^8$ $M^{-1}$.

19. An isolated recombinant nucleic acid encoding the heavy chain immunoglobulin variable domain sequence and the light chain immunoglobulin variable domain sequence of the antibody of claim 15.

20. A composition comprising the nucleic acid of claim 19 and a pharmaceutically acceptable carrier.

21. A recombinant isolated host cell that comprises the nucleic acid of claim 19.

22. The isolated recombinant nucleic acid of claim 19, encoding:
   (a) the heavy chain amino acid sequence set forth as SEQ ID NO: 1 and the light chain amino acid sequence set forth as SEQ ID NO: 2;
   (b) the heavy chain amino acid sequence set forth as SEQ ID NO: 3 and the light chain amino acid sequence set forth as SEQ ID NO: 4;
   (c) the heavy chain amino acid sequence set forth as SEQ ID NO: 5 and the light chain amino acid sequence set forth as SEQ ID NO: 6; or
   (d) the heavy chain amino acid sequence set forth as SEQ ID NO: 7 and the light chain amino acid sequence set forth as SEQ ID NO: 8.

23. The antibody of claim 19, wherein the antibody is an $IgG_1$, an $IgG_2$, an $IgG_3$, an $IgG_4$, an IgM, an $IgA_1$, an $IgA_2$, a secretory IgA, an IgD, or an IgE antibody.

24. The antibody of claim 19, wherein the antibody is an $IgG_1\kappa$, $IgG_1\lambda$, $IgG_4\kappa$ or $IgG_4\lambda$ isotype.

25. The antibody of claim 19, wherein the antibody has one or more of the following characteristics: (i) inhibits IGF-1 receptor phosphorylation in an in vitro MCF-7 breast cancer cell assay at an antibody concentration of about 4 nM or greater; (ii) inhibits IGF-I binding or IGF-II binding to IGF-1 receptor; or (iii) inhibits cell migration in a cell migration assay.

26. The antibody of claim 19 having a dissociation equilibrium constant ($K_D$) of approximately $10^{-8}$ M or less, when determined by surface plasmon resonance (SPR) using recombinant human insulin-like growth factor I or human insulin-like growth factor II as an analyte and the antibody as a ligand.

27. The antibody of claim 19 that is an intact antibody, an intact $IgG_1$ antibody, an intact $IgG_2$ antibody, an intact $IgG_3$ antibody, an intact $IgG_4$ antibody, an intact IgM antibody, an intact $IgA_1$ antibody, an intact $IgA_2$ antibody, an intact secretory IgA antibody, an intact IgD antibody, or an intact IgE antibody, wherein the antibody is glycosylated in a eukaryotic cell.

28. The antibody of claim 19 that is an antibody fragment or a single chain antibody.

29. The isolated fully human monoclonal antibody of claim 19, comprising the light chain variable domain comprising three complementarity determining region (CDR) amino acid sequences set forth as SEQ ID NO: 9, SEQ ID NO: 10 and SEQ ID NO: 11, and the heavy chain variable domain comprising three CDR amino acid sequences set forth as SEQ ID NO: 12, SEQ ID NO: 13-and SEQ ID NO: 14, wherein the fully human monoclonal antibody binds to human insulin-like growth factor I and human insulin-like growth factor II.

30. The isolated fully human monoclonal antibody of claim 19, comprising the light chain variable domain comprising three CDR sequences set forth as amino acids 27-32 of SEQ ID NO: 8, SEQ ID NO: 10, and amino acids 89-98 of SEQ ID NO: 8, and the heavy chain variable domain comprising three CDR sequences set forth as SEQ ID NO: 12, SEQ ID NO: 13 and SEQ ID NO: 14, wherein the fully human monoclonal antibody binds to human insulin-like growth factor I and human insulin-like growth factor II.

31. The isolated fully human monoclonal antibody of claim 19, comprising the heavy chain variable domain comprising three CDR amino acid sequences set forth as amino acids 26-33, amino acids 49-58, and amino acids 97-110 of the amino acid sequence set forth as SEQ ID NO: 1 and a light chain variable domain comprising three CDR sequences set forth as amino acids 27-31, amino acids 49-52, and amino acids 89-100 of the amino acid sequence set forth as SEQ ID NO: 2 wherein the fully human monoclonal antibody binds human insulin like growth factor I.

32. The isolated fully human monoclonal antibody of claim 19, comprising the heavy chain variable domain comprising three CDR amino acid sequences set forth as amino acids 26-33, amino acids 50-58, and amino acids 97-109 of the amino acid sequence set forth as SEQ ID NO: 3 and a light chain variable domain comprising three CDR amino acid sequences set forth as 29-36, amino acids 54-56, and amino acids 93-103 of the amino acid sequence set forth as SEQ ID NO: 4 wherein the fully human monoclonal antibody binds human insulin like growth factor I.

33. An isolated fully human monoclonal antibody that binds to human insulin-like growth factor I comprising the amino acid sequence set forth in SEQ ID NO: 1 in its human heavy chain variable region and the amino acid sequence set forth in SEQ ID NO: 2 in its human light chain variable region.

34. A pharmaceutical composition comprising the antibody of claim 33 and a pharmaceutically acceptable carrier.

35. An isolated fully human monoclonal antibody that binds to human insulin-like growth factor I comprising the amino acid sequence set forth in SEQ ID NO: 3 in its human heavy chain variable region and the amino acid sequence set forth in SEQ ID NO: 4 in its human light chain variable region.

36. A pharmaceutical composition comprising the antibody of claim 35 and a pharmaceutically acceptable carrier.

37. An isolated fully human monoclonal antibody that binds to human insulin-like growth factor I and to human insulin-like growth factor II comprising the amino acid sequence set forth in SEQ ID NO: 5 in its human heavy chain variable region and the amino acid sequence set forth in SEQ ID NO: 6 in its human light chain variable region.

38. A pharmaceutical composition comprising the antibody of claim 37 and a pharmaceutically acceptable carrier.

39. A method of detecting human insulin growth factor I and human insulin growth factor II in a sample comprising
   (a) providing a sample;
   (b) contacting the sample with the antibody m708 encoded by DNA having ATCC Accession No. PTA-8343 or the m708.2 antibody encoded by DNA having ATCC Accession No. PTA-8341 under conditions that permit binding of either antibody to human insulin growth factor I and insulin growth factor II; and
   (c) detecting the binding of either antibody to human insulin growth factor I and insulin growth factor II in the sample, wherein detection of binding indicates the presence of human insulin growth factor I and insulin growth factor II in the sample.

40. A method of detecting human insulin growth factor I or human insulin growth factor II in a sample comprising
  (a) providing a sample;
  (b) contacting the sample with the antibody m708 encoded by DNA having ATCC Accession No. PTA-8343 or the m708.2 antibody encoded by DNA having ATCC Accession No. PTA-8341 under conditions that permit binding of either antibody to human insulin growth factor I or insulin growth factor II; and
  (c) detecting the binding of either antibody to human insulin growth factor I or insulin growth factor II in the sample, wherein detection of binding indicates the presence of human insulin growth factor I or insulin growth factor II in the sample.

41. A method of detecting human insulin growth factor I in a sample comprising
  (a) providing a sample;
  (b) contacting the sample with the antibody m705 encoded by DNA having ATCC Accession No. PTA-8342 or the m706 encoded by DNA having ATCC Accession No. PTA-8344 under conditions that permit binding of either antibody to human insulin growth factor I; and
  (c) detecting the binding of either antibody to human insulin growth factor I in the sample, wherein detection of binding indicates the presence of human insulin growth factor I in the sample.

42. A method of diagnosing neoplastic disease in a mammalian subject suspected of having neoplastic disease or suspected of being at risk for having neoplastic disease comprising
  obtaining a test sample of blood or tissue from the subject, the test sample comprising a cell population;
  providing at least one antibody that binds IGF-I, wherein the antibody comprises the amino acid sequences set forth in SEQ ID NO: 1, SEQ ID NO: 2, SEQ ID NO: 3, SEQ ID NO: 4, SEQ ID NO: 5, SEQ ID NO: 6, SEQ ID NO: 7, or SEQ ID NO: 8; and
  detecting the presence or absence of an IGF-I antigen on or in cells of the cell population with the antibody, wherein the presence of an IGF-I antigen on or in cells of the cell population is indicative of neoplastic disease or the risk of neoplastic disease in the mammalian subject.

43. The method of claim 42 wherein the antibody that binds IGF-1 comprises the amino acid sequence set forth in SEQ ID NO: 5, SEQ ID NO: 6, SEQ ID NO: 7 or SEQ ID NO: 8.

44. The method of claim 43 comprising detecting the presence or absence of an IGF-I antigen and an IGF-II antigen on or in cells of the cell population with the antibody, wherein the presence of an IGF-I antigen and an IGF-II antigen on or in cells of the cell population is indicative of neoplastic disease or the risk of neoplastic disease in the mammalian subject.

45. The method of claim 44 wherein the presence of an IGF-I antigen and an IGF-II antigen on or in cells of the cell population is indicative of early stage cancer in the mammalian subject.

46. The method of claim 44 wherein the absence of an IGF-I antigen and an IGF-II antigen on or in cells of the cell population is indicative of a disease-free state or a non-measurable disease state in the mammalian subject.

47. The method of claim 44 wherein the presence or absence of an IGF-I antigen and an IGF-II antigen on or in cells of the cell population is indicative of therapeutic efficacy during cancer therapy or cancer recovery.

48. The method of claim 42 wherein an imaging moiety is associated with the antibody.

49. The method of claim 48, wherein the imaging moiety is imaged through magnetic resonance spectroscopy, X-ray spectroscopy, or positron emission tomography (PET).

50. The method of claim 48, wherein the imaging moiety is associated with the antibody via a covalent bond.

51. The method of claim 48, wherein the imaging moiety is associated with the antibody via a non-covalent bond.

52. The method of claim 42, wherein the neoplastic disease is a solid tumor, a hematological malignancy, leukemia, colorectal cancer, breast cancer, uterine cancer, uterine leiomyomas, ovarian cancer, endometrial cancer, polycystic ovary syndrome, endometrial polyps, prostate cancer, prostatic hypertrophy, pituitary cancer, adenomyosis, adenocarcinomas, meningioma, melanoma, bone cancer, multiple myeloma, a CNS cancer, glioma, or astroblastoma.

* * * * *

SEQUENCE LISTING

```
<160> NUMBER OF SEQ ID NOS: 14

<210> SEQ ID NO 1
<211> LENGTH: 121
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (26)..(33)
<223> OTHER INFORMATION: CDR1
<220> FEATURE:
<221> NAME/KEY: MISC_FEATURE
<222> LOCATION: (49)..(58)
<223> OTHER INFORMATION: CDR2
<220> FEATURE:
<221> NAME/KEY: MISC_FEATURE
<222> LOCATION: (97)..(110)
<223> OTHER INFORMATION: CDR3

<400> SEQUENCE: 1

Gln Val Gln Leu Val Gln Ser Gly Val Glu Val Lys Lys Pro Gly Ala
1               5                   10                  15

Ser Val Lys Val Pro Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
```

```
                65                  70                  75                  80
Met Glu Leu Ser Ser Leu Arg Ser Glu Asp Thr Ala Val Tyr Tyr Cys
                        85                  90                  95

Ala Arg Asp Asp Phe Trp Ser Gly Ala Val Gly Met Asp Val Trp Gly
                100                 105                 110

Gln Gly Thr Thr Val Thr Val Ser Ser
        115                 120
```

<210> SEQ ID NO 2
<211> LENGTH: 110
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (27)..(31)
<223> OTHER INFORMATION: CDR1
<220> FEATURE:
<221> NAME/KEY: MISC_FEATURE
<222> LOCATION: (49)..(52)
<223> OTHER INFORMATION: CDR2
<220> FEATURE:
<221> NAME/KEY: MISC_FEATURE
<222> LOCATION: (89)..(100)
<223> OTHER INFORMATION: CDR3

<400> SEQUENCE: 2

```
Asp Ile Gln Met Thr Gln Ser Pro Ala Thr Leu Ser Leu Ser Pro Gly
1               5                   10                  15

Glu Arg Ala Thr Leu Ser Cys Arg Ala Ser Gln Asp Val Gly Ser Asp
                20                  25                  30

Leu Ala Trp Tyr Gln Gln Lys Pro Gly Gln Pro Pro Arg Leu Leu Val
        35                  40                  45

Ser Asp Ala Ser Asn Arg Ala Thr Gly Ile Pro Ala Arg Phe Ser Gly
    50                  55                  60

Ser Gly Ser Gly Thr Asp Phe Lys Leu Thr Ile Asn Ser Leu Glu Pro
65                  70                  75                  80

Glu Asp Ser Ala Val Tyr Tyr Cys Gln Gln Arg Arg Arg Trp Pro Pro
                85                  90                  95

Gly Ala Thr Phe Gly Gly Gly Thr Lys Val Glu Ile Lys Arg
                100                 105                 110
```

<210> SEQ ID NO 3
<211> LENGTH: 120
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (26)..(33)
<223> OTHER INFORMATION: CDR1
<220> FEATURE:
<221> NAME/KEY: MISC_FEATURE
<222> LOCATION: (50)..(58)
<223> OTHER INFORMATION: CDR2
<220> FEATURE:
<221> NAME/KEY: MISC_FEATURE
<222> LOCATION: (97)..(109)
<223> OTHER INFORMATION: CDR3

<400> SEQUENCE: 3

```
Glu Val Gln Leu Val Gln Ser Gly Val Asp Val Lys Lys Pro Gly Ser
1               5                   10                  15

Ser Val Lys Val Ser Cys Lys Ala Ser Gly Gly Thr Phe Ser Ser Tyr
```

```
                20                  25                  30
Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Gly Tyr Glu Gly Pro Leu Trp Ala Phe Asp Ile Trp Gly Gln
            100                 105                 110

Gly Thr Met Val Thr Val Ser Ser
        115                 120

<210> SEQ ID NO 4
<211> LENGTH: 112
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (29)..(36)
<223> OTHER INFORMATION: CDR1
<220> FEATURE:
<221> NAME/KEY: MISC_FEATURE
<222> LOCATION: (54)..(56)
<223> OTHER INFORMATION: CDR2
<220> FEATURE:
<221> NAME/KEY: MISC_FEATURE
<222> LOCATION: (93)..(103)
<223> OTHER INFORMATION: CDR3

<400> SEQUENCE: 4

Gln Ala Ser Gln Ser Val Leu Thr Gln Pro Pro Ser Val Ser Ala Ala
1               5                   10                  15

Pro Gly Gln Arg Val Ser Ile Ser Cys Ser Gly Ser Ser Ser Asn Ile
            20                  25                  30

Gly Asn Tyr His Val Ser Trp Tyr Gln His Leu Pro Gly Arg Ala Pro
        35                  40                  45

Lys Leu Leu Ile Tyr Asp Asn Ser Lys Arg Pro Ser Gly Ile Pro Asp
    50                  55                  60

Arg Phe Ser Gly Ser Lys Ser Gly Thr Ser Ala Thr Leu Asp Ile Thr
65                  70                  75                  80

Gly Leu Gln Thr Gly Asp Glu Ala Asp Tyr Tyr Cys Ala Thr Trp Asp
                85                  90                  95

Thr Ser Leu Arg Trp Val Phe Gly Thr Gly Thr Lys Val Thr Val Leu
            100                 105                 110

<210> SEQ ID NO 5
<211> LENGTH: 120
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (26)..(33)
<223> OTHER INFORMATION: CDR1
<220> FEATURE:
<221> NAME/KEY: MISC_FEATURE
<222> LOCATION: (50)..(58)
<223> OTHER INFORMATION: CDR2
<220> FEATURE:
<221> NAME/KEY: MISC_FEATURE
```

```
<222> LOCATION: (97)..(109)
<223> OTHER INFORMATION: CDR3

<400> SEQUENCE: 5

Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Leu Gly Ile Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Pro Arg Gly Tyr Ser Tyr Asn Phe Asp Tyr Trp Gly Gln
            100                 105                 110

Gly Thr Leu Val Thr Val Ser Ser
        115                 120

<210> SEQ ID NO 6
<211> LENGTH: 108
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (27)..(31)
<223> OTHER INFORMATION: CDR1
<220> FEATURE:
<221> NAME/KEY: MISC_FEATURE
<222> LOCATION: (50)..(52)
<223> OTHER INFORMATION: CDR2
<220> FEATURE:
<221> NAME/KEY: MISC_FEATURE
<222> LOCATION: (89)..(98)
<223> OTHER INFORMATION: CDR3

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ser
                85                  90                  95

Thr Phe Gly Gly Gly Thr Lys Val Glu Ile Lys Arg
            100                 105

<210> SEQ ID NO 7
<211> LENGTH: 120
<212> TYPE: PRT
<213> ORGANISM: Artificial Sequence
<220> FEATURE:
<223> OTHER INFORMATION: Synthetic construct
<220> FEATURE:
```

```
<221> NAME/KEY: MISC_FEATURE
<222> LOCATION: (26)..(33)
<223> OTHER INFORMATION: CDR1
<220> FEATURE:
<221> NAME/KEY: MISC_FEATURE
<222> LOCATION: (50)..(58)
<223> OTHER INFORMATION: CDR2
<220> FEATURE:
<221> NAME/KEY: MISC_FEATURE
<222> LOCATION: (97)..(109)
<223> OTHER INFORMATION: CDR3

<400> SEQUENCE: 7

Gln Val Gln Leu Gln Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Leu Gly Ile Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Pro Arg Gly Tyr Ser Tyr Asn Phe Asp Tyr Trp Gly Gln
            100                 105                 110

Gly Thr Leu Val Thr Val Ser Ser
        115                 120

<210> SEQ ID NO 8
<211> LENGTH: 108
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (27)..(32)
<223> OTHER INFORMATION: CDR1
<220> FEATURE:
<221> NAME/KEY: MISC_FEATURE
<222> LOCATION: (50)..(52)
<223> OTHER INFORMATION: CDR2
<220> FEATURE:
<221> NAME/KEY: MISC_FEATURE
<222> LOCATION: (89)..(98)
<223> OTHER INFORMATION: CDR3

<400> SEQUENCE: 8

Asp Ile Gln Met Thr Gln Ser Pro Ser Ser Leu Ser Ala Ser Val Gly
 1               5                  10                  15

Asp Arg Val Thr Ile Ala Cys Arg Ala Ser Gln Thr Ile Ser Arg Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Ser Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Phe Cys Gln Gln Thr Tyr Ser Pro Pro Ile
                85                  90                  95

Thr Phe Gly Gln Gly Thr Arg Leu Glu Ile Lys Arg
            100                 105
```

```
<210> SEQ ID NO 9
<211> LENGTH: 5
<212> TYPE: PRT
<213> ORGANISM: Artificial Sequence
<220> FEATURE:
<223> OTHER INFORMATION: Synthetic construct

<400> SEQUENCE: 9

Gln Ser Ile Ser Ser
1               5

<210> SEQ ID NO 10
<211> LENGTH: 3
<212> TYPE: PRT
<213> ORGANISM: Artificial Sequence
<220> FEATURE:
<223> OTHER INFORMATION: Synthetic construct

<400> SEQUENCE: 10

Ala Ala Ser
1

<210> SEQ ID NO 11
<211> LENGTH: 10
<212> TYPE: PRT
<213> ORGANISM: Artificial Sequence
<220> FEATURE:
<223> OTHER INFORMATION: Synthetic construct

<400> SEQUENCE: 11

Gln Gln Ser Tyr Ser Thr Pro Ser Thr Phe
1               5                   10

<210> SEQ ID NO 12
<211> LENGTH: 8
<212> TYPE: PRT
<213> ORGANISM: Artificial Sequence
<220> FEATURE:
<223> OTHER INFORMATION: Synthetic construct

<400> SEQUENCE: 12

Gly Gly Thr Phe Ser Ser Tyr Ala
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic construct

<400> SEQUENCE: 13

Gly Ile Ile Pro Ile Leu Gly Ile Ala
1               5

<210> SEQ ID NO 14
<211> LENGTH: 13
<212> TYPE: PRT
<213> ORGANISM: Artificial Sequence
<220> FEATURE:
<223> OTHER INFORMATION: Synthetic construct

<400> SEQUENCE: 14

Ala Arg Gly Pro Arg Gly Tyr Ser Tyr Asn Phe Asp Tyr
1               5                   10
```